(12) United States Patent
Baker

(10) Patent No.: US 11,324,715 B2
(45) Date of Patent: May 10, 2022

(54) BISMUTH-THIOL COMPOSITIONS AND METHODS FOR TREATING WOUNDS

(71) Applicant: Microbion Corporation, Bozeman, MT (US)

(72) Inventor: Brett Hugh James Baker, Bozeman, MT (US)

(73) Assignee: MICROBION CORPORATION, Bozeman, MT (US)

( * ) Notice: Subject to any disclaimer, the term of this patent is extended or adjusted under 35 U.S.C. 154(b) by 0 days.

(21) Appl. No.: 17/526,535

(22) Filed: Nov. 15, 2021

(65) Prior Publication Data

US 2022/0071943 A1 Mar. 10, 2022

Related U.S. Application Data

(62) Division of application No. 16/528,097, filed on Jul. 31, 2019, now Pat. No. 11,207,288.

(60) Provisional application No. 62/820,006, filed on Mar. 18, 2019, provisional application No. 62/712,555, filed on Jul. 31, 2018.

(51) Int. Cl.
  *A61K 31/29* (2006.01)
  *A61P 17/02* (2006.01)
  *A61K 9/14* (2006.01)

(52) U.S. Cl.
  CPC .............. *A61K 31/29* (2013.01); *A61K 9/14* (2013.01); *A61P 17/02* (2018.01)

(58) Field of Classification Search
  CPC ............ A61K 31/29; A61K 9/14; A61P 17/02
  See application file for complete search history.

(56) References Cited

U.S. PATENT DOCUMENTS 10,835,510 B2 * 11/2020 Baker .................... A61K 45/06

* cited by examiner

*Primary Examiner* — Carlos A Azpuru
(74) *Attorney, Agent, or Firm* — Cooley LLP

(57) ABSTRACT

The invention relates to bismuth-thiol compounds and pharmaceutical preparations thereof. The invention further relates to methods for treating a topical wound, comprising administering to a subject in need thereof a therapeutically effective amount of a composition comprising a bismuth-thiol compound, wherein the composition is applied to the infection. Methods for treating microbial infections such as diabetic foot infections are also provided.

18 Claims, 10 Drawing Sheets

BISMUTH-THIOL COMPOSITIONS AND METHODS FOR TREATING WOUNDS

CROSS REFERENCE TO RELATED APPLICATIONS

Figure 1:
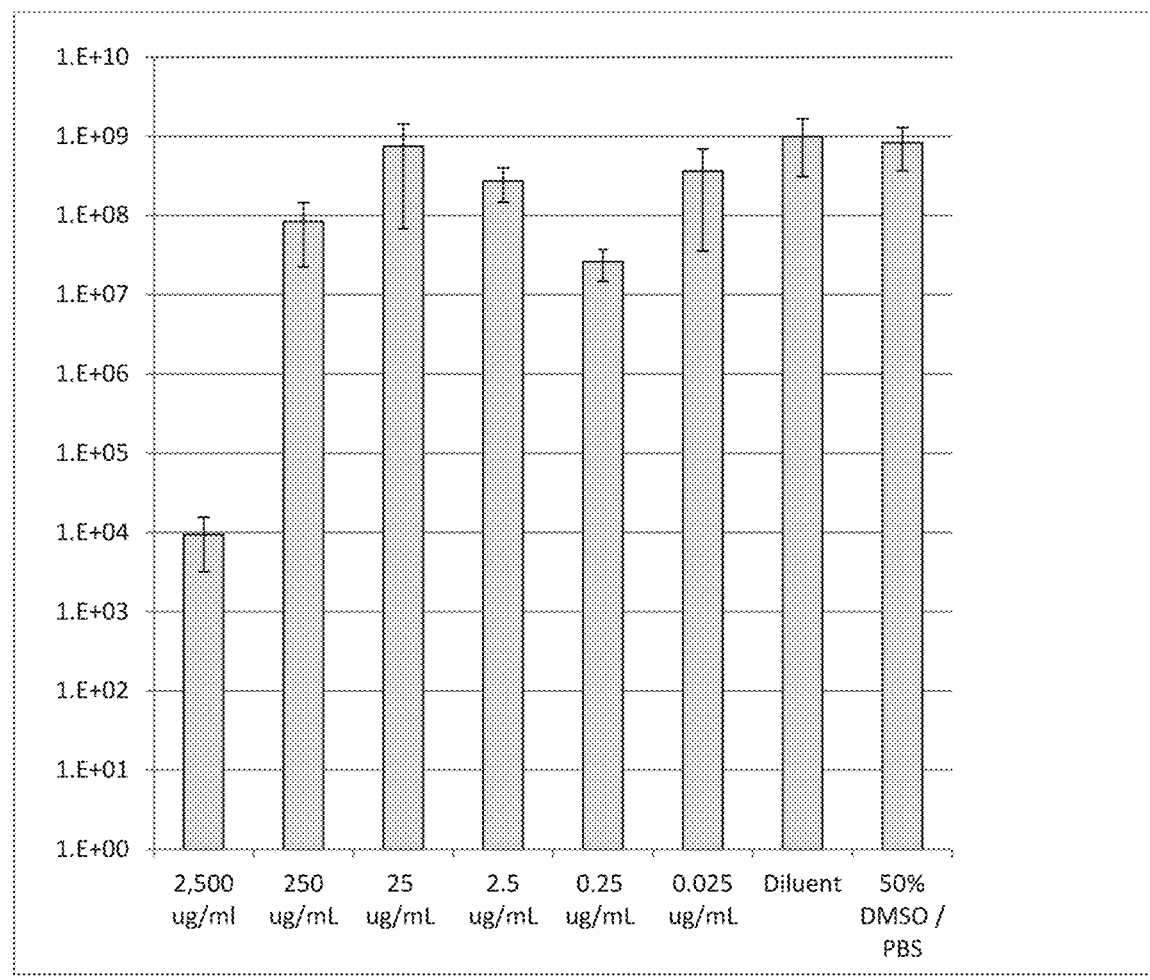

This application is a divisional of U.S. patent application Ser. No. 16/528,097, filed Jul. 31, 2019, which claims the benefit of U.S. Provisional Application No. 62/712,555, filed Jul. 31, 2018 and U.S. Provisional Application No. 62/820,006, filed Mar. 18, 2019, the contents of which are incorporated herein by reference in their entireties.

BACKGROUND

Diabetic foot infections (DFIs) are a frequent and serious complication of diabetes mellitus (DM) and are the world leading cause of non-traumatic lower limb amputation (Jeffcoate W J, et al. 2003. Lancet 361:1545-1551). In current clinical practice, the treatment of DFIs includes debridement and systemic antibiotics (see, e.g., Lipsky B A, et al. 2004. Clin Infect Dis. 39:885-910). Nonetheless, because of deficient vascularization and the local microenvironment, antibiotic concentrations are many times sub-therapeutic (Lipsky B A, et al. 2009. Clin Infect Dis. 49:1541-1549). Moreover, the increasing incidence of multidrug resistant organisms, such as methicillin-resistant *Staphylococcus aureus*, as well as pan-drug-resistant non-fermenting negative bacilli, is threatening the outcome in increasing numbers of community and hospitalized patients (Mendes J J, et al. 2012. Diabetes Res Clin Pract. 95(1):153-161; Tascini C, et al. 2011. Diabetes Res Clin Pract 94 (1):133-139). Accordingly, there remains a need to identify new strategies for the treatment, control, and management of DFIs.

SUMMARY

In some embodiments, the present disclosure provides methods for treating a topical wound, comprising administering to a subject in need thereof a therapeutically effective amount of a composition comprising a bismuth-thiol compound, wherein the composition is applied to the infection (e.g. applied to the surface of the infection and/or surrounding skin and tissue and/or into the wound itself). The topical wound may be a skin ulcer (e.g. a skin ulcer on a lower extremity). In some embodiments, the skin ulcer is one or more of foot ulcer, diabetic foot ulcer, ischemic ulcer, gangrenous ulcer, venous stasis ulcer, decubitus ulcer, Buruli ulcer, or traumatic ulcer. In some embodiments, the topical wound is infected by one or more bacterial and/or fungal pathogens. In some embodiments, the topical wound is a diabetic foot ulcer. In some embodiments, the diabetic foot ulcer is a diabetic foot ulcer infection. In some embodiments, the topical wound is infected with one or more of the following bacterial pathogens: *Staphylococcus aureus*, MIRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*.

In some embodiments of the methods for treating a topical wound, the subject experiences one or more of the following outcomes following the completion of dosing:
a) the wound is healed or substantially healed within 12 weeks of the first administration of the composition; and/or
b) the prevention of amputation and/or infection-related surgery; and/or
c) the wound is closed partially or fully; and/or
d) the wound is reduced in size from about a 1% reduction relative to the original wound size to total elimination of the wound; and/or
e) the wound is 30 days old or greater (i.e. at the time of initiation of treatment) and is healed or substantially healed.

In some embodiments, the subject experiences two or more of the recited outcomes. In some embodiments, the subject experiences three or more of the recited outcomes. In some embodiments, the subject experiences four or more of the recited outcomes. In some embodiments, the subject experiences all of the recited outcomes.

In some embodiments of the methods for treating a topical wound, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol. In some embodiments, the BT compound is BisEDT. In some embodiments, the composition is a suspension of microparticles comprising said BT compounds having a volumetric mean diameter (VMD) from about 0.4 µm to about 5 µm.

In some embodiments of the methods for treating a topical wound, the BT composition comprises BisEDT and the applied BisEDT is present on the surface at a concentration greater than about 20 µg/cm$^2$. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for treating a topical wound, after administration of the BT composition, one or more of the following occurs: (i) reducing and or dispersing a microbial (e.g. bacterial and/or fungal) biofilm, (ii) impairing growth or formation of a microbial (e.g. bacterial and/or fungal) biofilm, and (iii) preventing reformation or spread of a microbial (e.g. bacterial and/or fungal) biofilm. In some embodiments, the BT composition treats, manages, and/or lessens the severity of the diabetic foot infection by one or both of: (i) prevention of the infection by the bacterial or fungal pathogen; and/or (ii) reduction of the bacterial or fungal pathogen. In some embodiments, the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm formation by the bacterial or fungal pathogen; (iv) inhibition of biofilm or microbial pathogen invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

In some embodiments of the methods for treating a topical wound, the administered BT composition is present on the surface at a concentration from about 1 µg/cm$^2$ to about 1,000,000 µg/cm$^2$ (e.g. about 1 µg/cm$^2$ to about 10,000 µg/cm$^2$). In some embodiments, the administered BT composition is present on the surface at a concentration from about 50 µg/cm$^2$ to about 200 µg/cm$^2$. In some embodiments, the applied BT composition is present on the surface at a concentration from about 250 µg/cm$^2$ to about 5,000 µg/cm$^2$.

In some embodiments of the methods for treating a topical wound, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks to about 10 weeks.

In some embodiments of the methods for treating a topical wound, the wound area is from about 0.1 cm$^2$ to about 250 cm$^2$. In some embodiments of the methods for treating a topical wound, the wound area is from about 250 cm$^2$ to about 500 cm$^2$. For example, the wound area may be the wound area for one wound or more than one wound. In such embodiments, the total wound area may be much larger than 500 cm$^2$.

In some embodiments, the present disclosure provides methods for treating a microbial (e.g. bacterial and/or fungal) infection, comprising administering to a subject in need thereof a therapeutically effective amount of a composition comprising a bismuth-thiol compound, wherein the composition is applied to the infection (e.g. applied to the surface of the infection). In some embodiments, the microbial (e.g. bacterial and/or fungal) infection is a diabetic foot infection. In some embodiments, the microbial (e.g. bacterial and/or fungal) infection comprises one or more of the following bacterial pathogens: *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*. In some embodiments, the infection is associated with a wound (e.g. an ulcer) and the subject experiences one or more of the following outcomes following the completion of dosing:

a) the wound is healed or substantially healed within 12 weeks (e.g. within 4 weeks) of the first administration of the composition; and/or b) the prevention of amputation and/or infection-related surgery; and/or c) the wound is closed partially or fully; and/or d) the wound is reduced in size from about a 1% reduction relative to the original wound size to total elimination of the wound; and/or e) the wound is 30 days old or greater and is healed or substantially healed.

In some embodiments, the subject experiences two or more of the recited outcomes. In some embodiments, the subject experiences three or more of the recited outcomes. In some embodiments, the subject experiences four or more of the recited outcomes. In some embodiments, the subject experiences all of the recited outcomes.

In some embodiments of the methods for treating a microbial (e.g. bacterial and/or fungal) infection, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol. In some embodiments, the BT compound is BisEDT. In some embodiments, the composition is a suspension of microparticles comprising said BT compounds having a volumetric mean diameter (VMD) from about 0.4 µm to about 5 µm In some embodiments of the methods for treating a microbial (e.g. bacterial and/or fungal) infection, the BT composition comprises BisEDT and the applied BisEDT is present on the surface at a concentration greater than about 20 µg/cm$^2$.

In some embodiments of the methods for treating a microbial (e.g. bacterial and/or fungal) infection, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for treating a microbial (e.g. bacterial and/or fungal) infection, the method comprises at least one of: (i) reducing and or dispersing a microbial (e.g. bacterial and/or fungal) biofilm, (ii) impairing growth or formation of a microbial (e.g. bacterial and/or fungal) biofilm, and (iii) preventing reformation or spread of a microbial (e.g. bacterial and/or fungal) biofilm. In some embodiments, the BT composition treats, manages or lessens the severity of the diabetic foot infection by one or both of: (i) prevention of the infection by the bacterial or fungal pathogen; and (ii) reduction of the bacterial or fungal pathogen. In some embodiments, the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm or microbial pathogen formation by the bacterial or fungal pathogen; (iv) inhibition of biofilm invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

In some embodiments of the methods for treating a microbial (e.g. bacterial and/or fungal) infection, the applied BT composition is present on the surface at a concentration from about 1 µg/cm$^2$ to about 1,000,000 µg/cm$^2$ (e.g. about 1 μg/cm² to about 10,000 μg/cm²). In some embodiments, the applied BT composition is present on the surface at a concentration from about 50 μg/cm² to about 100 μg/cm². In some embodiments, the applied BT composition is present on the surface at a concentration from about 250 μg/cm² to about 5,000 μg/cm².

In some embodiments of the methods for treating a microbial (e.g. bacterial and/or fungal) infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 10 weeks.

In some embodiments of the methods for treating a microbial (e.g. bacterial and/or fungal) infection, the wound area is from about 0.1 cm² to about 250 cm². In some embodiments of the methods for treating a microbial (e.g. bacterial and/or fungal) infection, the wound area is from about 250 cm² to about 500 cm². The wound area may be the wound area for one wound or more than one wound.

In some embodiments, the present disclosure provides methods for healing a wound in a subject having a diabetic foot infection, comprising administering the subject a therapeutically effective amount of a composition comprising BisEDT, wherein the composition is a suspension of microparticles comprising said BisEDT wherein at least 70% of the microparticles have a volumetric mean diameter (VMD) from about 0.4 μm to about 5 μm, and wherein the composition is applied to the infection (e.g. applied to the surface of the infection) and the wound is healed or substantially healed within 12 weeks of the first administration of the composition. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for healing a wound in a subject having a diabetic foot infection, the applied BT composition is present on the surface at a concentration from about 1 μg/cm² to about 1,000,000 μg/cm² (e.g. about 1 μg/cm² to about 10,000 μg/cm²). In some embodiments, the applied BT composition is present on the surface at a concentration from about 50 μg/cm² to about 100 μg/cm². In some embodiments, the applied BT composition is present on the surface at a concentration greater than about 100 μg/cm² (e.g. as a dosage from about 250 μg/cm² to about 5,000 μg/cm²).

In some embodiments of the methods for healing a wound in a subject having a diabetic foot infection, the BT composition is administered three times per day, two times per day, once daily, every other day, once every three days, three times per week, once every week, once every other week, once every month, or once every other month. In some embodiments, the wound is healed 4 weeks, 8 weeks or 12 weeks after the first administration of the BT composition. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks.

In some embodiments of the methods for healing a wound in a subject having a diabetic foot infection, the wound area is from about 0.1 cm² to about 250 cm². In some embodiments, the wound area is from about 250 cm² to about 500 cm². The wound area may be the wound area for one wound or more than one wound.

In some embodiments, the present disclosure provides methods for reducing the risk of amputation and/or infection-related surgery in a subject having a diabetic foot infection, comprising administering to the subject a therapeutically effective amount of a composition comprising BisEDT, wherein the composition is applied to the infection (e.g. applied to the surface of the infection) and the risk of amputation and/or infection-related surgery is reduced from about 1% to about 100% relevant to a similarly situated subject not treated with a therapeutically effective amount of a composition comprising a bismuth-thiol compound. In some embodiments, the composition is a suspension of microparticles comprising said BisEDT having a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for reducing the risk of amputation and/or infection-related surgery in a subject having a diabetic foot infection, the applied BT composition is present on the surface at a concentration from about 1 μg/cm² to about 1,000,000 μg/cm² (e.g. about 1 μg/cm² to about 10,000 μg/cm²). In some embodiments, the applied BT composition is present on the surface at a concentration from about 50 μg/cm² to about 100 μg/cm². In some embodiments, the applied BT composition is present on the surface at a concentration greater than about 100 μg/cm² (e.g. as a dosage from about 250 μg/cm² to about 5,000 μg/cm²).

In some embodiments, of the methods for reducing the risk of amputation and/or infection-related surgery in a subject having a diabetic foot infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks.

In some embodiments, of the methods for reducing the risk of amputation and/or infection-related surgery in a subject having a diabetic foot infection, the wound area is from about 0.1 cm² to about 250 cm². In some embodiments, the wound area is from about 250 cm² to about 500 cm². The wound area may be the wound area for one wound or more than one wound.

In some embodiments, the present disclosure provides methods for closing a wound in a subject having a diabetic foot infection, comprising administering to the subject a therapeutically effective amount of a composition comprising BisEDT. In some embodiments, the composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for closing a wound in a subject having a diabetic foot infection, the applied BT composition is present on the surface at a concentration from about 1 µg/cm$^2$ to about 1,000,000 µg/cm$^2$ (e.g. about 1 µg/cm$^2$ to about 10,000 µg/cm$^2$). In some embodiments, the applied BT composition is present on the surface at a concentration from about 50 µg/cm$^2$ to about 100 µg/cm$^2$. In some embodiments, the applied BT composition is present on the surface at a concentration greater than about 100 µg/cm$^2$ (e.g. as a dosage from about 250 µg/cm$^2$ to about 5,000 µg/cm$^2$).

In some embodiments, of the methods for closing a wound in a subject having a diabetic foot infection, the composition is applied to the infection (e.g. applied to the surface of the infection) and the wound is closed within 12 weeks of the first administration of the composition. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks.

In some embodiments, of the methods for closing a wound in a subject having a diabetic foot infection, the wound area is from about 0.1 $cm^2$ to about 250 $cm^2$. In some embodiments, the wound area is from about 250 $cm^2$ to about 500 $cm^2$. The wound area may be the wound area for one wound or more than one wound.

In some embodiments, the present disclosure provides methods for wound size reduction in a subject having a diabetic foot infection, comprising administering to the subject a therapeutically effective amount of a composition comprising BisEDT, wherein the composition is applied to the infection (e.g. applied to the surface of the infection) and the wound is reduced in size from about a 1% reduction relative to the original wound size to total elimination of the wound within 12 weeks of the first administration of the composition. In some embodiments, the wound is reduced by about 10%, 20%, 30%, 40%, 50%, 60%, 70%, 80%, or 90%. In some embodiments, the wound is reduced by about 50%.

In some embodiments, of the methods for wound size reduction in a subject having a diabetic foot infection, the composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for wound size reduction in a subject having a diabetic foot infection, the applied BT composition is present on the surface at a concentration from about 1 μg/$cm^2$ to about 1,000,000 μg/$cm^2$ (e.g. about 1 μg/$cm^2$ to about 10,000 μg/$cm^2$). In some embodiments, the applied BT composition is present on the surface at a concentration from about 50 μg/$cm^2$ to about 100 μg/$cm^2$. In some embodiments, the applied BT composition is present on the surface at a concentration greater than about 100 μg/$cm^2$ (e.g. as a dosage from about 250 μg/$cm^2$ to about 5,000 μg/$cm^2$).

In some embodiments, of the methods for wound size reduction in a subject having a diabetic foot infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks.

In some embodiments, of the methods for wound size reduction in a subject having a diabetic foot infection, the wound area is from about 0.1 $cm^2$ to about 250 $cm^2$. In some embodiments, the wound area is from about 250 $cm^2$ to about 500 $cm^2$. The wound area may be the wound area for one wound or more than one wound. In some embodiments, the wound surface area of said wound is reduced by 50% 12 weeks after the first administration of the BT composition, and the BT composition is BisEDT. In some embodiments, the wound surface area of said wound is reduced by 50% 4 weeks after the first administration of the BisEDT composition. In some embodiments, the wound surface area is measured using digital photographs or hand measurements.

In some embodiments, the present disclosure provides a method for preventing amputation and/or infection-related surgery in a subject having a diabetic foot infection, comprising administering to the subject a therapeutically effective amount of a BT composition. In some embodiments, the BT composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for preventing amputation and/or infection-related surgery in a subject having a diabetic foot infection, the applied BT composition is present on the surface at a concentration from about 1 μg/$cm^2$ to about 1,000,000 μg/$cm^2$ (e.g. about 1 μg/$cm^2$ to about 10,000 μg/$cm^2$). In some embodiments, the applied BT composition is present on the surface at a concentration from about 50 μg/$cm^2$ to about 100 μg/$cm^2$. In some embodiments, the applied BT composition is present on the surface at a concentration greater than about 100 μg/$cm^2$ (e.g. as a dosage from about 250 μg/$cm^2$ to about 5,000 μg/$cm^2$).

In some embodiments, the present disclosure provides methods of treating a wound in a subject, wherein the wound is 30 days old or greater, comprising administering to the subject a therapeutically effective amount of a BT composition. In some embodiments, the subject has a diabetic foot infection. In some embodiments, the BT composition is a suspension of microparticles comprising BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, the present disclosure provides methods of treating a wound in a subject, wherein the wound is 30 days old or less, comprising administering to the subject a therapeutically effective amount of a BT composition. In some embodiments, the wound is a diabetic foot infection. In some embodiments, the BT composition is a suspension of microparticles comprising BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4. For example, the wound may be about 1 day old, about 2 days old, about 3 days old, about 4 days old, about 5 days old, about 6 days old, about 7 days old, about 8 days old, about 9 days old, about 10 days old, about 11 days old, about 12 days old, about 13 days old, about 14 days old, about 15 days old, about 16 days old, about 17 days old, about 18 days old, about 19 days old, about 20 days old, about 21 days old, about 22 days old, about 23 days old, about 24 days old, about 25 days old, about 26 days old, about 27 days old, about 28 days old, about 29 days old, or about 30 days old.

In some embodiments, of the methods of treating a wound in a subject, wherein the wound is 30 days old or greater, the applied BT composition is present on the surface at a concentration from about 1 μg/cm$^2$ to about 1,000,000 μg/cm$^2$ (e.g. about 1 μg/cm$^2$ to about 10,000 μg/cm$^2$). In some embodiments, the applied BT composition is present on the surface at a concentration from about 50 μg/cm$^2$ to about 100 μg/cm$^2$. In some embodiments, the applied BT composition is present on the surface at a concentration greater than about 100 μg/cm$^2$ (e.g. as a dosage from about 250 μg/cm$^2$ to about 5,000 μg/cm$^2$).

In some embodiments of the methods of treating a wound in a subject, wherein the wound is 30 days old or greater, the wound is greater than 2 months old, greater than 3 months old, greater than 4 months old, greater than 5 months old, greater than 6 months old, greater than 7 months old, greater than 8 months old, greater than 9 months old, greater than 10 months old, greater than 11 months old, or greater than 1 year old. In some embodiments, the wound is greater than 2 months old. In some embodiments, the wound is greater than 3 months old.

In some embodiments of the present disclosure, the BT composition described herein comprises BisEDT and the composition is a suspension of microparticles comprising said BisEDT compounds having a volumetric mean diameter (VMD) from about 0.4 μm to about 5 μm. In some embodiments, at least 70% of the microparticles have a VMD from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm. In some embodiments, the VMD is from about 0.4 μm to about 3 μm. In some embodiments, the VMD is from about 1.0 μm to about 2.0 μm. In some embodiments, at least 70%, 75%, 80%, 90%, or 95% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm. In some embodiments, at least 80% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm. In some embodiments, at least 90% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm. In some embodiments, substantially all of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm. In some embodiments, the VMD is from about 0.4 μm to about 3 μm. In some embodiments, the VMD is from about 1.0 μm to about 2.0 μm. In some embodiments, 90% of the particles are smaller than about 10 μm. For example, in some embodiments, 90% of the particles are smaller than about than about 10 μm, 9 μm, 8 μm, 7 μm, 6 μm, 5 μm, 4 μm, 3 μm, 2 μm, or about 1 μm.

BRIEF DESCRIPTION OF THE DRAWINGS

FIG. 1 shows that 2500 μg/mL BisEDT reduces wound titer by approximately five logs compared to diluent.

FIG. 2 shows that 2.5 mg/mL BisEDT completely inhibits spleen infection (≥4 fold log reduction) compared to diluent.

FIG. 3 shows that 10 mg/mL BisEDT reduced CFU by >8 logs (complete inhibition compared to untreated control) and 5 mg/mL BisEDT reduced CFU by 1.5-2 log.

FIG. 4 shows that 5 and 10 mg/mL BisEDT and Prontosan completely inhibit spleen CFU (≥3.5 log reduction) compared to untreated control.

FIG. 5A shows bioluminescent images of mice treated with BisEDT at 10 mg/mL, FIG. 5B shows bioluminescent images of mice treated with BisEDT at 5 mg/mL, FIG. 5C shows bioluminescent images of mice treated with BisEDT at 2.5 mg/mL, and FIG. 5D shows bioluminescent images of mice treated with BisEDT at 0.75 mg/mL. Bioluminescent images of mice treated with prontosan are shown in FIG. 5E and bioluminescence images of untreated mice are shown in FIG. 5F.

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the verb "comprise" as is used in this description and in the claims and its conjugations are used in its non-limiting sense to mean that items following the word are included, but items not specifically mentioned are not excluded. The present disclosure may suitably "comprise", "consist of", or "consist essentially of", the steps, elements, and/or reagents described in the claims.

Unless specifically stated or obvious from context, as used herein, the term "or" is understood to be inclusive. Unless specifically stated or obvious from context, as used herein, the terms "a", "an", and "the" are understood to be singular or plural.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

An "alkyl" group or "alkane" is a straight chained or branched non-aromatic hydrocarbon which is completely saturated. Typically, a straight chained or branched alkyl group has from 1 to about 20 carbon atoms, e.g. from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl can include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and can be represented by the general formula alkylS—.

The terms "amine" and "amino" are art-recognized and refer to both unsubstituted and substituted amines and salts thereof, e.g., a moiety that can be represented by

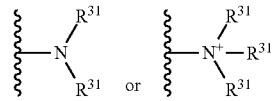

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aryl" as used herein include substituted or unsubstituted single-ring aromatic groups in which each atom of the ring is carbon. In some embodiments, the ring is a 5- to 7-membered ring, e.g. a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "bismuth" refers to the 83$^{rd}$ element of the periodic table, or atoms or ions thereof. Bismuth can occur in the metallic state or in the ionized state, such as in the III or V oxidation state. Bismuth ions can form complexes with anions, either to make bismuth salts, or to form complex anions which are then further complexed with one or more additional cation(s). Bismuth can also form covalent bonds to other atoms, such as sulfur.

As disclosed herein, a "bismuth-thiol compound" or "BT compound" is a compound that has a bismuth atom covalently bound to one, two or three other sulfur atoms present on one or more thiol compounds. The term "thiol" refers to a carbon-containing compound, or fragment thereof, containing an —SH group and can be represented by the general formula R—SH. These thiol compounds include compounds with one, two, three or more S atoms. Thiol compounds can have other functionality, such as alkyl, hydroxyl, carbocyclyl, heterocyclyl, aryl, heteroaryl, amino, and other substituents. Thiol compounds having two or more S atoms can chelate the bismuth atom, such that two S atoms from the same molecule covalently bond with the bismuth atom. Exemplary bismuth-thiol compounds are shown below:

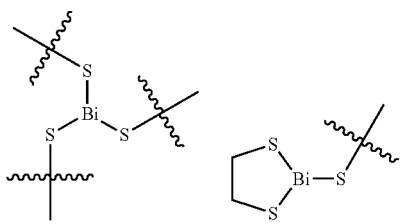

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle can be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle can be selected from saturated, unsaturated and aromatic rings. In an exemplary embodiment, an aromatic ring, e.g., phenyl, can be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" can be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl can be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl can be selected from saturated, unsaturated and aromatic rings. A "cycloalkenyl" group is a cyclic hydrocarbon containing one or more double bonds.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, for example 5- to 7-membered rings, e.g. 5- to 6-membered rings, whose ring structures include at least one heteroatom, for example one to four heteroatoms, e.g. one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, for example, 3- to 10-membered rings, more e.g. 3- to 7-membered rings, whose ring structures include at least one heteroatom, e.g. one to four heteroatoms, e.g. one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but can optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, for example, six or fewer. A "lower alkyl", for example, refers to an alkyl group that contains ten or fewer carbon atoms, e.g. six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, e.g. from 5 to 7.

The term "N-oxide" refers to a zwitterionic group containing a nitrogen atom in the +1 oxidation state bound to an oxygen atom in the −1 oxidation state. An non-limiting example of an N-oxide is pyridium N-oxide shown below. As used herein, the term "N-oxide" encompasses substituents of other groups having this functionality.

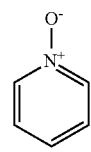

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen can have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "thioalkyl", as used herein, refers to an alkyl group substituted with a thiol group. A "thiol compound" as discussed above can include a thioalkyl as a substituent on the compound structure. A thiol compound can have, for example, one, two, three or more thioalkyl groups.

The term "thioether", as used herein, is equivalent to an ether, wherein the oxygen is replaced with a sulfur.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week.

"Coadministration" refers to the administration of the two agents in any manner in which the pharmacological effects of both agents are manifest in the patient at the same time. Thus, concomitant administration does not require that a single pharmaceutical composition, the same dosage form, or even the same route of administration be used for administration of both agents or that the two agents be administered at precisely the same time. However, in some situations, coadministration will be accomplished most conveniently by the same dosage form and the same route of administration, at substantially the same time.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more signs and symptoms of the disorder or condition relative to the untreated control sample.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "managing" includes therapeutic treatments as defined above. Managing includes achieving a steady state level of infection as determined by known methods in the art. The steady state can include evaluation of one or more of the severity of the infection(s), the size and location of the infection(s), the number of different microbial pathogens present in the infection(s), the level of antibiotic tolerant or resistant microbial pathogens, the degree of response to treatment, such as with a BT composition disclosed herein, the degree of biofilm formation and reduction, and the side effects experienced by the subject. During management of an infection, the infection may fluctuate from increasing to lessening in severity, in the amount or extent of infection, amount of side effects experienced by the subject, or other subject outcome indicia. Over a period of time, such as days, month, or years, the degree of management of the infection can be determined by evaluation of the above factors to assess whether the clinical course of infection has improved, is bacteriostatic, or has worsened. In some embodiments, managing an infection include successful treatment of microbial pathogen(s) that are otherwise drug tolerant or drug resistant.

The term "lessen the severity" of infection(s) refers to an improvement in the clinical course of the infection on any measurable basis. Such basis can include measurable indices such as reducing the extent of infection(s), whether the infection(s) are considered acute, the number and identity of microbial pathogens causing the infection(s), the extent/spread/amount of microbial (e.g. bacterial and/or fungal) biofilms, and side effects experienced by the subject. In some embodiments, lessening the severity of an infection is determined by measuring an improvement in clinical signs and symptoms of infection. In some embodiments, lessening the severity involves halting a steady decline in outcome to achieve stabilized infection(s), resulting in the subject entering successful management of the infection(s). In other embodiments, lessening the severity can result in substantial to complete treatment of the infection(s).

In some embodiments, lessening the severity of infections and/or symptoms can relate to patient-reported outcomes ("PROs"). A PRO instrument is defined as any measure of a subject's health status that is elicited from the patient and determines how the patient "feels or functions with respect to his or her health condition." PROs are particularly useful in reporting outcomes in DFI and whether the severity of symptoms has been reduced or lessened. Such symptoms can be observable events, behaviors, or feelings (e.g., ability to walk quickly, lack of appetite, expressions of anger), or unobservable outcomes that are known only to the patient (e.g., perceptions of pain, feelings of depression). In some embodiments, lessening the severity of infections and/or symptoms can be determined by physician assessments commonly known in the art, for example by an 8 item wound score.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of an infection.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

A "response" to a method of treatment can include, among other things, a decrease in or amelioration of negative signs and symptoms, a decrease in the progression of an infection or symptoms thereof, an increase in beneficial symptoms or clinical outcomes, a lessening of side effects, stabilization of the infection, and partial or complete remedy of infection, partial or full wound closure, reduction in wound size, or complete or substantially complete re-epithelialization, among others.

"Antibiotic susceptibility or sensitivity" refers to whether a bacteria will be successfully treated by a given antibiotic. Similarly, "Antifungal susceptibility or sensitivity" refers to whether a fungi will be successfully treated by a given antibiotic. Testing for susceptibility can be performed by methods known in the art such as the Kirby-Bauer method, the Stokes method and Agar Broth dilution methods. The effectiveness of an antibiotic in killing the bacteria or preventing bacteria from multiplying can be observed as areas of reduced or stable amount, respectively, of bacterial growth on a medium such as a wafer, agar, or broth culture.

"Antimicrobial tolerance" refers to the ability of a microbe, such as bacteria or fungi, to naturally resist being killed by antibiotics. It is not caused by mutant microbes but rather by microbial cells that exist in a transient, dormant, non-dividing state. Antibiotic or drug tolerance is caused by a small subpopulation of microbial cells termed persisters. Persisters are not mutants, but rather are dormant cells that can survive the antimicrobial treatments that kill the majority of their genetically identical siblings. Persister cells have entered a non- or extremely slow-growing physiological state which makes them insensitive (refractory or tolerant) to the action of antimicrobial drugs. Similarly, "antibiotic tolerance" refers to the ability of a bacteria to naturally resist being killed by antibiotics and "antifungal tolerance" refers to the ability of a fungi to naturally resist being killed by antibiotics.

"Antimicrobial resistance" refers to the ability of a microbe to resist the effects of medication that once could successfully treat the microbe. Microbes resistant to multiple antimicrobials are called multidrug resistant (MDR). Resistance arises through one of three mechanisms: natural resistance in certain types of bacteria, genetic mutation, or by one species acquiring resistance from another. Mutations can lead to drug inactivation, alteration of the drug's binding site, alteration of metabolic pathways and decreasing drug permeability.

As used herein, the term "in combination" or "in further combination" or "further in combination" refers to the use of an additional prophylactic and/or therapeutic agent as well as a BT composition of the present disclosure. The use of the term "in combination" does not restrict the order in which prophylactic and/or therapeutic agents are administered to a subject. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject.

As used herein, the terms "prophylactic agent" and "prophylactic agents" refer to an agent, such as a BT composition of the present disclosure, which can be used in the prevention, management, or control of one or more signs and symptoms of a disease or disorder, in particular, a disease or disorder associated with a microbial (e.g. bacterial and/or fungal) infection, such as diabetic foot infection.

As used herein, the terms "antibacterial activity", "antifungal activity" and "antimicrobial activity", with reference to a BT composition of the present disclosure, refers to the ability to kill and/or inhibit the growth or reproduction of a particular microorganism. In certain embodiments, antibacterial or antimicrobial activity is assessed by culturing bacteria, e.g., Gram-positive bacteria (e.g., *S. aureus*), Gram-negative bacteria (e.g., *A. baumannii*, *E. coli*, and/or *P. aeruginosa*) or bacteria not classified as either Gram-positive or Gram-negative, or fungi according to standard techniques (e.g., in liquid culture or on agar plates), contacting the culture with a BT composition of the present disclosure and monitoring cell growth after said contacting. For example, in a liquid culture, bacteria may be grown to an optical density ("OD") representative of a mid-point in exponential growth of the culture; the culture is exposed to one or more concentrations of one or more BT compounds of the present disclosure, or variants thereof, and the OD is monitored relative to a control culture. Decreased OD relative to a control culture is representative of antibacterial activity (e.g., exhibits lytic killing activity). Similarly, bacterial colonies can be allowed to form on an agar plate, the plate exposed to a BT composition of the present disclosure, or variants thereof, and subsequent growth of the colonies evaluated related to control plates. Decreased size of colonies, or decreased total numbers of colonies, indicate antibacterial activity.

"Biofilm" refers any syntrophic consortium of microorganisms in which cells stick to each other and often also to a surface. These adherent cells become embedded within a slimy extracellular matrix that is composed of extracellular polymeric substances (EPS). Upon formation of biofilms, microbial resistance to antibiotics is up to 1000 times greater compared to that of planktonic bacteria. Bacterial aggregates are clusters of laterally aligned cells can initiate biofilm development, which has a more complex and denser 3-D structure. In some embodiments, the biofilm may comprise one or more species of bacteria (e.g., *Pseudomonas aeruginosa* and *Staphylococcus aureus*) and/or one or more different phyla (e.g., bacteria, virus and fungi).

The term "infection" is used herein in its broadest sense and refers to any infection, such as viral infection or caused by a microorganism bacterial infection, fungal infection or parasitic infection (e.g. protozoa, amoeba or helminths). Examples of such infections can be found in a number of well-known texts such as "Medical Microbiology" (Greenwood, D., Slack, R., Peutherer, J., Churchill Livingstone Press, 2002); "Mims' Pathogenesis of Infectious Disease" (Mims, C., Nash, A., Stephen, J., Academic Press, 2000); "Fields" Virology. (Fields, B N, Knipe D M, Howley, P M, Lippincott Williams and Wilkins, 2001); and "The Sanford Guide To Antimicrobial Therapy," 26th Edition, JP Sanford et al. (Antimicrobial Therapy, Inc., 1996), which is incorporated by reference herein. The presence of infection in e.g. a diabetic foot wound is defined by clinical signs and symptoms of infection or inflammation, not by the culture of microorganisms, which are always present. However, immediately following resolution of clinical signs and symptoms of a wound infection, most patients will still have the underlying ulcer (e.g. diabetic foot ulcer), which requires continued treatment to facilitate complete wound closure. Of note, however, is that many wound specialists believe that in addition to the clinically defined state of infection, a less clinically apparent pathological state, known as "critical colonization" exists. In this state, a wound may be delayed or arrested in wound healing due to the subclinical presence of a high level of bacteria. This critical colonization, sometimes referred to as a high 'wound bioburden', is often polymicrobial and associated with biofilm-producing bacteria; it has been shown to induce, or prolong, the active inflammatory phase of repair, thus preventing a normal wound healing process. The bacterial cells that comprise such biofilms are difficult to recognize because they often exist in a viable, but nonculturable (VBNC), state (Pasquaroli 2013), yet they are adherent to surfaces and are typically more tolerant and resistant than their planktonic counterparts to antibiotics and antiseptics (Costerton 1999, Nguyen 2011). The term "infection" therefore contemplates the clinically defined state of infection as well as "critical colonization."

The term "wound closure" can encompass healing of a wound wherein sides of the wound are rejoined to form a continuous barrier (e.g., intact skin). In another embodiment, the compositions and methods provided herein promote tissue regeneration. In another embodiment, the compositions and methods provided herein limit scarring of tissues such as glia, tendons, eye tissue, ligament or skin. In some embodiments, "wound closure" refers to complete or substantially complete re-epithelialization. In some embodiments, "wound closure" occurs via secondary intention.

It is to be understood that the term "wound healing" can encompass a regenerative process with the induction of a temporal and spatial healing program comprising wound closure and the processes involved in wound closure. The term "wound healing" can also encompass the processes of granulation, neovascularization, fibroblast, endothelial and epithelial cell migration, extracellular matrix deposition, re-epithelialization, and remodeling. In some embodiments, "wound healing" refers to a wound remaining closed for a sufficient period of time after the initial wound closure (e.g. one day, two days, three days, four days, five days, six days, one week, two weeks, three weeks, or one month). In some embodiments, "wound healing" refers to a wound remaining closed for two weeks after the initial wound closure.

It will be appreciated by a skilled artisan that the term "granulation" can encompass the process whereby small, red, grainlike prominences form on a raw surface (that of wounds or ulcers) as healing agents. Granulation may also include the formation of granulation tissue over the wound. "Granulation tissue" refers to the newly growing tissue material at a wound site formed to heal the wound. The tissue is perfused, fibrous connective tissue including a variety of cell types. The tissue will grow generally from the base of the wound to gradually fill the entire wound space.

It will be appreciated by a skilled artisan that the term "neovascularization" can encompass the new growth of blood vessels with the result that the oxygen and nutrient supply is improved. Similarly, it will be appreciated by the skilled artisan that the term "angiogenesis" may encompass the vascularization process involving the development of new capillary blood vessels. It will also be appreciated that the term "cell migration" refers to the movement of cells (e.g., fibroblast, endothelial, epithelial, etc.) to the wound site.

It is to be understood that the term "extracellular matrix deposition" can encompass the secretion by cells of fibrous elements (e.g., collagen, elastin, reticulin), link proteins (e.g., fibronectin, laminin), and space filling molecules (e.g., glycosaminoglycans). It will be appreciated by the skilled artisan that the term "type I collagen" can encompass the most abundant collagen, which forms large well-organized fibrils having high tensile strength.

It will be appreciated by a skilled artisan that the term "re-epithelialization" can encompass the reformation of epithelium over a denuded surface (e.g., wound).

The term "remodeling" refers to the replacement of and/or devascularization of granulation tissue.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

As used herein, "D90" refers to the 90% value of particle diameter (i.e. the microparticle). For example if D90=1 μm, 90% of the particles are smaller than 1 μm. Similarly, "D80" refers to the 80% value of particle diameter (i.e. the microparticle), "D70" refers to the 70% value of particle diameter (i.e. the microparticle), "D60" refers to the 60% value of particle diameter (i.e. the microparticle), "D50" refers to the 50% value of particle diameter (i.e. the microparticle), "D40" refers to the 40% value of particle diameter (i.e. the microparticle), "D30" refers to the 30% value of particle diameter (i.e. the microparticle), "D20" refers to the 20% value of particle diameter (i.e. the microparticle), "D10" refers to the 10% value of particle diameter (i.e. the microparticle).

As used herein, MBN-101 refers to a composition comprising BisEDT.

METHODS OF USE

In some embodiments, the present disclosure provides methods for treating a topical wound, comprising administering to a subject in need thereof a therapeutically effective amount of a composition comprising a bismuth-thiol compound, wherein the composition is applied to the infection (e.g. applied to the surface of the infection).

Topical treatment provides the advantages of avoiding systemic adverse effects, providing increased target site concentration, and allowing the use of agents not available for systemic therapy. In some embodiments, mechanical debridement may be used to improve topical treatment because it reduces the bioburden of bacteria present and also opens a time-dependent therapeutic window for topical antimicrobial therapy (TAT) (Wolcott R D, et al. 2010. J Wound Care 19:320-328). Nevertheless, to date, no TAT agent has been proven to be effective for treating DFI (Nelson E A, et al. 2006. Diabet Med 23:348-359).

In some embodiments, the topical wound is a skin ulcer (e.g. a skin ulcer on a lower extremity). In some embodiments, the topical wound is a skin ulcer on a lower extremity, such as the leg and/or foot. In some embodiments, the skin ulcer is one or more of foot ulcer, ischemic ulcer, gangrenous ulcer, venous stasis ulcer, decubitus ulcer, Buruli ulcer, or traumatic ulcer. In some embodiments, the skin ulcer is a foot ulcer. In some embodiments, the topical wound is infected by one or more bacterial and/or fungal pathogens. In some embodiments, the topical wound is infected by bacterial pathogens. In some embodiments, the topical wound is a diabetic foot ulcer. In some embodiments, the diabetic foot ulcer is a diabetic foot infection. In some embodiments, the topical wound is infected with one or more of the following bacterial pathogens: *Staphylococcus aureus*, MIRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*.

Biofilms of *S. aureus* and other bacteria that are present in the wounds of DFI patients increase the difficulty of successful infection management and reduction. Combinations of DFI-relevant bacteria forming multispecies biofilms containing e.g. *S. aureus* have demonstrated greater resistance, virulence and pathogenicity than comparable single-species biofilms. The presence of such complex biofilms in the wounds of DFI patients is considered to be largely responsible for the chronic, persistent nature of these infections.

In some embodiments, the bacterial pathogen exhibits resistance to one or more antibiotics. Of particular concern are the methicillin-resistant *Staphylococcus aureus* strains (MRSA). MRSA remained an uncommon occurrence in hospital setting until the 1990's, when there was an explosion in MRSA prevalence in hospitals. MRSA now is considered endemic to hospitals, especially in the UK (Johnson A P et al. 2001 J. Antimicrobial Chemotherapy 48(1): 143-144). Moreover, MRSA presents a new threat in diabetic foot infections (Retrieved Jan. 17, 2009, from CDC: Centers for Disease Control and Prevention Web site). The ulcers and open sores that can occur in diabetic feet put patients at risk for contracting MRSA, and recent studies show evidence of MRSA impairing healing when present in the diabetic wound (Bowling F L, et al. 2009 Curr Diab Rep 9(6):440-444). See also, Kosinski, M A, et al. 2010. Expert Rev AntiInfect Ther. 8(11):1293-1305. In some embodiments, a bacterial pathogen is resistant to known standards of antibiotic care, including, but not limited to, amikacin, methicillin, vancomycin, nafcillin, gentamicin, metronidazole, Piperacillin/Tazobactam, ampicillin, chloramphenicol, doxycycline, tobramycin, levofloxacin, cephalosporins (e.g. cephalexin, cefoxitin, ceftizoxime, ceftibiprole, ceftazidime, ceftaroline), penicillin/ß-lactamase inhibitor combinations (e.g. amoxicillin/clavulanate, ampicillin/sulbactam, piperacillin/tazobactam, and ticarcillin/clavulanate), carbapenems (e.g. imipenem/cilastatin, ertapenem), fluoroquinolones (e.g. ciprofloxacin, moxifloxacin), clindamycin, linezolid, daptomycin, tigecycline, and vancomycin.

Long-term, repeated treatment with antibiotics to treat DFI-associated infections may result in development of antibiotic-resistance, characterized by the presence of microbial biofilms. Recent research has repeatedly demonstrated a correlation between multi-drug resistant (MDR) bacteria, and stronger, more prolific biofilm-forming capabilities. Bacteria within biofilms are protected from antibiotics, which increases the minimal inhibitory concentration of such antibiotics.

The BT compositions of the present disclosure have activity against a plurality of bacterial and fungal strains. In some embodiments, the BT compositions have activity against a plurality of strains including but not limited to *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*. Accordingly, some embodiments of the present disclosure provide methods of treating and/or preventing infections associated with *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., Clostridium spp., Peptococcus spp., Prevotella spp., Finegoldia spp., Propionibacterium acnes, S. dysgalactiae, Serratia spp., Rhodopseudomonas spp., Bacteroides fragilis, Morganella morganii, Hemophilus spp., Enterococcus spp., Stenotrophomonas spp., Pseudomonas spp., Stenotrophomonas maltophilia, Enterobacter cloacae, Sphingomonas sp., Acinetobacter spp., Anerococcus spp., Dialister spp., Peptoniphilus spp., Finegoldia magna, Peptoniphilus asaccharolyticus, Veillonella atypia, Anaerococcus vaginalis in both humans and animals using the BT compositions. In other aspects, the present disclosure provides methods of treating and/or preventing infections associated with related species or strains of these bacteria. In some embodiments, the bacterial infection is an infection associated with diabetic lower extremity infections, such as diabetic foot infections.

Staphylococcus aureus, MIRSA, Escherichia coli, Pseudomonas aeruginosa, Citrobacter spp., Klebsiella oxytoca, Proteus spp, Mobiluncus spp., Gardenella spp., Atopibium spp., S. epidermidis, Enterococcus faecalis, Coagulase-negative Staphylococcus spp., Streptococcus spp., Corynebacterium spp., Proteus mirabilis, Bacteroides spp., Peptostreptococcus spp., Propionibacterium spp., Clostridium spp., Peptococcus spp., Prevotella spp., Finegoldia spp., Propionibacterium acnes, S. dysgalactiae, Serratia spp., Rhodopseudomonas spp., Bacteroides fragilis, Morganella morganii, Hemophilus spp., Enterococcus spp., Stenotrophomonas spp., Pseudomonas spp., Stenotrophomonas maltophilia, Enterobacter cloacae, Sphingomonas sp., Acinetobacter spp., Anerococcus spp., Dialister spp., Peptoniphilus spp., Finegoldia magna, Peptoniphilus asaccharolyticus, Veillonella atypia, Anaerococcus vaginalis are responsible for many severe opportunistic infections, particularly in individuals with compromised immune systems, including diabetic patients. The pharmaceutical compositions of the present disclosure are contemplated for treating and/or preventing any infection associated with Staphylococcus aureus, MIRSA, Escherichia coli, Pseudomonas aeruginosa, Citrobacter spp., Klebsiella oxytoca, Proteus spp, Mobiluncus spp., Gardenella spp., Atopibium spp., S. epidermidis, Enterococcus faecalis, Coagulase-negative Staphylococcus spp., Streptococcus spp., Corynebacterium spp., Proteus mirabilis, Bacteroides spp., Peptostreptococcus spp., Propionibacterium spp., Clostridium spp., Peptococcus spp., Prevotella spp., Finegoldia spp., Propionibacterium acnes, S. dysgalactiae, Serratia spp., Rhodopseudomonas spp., Bacteroides fragilis, Morganella morganii, Hemophilus spp., Enterococcus spp., Stenotrophomonas spp., Pseudomonas spp., Stenotrophomonas maltophilia, Enterobacter cloacae, Sphingomonas sp., Acinetobacter spp., Anerococcus spp., Dialister spp., Peptoniphilus spp., Finegoldia magna, Peptoniphilus asaccharolyticus, Veillonella atypia, Anaerococcus vaginalis or associated with other species or strains of bacteria, including, but not limited to, infections of the skin, infections in and around wounds, chronic ulcers, ulcers associated with burn wounds, post-operative infections, infections associated with catheters and surgical drains, and infections of the blood. In some embodiments, the pharmaceutical compositions of the present disclosure find use in treating and/or preventing bacterial infections associated with areas of non-intact skin, including but not limited to, infections associated with cutaneous ulcers, such as diabetic foot ulcers, skin lesions, vesicles, cysts, blisters, bullae, open sores such as decubitus ulcers (bed sores) and other pressure sores, chronic ulcers, cellulitis and sores associated therewith, erysipelas and lesions associated therewith, wounds, burns and wounds associated therewith, carbuncles, or other conditions where the skin is damaged, cracked, broken, breached, and/or otherwise compromised.

In any of the embodiments described herein, the BT compositions may be used to treat an infection (e.g. DFI) of one or more of the following bacterial pathogens:

Acinetobacter baumanii
Acinetobacter junii
Anaerococcus lactolyticus
Anaerococcus vaginalis
Anaerococcus murdoch
Anaerococcus tetradius
Anaerococcus hydrogenalis
Actinobaculum massiliense
Actinobaculum schaalii
Actinomyces europaeus
Actinomyces hominis
Actinomyces neuii
Actinomyces radingae
Alcaligenes faecalis
Abiotrophia paraadiacens
Bacteroides fragilis
Bulleidia extructa
Bilophila wadsworthia
Campylobacter ureolyticus
Citrobacter murliniae
Clostridium saccharogumia
Clostridium novyi
Corynebacterium accolens
Corynebacterium amycolatum
Corynebacterium aurimucosum
Corynebacterium freiburgense
Corynebacterium hansenii
Corynebacterium jeikeium
Corynebacterium mycetoide
Corynebacterium simulans
Corynebacterium Tuberculostearicum
Corynebacterium xerosis
Corynebacterium striatum
Dermabacter hominis
Dialister invisus
Dialister propionicifaciens
Dialister micraerophilus
Dialister pneumosintes
Delftia acidovorans
Enterobacter aerogenes
Enterobacter cloacae
Enterobacter hormaechei
Enterococcus faecalis
Enterococcus canintestini
Echerichia coli
Escherichia fergusonii
Escherichia vulneris
Enterococcus avium
Enterococcus gallinarum
Enterococcus casseliflavus
Eggerthella lenta
Finegoldia magna
Fusobacterium canifelinum
Fusobacterium nucleatum
Fusobacterium periodontium
Granulicatella adiacens
Gemella morbillorum
Globicatella sanguinis
Haemophilus parainfluenzae
Haemophilus segnis
Helcococcus kunzii
Helcococcus kunzii

*Klebsiella oxytoca*
*Kocuria atrinae*
*Leclercia adecarboxylata*
*Mobiluncus curtisii*
*Moryella indoligenes*
*Morganella morganii*
*Negativicoccus succinicivorans*
*Peptoniphilus harei*
*Peptoniphilus gorbachii*
*Peptoniphilus ivorii*
*Peptoniphilus lacrimalis*
*Peptoniphilus olsenii*
*Peptoniphilus asaccharolyticus*
*Parvimonas micra*
*Peptococcus niger*
*Peptostreptococcus anaerobius*
*Peptostreptococcus stomatis*
*Porphyromonas asaccharolytica*
*Porphyromonas bennonis*
*Porphyromonas somerae*
*Porphyromonas uenonis*
*Porphyromonas levii*
*Prevotella timonensis*
*Prevotella bergensis*
*Prevotella buccalis*
*Prevotella corporis*
*Prevotella disiens*
*Prevotella intermedia*
*Prevotella nanceiensis*
*Pseudomonas indica*
*Pseudomonas otitidis*
*Psychrobacter lutiphocae*
*Proteus myxofaciens*
*Proteus hauseri*
*Providencia rettgeri*
*Providencia stuartii*
*Staphylococcus aureus*
*Staphylococcus epidermidis*
*Staphylococcus carnosus*
*Staphylococcus chromogenes*
*Staphylococcus devriesei*
*Staphylococcus hominis*
*Staphylococcus lugdunensis*
*Serratia nematodiphila*
*Stenotrophomonas maltophilia*
*Staphylococcus pettenkoferi*
*Staphylococcus capitis*
*Staphylococcus saprophyticus*
*Streptococcus agalactiae*
*Streptococcus anginosus*
*Streptococcus canis*
*Streptococcus dysgalactiae*
*Streptococcus infantarius*
*Streptococcus oralis*
*Serratia grimesii*
*Stenotrophomonas pavanii*
*Salmonella enterica*
*Trueperella bernardiae*
*Varibaculum cambriense*
*Veillonella atypica*
*Veillonella parvula*
*Veillonella dispar*
*Veillonella rogosae*
*Acinetobacter calcoaceticus*
*Acinetobacter lwoffii*
*Anaerococcus prevotii*
*Bacteroides caccae*
*Bacteroides distasonis*
*Bacteroides ovatus*
*Bacteroides stercoris*
*Bacteroides thetaiotaomicron*
*Bacteroides uniformis*
*Bacteroides vulgatus*
*Corynebacterium striatum*
*Clostridium innocuum*
*Clostridium perfringens*
*Clostridium ramosum*
*Pluralibacter gergoviae*
*Fusobacterium mortiferum*
*Finegoldia magna*
*Klebsiella oxytoca*
*Klebsiella pneumoniae*
*Pseudomonas aeruginosa*
*Peptococcus magnus*
*Prevotella bivia*
*Prevotella melaninogenica*
*Porphyromonas asaccharolytica*
*Peptostreptococcus asaccharolyticus*
*Peptostreptococcus micros*
*Parvimonas micra*
*Proteus mirabilis*
*Staphylococcus haemolyticus*
*Staphylococcus simulans*
*Staphylococcus saprophyticus*
*Streptococcus pneumoniae*
*Streptococcus agalactiae*
*Streptococcus mitis*
*Streptococcus milleri*
*Streptococcus dysgalactiae*
*Streptococcus canis*
*Serratia marcescens*
*Serratia liquefaciens*
*Stenotrophomonas maltophila*
*Epidermolysis bullosa*

In any of the embodiments described herein, the BT compositions may be used to treat an infection (e.g. DFI) of one or more of the following fungal pathogens: *Candida* spp., *Cladosporium* spp., *Aspergillus* spp., *Penicillium* spp., *Alternaria* spp., *Pleospora* spp., *Fusarium* spp, *Candida lusitaniae, Candida parapsilisis*, and *Candida albicans*.

In some embodiments, the BT compositions of the present disclosure find use in treating chronic ulcers. Chronic ulcers may arise from wounds caused by a variety of factors, especially in patients with impaired blood circulation, for example, caused by cardiovascular issues or external pressure from a bed or a wheelchair. More than 8 million patients are diagnosed with chronic skin ulcers each year in the United States alone (Harsha, A. et al., 2008, Journal of Molecular Medicine, 86(8): 961-969), which costs more than 10 billion dollars per year (Margolis, D J, et al., 2002, Journal of the American Academy of Dermatology 46(3): 381-386). Chronic ulcers may develop in the mouth, throat, stomach, and skin. Chronic skin ulcers include diabetic ulcers, venous ulcers, radiation ulcers, and pressure ulcers, the three major categories of chronic skin ulcers being diabetic ulcers, venous stasis ulcers, and pressure ulcers. Chronic ulcers can cause the loss of the integrity of large portions of the skin, even leading to morbidity and mortality.

In some embodiments, the BT compositions of the present disclosure find use in treating diabetic lower extremity infections, such as diabetic foot infections. Diabetic foot infection is one of the major complications of diabetes mellitus, occurring in about 15% of all diabetic patients and resulting in about 85% of all lower leg amputations. (Brem, et al., J. Clinical Invest., 2007, 117(5):1219-1222). Diabetes mellitus impedes the normal steps of the wound healing process, such that diabetic foot infections can become associated with non-healing, chronic cutaneous ulcers.

A chronic wound represents a failure of the normal processes of acute wound healing. Wound healing has traditionally been divided into three distinct phases: inflammation, proliferation and remodeling. The inflammatory phase of wound healing begins at the time of injury by forming a clot via a platelet plug, thereby initiating a response from neutrophils and macrophages. Neutrophils initially clear the wound of bacteria and debris by releasing a variety of proteases and reactive oxygen free radicals. Macrophages are then attracted to the wound site by chemoattractants and subsequently release their own chemoattractants to stimulate fibroblasts and more macrophages. During the proliferation phase, fibroblasts initiate epithelialization, angiogenesis, and collagenation. Epithelialization generally occurs from the basement membrane if it remains intact and from the wound margins if not intact. Fibroblasts synthesize type III collagen during this phase and transform into myofibroblasts, which help to stimulate wound contraction. During the remodeling phase, type III collagen begins to be replaced by type I collagen. Collagen is woven into an organized, cross-linked network whose strength approaches 80% of the original uninjured tissue.

There are many factors that can stall the three-phase healing process and convert an acute wound into a chronic wound. These may include a low proliferative capacity of the fibroblasts, downregulation of receptors, reduced growth factors, or the absence of a suitable protein matrix in the dermis. Further, poor perfusion and/or nutrition can cause a wound to halt in the inflammatory phase and lead to excessive build-up of exudate in the wound. A chronic ulcer can be considered to be a non-healing area of non-intact skin, such as an area of non-intact skin that fails to follow the normal processes of wound healing, e.g., as described above, and/or that fails to respond, or fails to respond appropriately, to initial treatment. A chronic ulcer on the skin may be characterized as a wound lesion lasting more than four weeks, without remarkable healing tendency or as a frequently recurrent wound (Fonder, M. et al., 2012, Journal of the American Academy of Dermatology 58(2): 185-206). A chronic wound may appear with red granulation and yellow pus, a dim purple skin around granular tissues, or gray-white and swelling granulation. Standard care procedures for chronic skin ulcer include, e.g., the following: removal of necrotic or infected tissue; establishment of adequate blood circulation; maintenance of a moist wound environment; management of wound infection; wound cleansing; and nutritional support, including blood glucose control for subjects with diabetic ulcers. For example, in the diabetic patient, poor control of blood glucose levels allows bacteria to grow more rapidly in a wound; further still, neural degeneration in diabetes means the condition may not be painful and thus go undetected, at least initially. Chronic ulcers, including diabetic foot ulcers, often become further infected with opportunistic bacteria, leading to exacerbation of the condition. *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis* are associated with such infections.

In some embodiments, the pharmaceutical composition of the present disclosure is formulated for use in methods of treating and/or preventing bacterial infections caused by *Staphylococcus aureus*, MIRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*. In some embodiments, the pharmaceutical composition of the present disclosure is formulated for use in methods of treating and/or preventing bacterial infections caused by *Staphylococcus aureus*, MIRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*. In some other embodiments, the pharmaceutical composition of the present disclosure is formulated for use in methods of treating and/or preventing bacterial infections caused by bacteria other than *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*.

In some embodiments, the present disclosure provides methods of treating and/or preventing chronic ulcers, comprising administering to a subject in need thereof a therapeutically or prophylactically effective amount of a pharmaceutical composition of the present disclosure. In some embodiments, administration comprises topical administration to the area of non-intact skin associated with the chronic ulcer. In some embodiments, topical administration follows debridement of the area to be treated In some embodiments, the present disclosure provides methods of treating and/or preventing diabetic foot infections, comprising administering to a subject in need thereof a therapeutically or prophylactically effective amount of a pharmaceutical composition of present disclosure. In some embodiments, administration comprises topical administration to the area of non-intact skin associated with the diabetic foot infection, e.g., a cutaneous ulcer. In some embodiments, topical administration follows debridement of the area to be treated.

Debridement can be accomplished by a number of approaches. Surgical debridement involves cutting away dead tissues of the wound or other area of non-intact skin. Mechanical debridement uses various methods to loosen and remove wound debris, such as a pressurized irrigation device, a whirlpool water bath, ultrasound, larval maggots, or specialized dressings. Autolytic debridement enhances the body's natural process of recruiting enzymes to break down dead tissue, for example, using an appropriate dressing that keeps the wound moist and clean. Enzymatic debridement uses chemical enzymes and appropriate dressings to further aid in the break down dead tissues at the site of a wound or other area of non-intact skin.

Debridement improves topical treatment because it reduces the bioburden of bacteria present and also opens a time-dependent therapeutic window for topical antimicrobial therapy (TAT) (Wolcott R D, et al. 2010. J Wound Care 19:320-328). Regarding the timing for debridement, early or immediate debridement is preferred to delayed debridement once this treatment option is chosen in the management of a wound. Further, multiple debridements during wound management may be indicated (Wolcott R D, et al. 2009. J Wound Care 18(2):54-6). For example, in some embodiments, debridement precedes topical application of a BT composition of the present disclosure, and is repeated before every administration of the BT composition. In some embodiments, debridement is performed only before every other administration of the BT composition, or only before every $3^{rd}$, $4^{th}$, $5^{th}$, or $6^{th}$ administration of the BT composition. In some embodiments, debridements are performed less frequently than the application of the BT composition, for example, once a week. Accordingly, if the BT composition is applied daily, the patient will not get debridement every time it is applied. In some embodiments, whether or not wound debridement is performed before topical administration of a BT composition of the present disclosure is within the clinical judgment of a health care practitioner treating the wound, e.g., the physician, physician's assistant, or emergency medical personnel.

The BT compositions of the present disclosure can find use in the treatment, management, control, and/or prevention of infections associated with chronic ulcers, including diabetic foot infections and cutaneous ulcers associated therewith. In other embodiments, BT compositions of the present disclosure find use in the treatment, management, control, and/or prevention of microbial (e.g. bacterial and/or fungal) infections associated with other areas of non-intact skin, such as a cellulitis sore, an erysipelas lesion, a decubitus ulcer, a burn wound, a traumatic wound, and a pressure sore. In some such embodiments, the composition used may be a topical composition, formulated for topical administration, e.g., for direct application to an area of non-intact skin, such as described above.

The BT compositions of the present disclosure also find use in the treatment, management, control, and/or prevention of decubitus ulcers. Decubitus ulcers, also called pressure sores or pressure ulcers, are injuries to the skin and underlying tissues resulting from prolonged pressure on the area. For example, bedsores most often develop on skin that covers bony areas of the body, such as the heel, ankles, hips or buttocks.

Bedsores fall into one of four stages based on their severity. Stage I is the beginning stage of a pressure sore while the skin still is intact. The skin may appear red, ashen, bluish or purple, and fails to blanch when touched. Stage II often involves an open wound of non-intact skin. At this stage, the outer layer of skin (epidermis) and part of the underlying layer of skin (dermis) has been damaged or lost. The ulcer may appear as a shallow, pinkish-red, basin-shaped wound. In Stage III, the ulcer is a deep wound, where the loss of skin may expose some amount of fat, and the ulcer has a crater-like appearance. The bottom of the wound also may have some yellowish dead tissue (slough). A Stage IV ulcer exhibits large-scale loss of tissue, where the wound may expose muscle, bone and tendons. The bottom of the wound will likely contain slough or dark, crusty, dead tissue (eschar).

As in the treatment of diabetic foot ulcers, debridement (e.g. of pressure ulcers or bedsores) may be used to remove damaged, dead, or infected tissue from the wound, facilitating proper healing, e.g., as described herein and/or otherwise known in the art. In some embodiments, administration of a pharmaceutical composition of the present disclosure follows debridement. For example, a pharmaceutical composition disclosed herein may be topically administered to a decubitus ulcer following surgical, mechanical, autolytic, or enzymatic debridement thereof.

BT compositions of the present disclosure also find use in the treatment, management, control, and/or prevention of cellulitis and/or erysipelas, including but not limited to sores and lesions associated with cellulitis and erysipelas. Cellulitis and erysipelas are skin infections that develop as a result of bacterial entry via breaches in the protective barrier of the skin. For example, cracks in the skin, cuts, blisters, burns, insect bites, spider bites, tattoos, surgical wounds, intravenous drug injection, or sites of intravenous catheter insertion may provide a means of entry for bacteria. Group A *Streptococcus* and *Staphylococcus* are the most common bacteria involved in cellulitis. Cellulitis is observed most frequently among middle-aged and elderly individuals, while erysipelas occurs in young children and the elderly (Ellis Simonsen S M et al. 2006. Epidemiol Infect. 134(2):293; and Eriksson B. et al. 1996 Clin Infect Dis 23:1091). Also, people with immune deficiency, diabetes, alcoholism, fungal infections, and impaired lymphatic drainage are at increased risk. Diabetics are especially prone to cellulitis in the feet, because the disease causes impairment of blood circulation in the legs. The lower extremities are the most common site of infection for both erysipelas and cellulitis (Ellis Simonsen S M et al. 2006. Epidemiol Infect. 134(2):293; Chartier C et al 1996 Int J Dermatol 35:779).

Cellulitis and erysipelas often coexist and generally manifest as areas of skin erythema, edema, and warmth. They differ in that erysipelas involves the upper dermis and superficial lymphatics, whereas cellulitis involves the deeper dermis and subcutaneous fat. Accordingly, erysipelas has more distinctive anatomic features than cellulitis-erysipelas lesions may be raised above the level of surrounding skin with a clear line of demarcation between involved and uninvolved tissue (Bisno A L et al. 1996 N Engl J Med 334:240). The lesion may appear red, swollen, warm, hardened, and/or as a rash similar in consistency to an orange peel. Erysipelas may appear on the face, for example, in a "butterfly" pattern. More severe infections can result in vesicles, bullae, and petechiae, with possible skin necrosis. In addition, patients with erysipelas tend to have acute onset of signs and symptoms with systemic manifestations, including fever and chills.

Patients with cellulitis tend to have a more gradual course of development, with signs and symptoms appearing over a few days' time. Various forms of cellulitis include periorbital cellulitis, abdominal wall cellulitis (in morbidly obese individuals), buccal cellulitis (due to *Streptococcus pneumoniae*), Ludwig's angina (cellulitis within the submandibular space), and perianal cellulitis (due to group A beta-hemolytic *streptococcus*) (Barzilai A, et al, 1998 Pediatr Infect Dis J. 17(4):358; Thorsteinsdottir B, et al. 2005 Scand J Infect Dis. 37(8):605). Cellulitis also can result in influenza-like signs and symptoms, with high temperatures and shaking.

In some embodiments, treatment of cellulitis or erysipelas further comprises administration of an antibiotic agent. For example, a pharmaceutical composition according to the present disclosure may be topically administered to an erysipelas lesion, in combination with an antibiotic agent selected from the group consisting of penicillin, clindamycin, and erythromycin. As another example, a pharmaceutical composition according to the present disclosure may be topically administered to a sore associated with cellulitis, in combination with an antibiotic agent selected from the group consisting of flucloxacillin, dicloxacillin, penicillins, ampicillin, and amoxicillin. The antibiotic may be administered orally, intravenously, or topically, e.g., along with topical administration of a BT composition of the present disclosure.

BT compositions of the present disclosure also find use in the treatment, management, control, and/or prevention of infections associated with burn wounds. A burn wound is any area of non-intact skin caused, directly or indirectly, from a burn. A burn is a type of injury to the skin that can be caused by heat, as well as electricity, chemicals, light, radiation or friction. Burns may affect only the skin (epidermal tissue), but in some cases also injure deeper tissues, such as muscle, bone, and blood vessels. Burns can be classified by mechanism of injury, depth, extent and associated injuries, and comorbidities. Burns conventionally are described based on the depth of injury to the dermis, being loosely classified as first, second, third, and fourth degree burns (Walls et al., 2009, Rosen's Emergency Medicine: Expert Consult Premium Edition (Rosen's Emergency Medicine: Concepts & Clinical Practice (2v)). Important characteristics of a burn wound include its cause (thermal, chemical, electrical), anatomic location, depth (full or partial thickness), duration, and extent (percent total body surface area). Patient characteristics that affect burn wound healing include age, nutritional status, underlying medical conditions, and concomitant injury (e.g., head trauma, inhalation injury, bone fractures).

Infections among burn patients are a major problem, with the reported incidence of nosocomial infections varying at 63-240 per 100 patient days and 53-93 per 1000 patient days, mainly depending on the definitions used (Chim H, et al, 2007, Burns 33:1008-1014; and Wibbenmeyer L, et al., 2006, J Burn Care Res 27:152-60). Moreover, bacterial infection of burn wounds are associated with adverse outcomes and mortality. In a series of 175 patients with severe burns, for example, infections preceded multiorgan dysfunction in 83% of patients and were considered the direct cause of death in 36% of patients who did not survive (Fitzwater J, et al., 2003, J Trauma 54:959-66). Burn wounds may become infected from multiple sources. Burn wounds may become initially infected with Gram positive bacteria, mainly staphylococci, that are normal deep inhabitants of the sweat glands and hair follicles exposed by the burn (Sharma B R., 2007, Infect Dis Clin North Am 21:745-59; ix). The moist, vascular burn eschar further may foster microbial growth. Gram negative bacterial infections may result from translocation from the colon, for example, due to reduced mesenteric blood flow at the time of burn and subsequent insults (Herndon D N, et al., 2000, Crit Care Med 28:1682-3). Furthermore, burn patients may develop immune deficits, including impaired cytotoxic T lymphocyte response, myeloid maturation arrest causing neutropenia, impaired neutrophil function, and decreased macrophage production (Sharma B R., 2007, Infect Dis Clin North Am 21:745-59, ix; Gamelli R L, et al., 2000, J Burn Care Rehabil 21:64-9; Hunt J P, et al., 1998, J Surg Res 80:243-51; and Shoup M, et al., 1998, Ann Surg 228:112-22). Finally, burn patients are susceptible to hospital acquired infections, common to other patients in intensive care units, including intravascular catheter related infections and ventilator associated pneumonia, with an overall incidence of infection higher than that of other patients in intensive care units (Chim H, et al., 2007, Burns 33:1008-14; and Wibbenmeyer L, et al., 2006, J Burn Care Res 27:152-60). Indeed, most episodes of bloodstream infection in burn patients after the first week are caused by hospital-type multidrug resistant bacteria (Wibbenmeyer L, et al., 2006, J Burn Care Res 27:152-60; and Ressner R A, et al., 2008, J Am Coll Surg 206:439-44).

Conventional treatment of burns includes debridement and excision, applying dressings the wound, wound closure, skin grafting, fluid resuscitation, management of wound infection such as administering antibiotics, pain control, nutritional support, and/or measures to inhibit excessive scar formation. A burn may be covered with a clean and dry sheet or dressing (such as cling film). Early cooling with cool water, within 30 minutes of the burn, reduces burn depth and pain. Debridement, cleaning, and dressings are important aspects of burn wound care.

In some embodiments, treatment of a burn wound further comprises administration of an antibiotic agent. It has been shown that antibiotic prophylaxis may reduce mortality, bacteraemia, and ventilator associated pneumonia among patients in intensive care units (Silvestri L, et al, 2007, J Hosp Infect 65:187-203; and De Smet A M, et al., 2009, N Engl J Med 360:20-31). In burns patients, the skin is an additional source of infection (Avni T, et al., 2010, BMJ 340: c241). In some embodiments, treatment of a burn wound further comprises administration of an agent for managing pain. A pharmaceutical composition according to the present disclosure may be topically administered to a burn wound, in combination with an agent for pain management selected from the group consisting of a simple analgesic, ibuprofen, acetaminophen, and a narcotic. The antibiotic agent and/or agent for managing pain may be administered orally, intravenously, or topically, e.g., along with topical administration of a BT composition of the present disclosure. One or more other aspects of conventional treatment of burns also may be used in combination with a BT composition of the present disclosure.

In some embodiments, the agent for pain management for use in combination with the BT composition of the present disclosure includes one or more agents selected from the group consisting of: paracetamol (acetaminophen), a non-steroidal anti-inflammatory drug, ibuprofen, ketoprofen, piroxicam, hydrocodone, morphine, hydromorphine, oxymorphone, fentanyl, oxycodone, diamorphine, methadone, buprenorphine, meperidine, pentazocine, dextromoramide, dipipanone, amitriptyline, dilaudid, tapentadol, and methadone. The agent for pain management may include any other agent for pain described herein and/or known in the art.

In some embodiments, the agent for pain management is one that can be applied topically, such as a topical anesthetic agent. A topical anesthetic agent is a local anesthetic agent that is used to numb the surface of a body part, such as any area of the skin, the front of the eyeball, the inside of the nose, ear or throat, the anus, or the genital area. In some embodiments, the agent for pain management for use in combination with a BT composition of the present disclosure includes one or more topical anesthetic agents selected from the group consisting of benzocaine, butamben, dibucaine, lidocaine, oxybuprocaine, pramoxine, prilocaine, proparacaine, proxymetacaine, and tetracaine (amethocaine). Topical anesthetic agents are available in creams, ointments, aerosols, sprays, lotions, and jellies. In further embodiments, the topical anesthetic agent may be used with one or more additional agents for pain management, such as another topical anesthetic agent, or a different agent for pain management, such as any other agent(s) for pain management described herein and/or known in the art.

BT compositions of the present disclosure will comprise a therapeutically and/or prophylactically effective amount of one of more BT compounds (e.g. BisEDT), as described herein. A therapeutically and/or prophylactically effective amount refers to an amount required to bring about a therapeutic and/or prophylactic benefit, respectively, in a subject receiving said amount. A therapeutically and/or prophylactically effective amount will depend on the particular formulation, route of administration, condition being treated, whether other agents or therapies are used in combination with methods of the present disclosure, and other factors.

In some embodiments of the methods for treating a topical wound, the subject experiences one or more of the following outcomes following the completion of dosing:

the wound is healed or substantially healed within 12 weeks of the first administration of the composition; and/or the prevention of amputation and/or infection-related surgery; and/or the wound is closed partially or fully; and/or the wound is reduced in size from about a 1% reduction relative to the original wound size to total elimination of the wound; and/or the wound is 30 days old or greater and is healed or substantially healed. In some embodiments, the subject experiences two or more of the recited outcomes. In some embodiments, the subject experiences three or more of the recited outcomes. In some embodiments, the subject experiences four or more of the recited outcomes. In some embodiments, the subject experiences all of the recited outcomes. In some embodiments of the methods for treating a topical wound, the subject experiences one or more of the following outcomes following the completion of dosing: less reinfection/relapse for the 12 weeks after start of treatment; resolution or improvement in signs and/or symptoms of infection that include redness, swelling, induration, exudate, pain, warmth (at site of infection) or fever; improved quality of life; eradication of insulting pathogens and/or biofilm; reduced need for concurrent systemic antibiotics.

In some embodiments, administration of a therapeutically effective amount of a BT composition, in accordance with the present disclosure, results in improved wound closure (partial or full), such as a reduction in the area of non-intact skin (wound area) compared to the area before initiation of treatment. Wound area can be expressed as a percentage of the initial wound area, at one or more time points after initiation of treatment. For example, in some embodiments, wound area decreases by at least about 20%, at least about 30%, at least about 40%, at least about 50%, at least about 60%, at least about 70%, at least about 80%; or at least about 90% over a course of treatment with a BT composition of the present disclosure. In some specific embodiments, the decrease in wound area occurs at least by day 1 after treatment initiation (t1), day 2 after treatment initiation (t2), day 3 after treatment initiation (t3), day 4 after treatment initiation (t4), day 5 after treatment initiation (t5), day 6 after treatment initiation (t6), day 7 after treatment initiation (t7), day 8 after treatment initiation (t8), day 9 after treatment initiation (t9), day 10 after treatment initiation (t10), day 12 after treatment initiation (t12), day 15 after treatment initiation (t15), day 20 after treatment initiation (t20), day 25 after treatment initiation (t25), or day 30 after treatment initiation (t30).

In some embodiments, administration of a therapeutically effective amount of a BT composition, in accordance with the present disclosure, results in improved wound healing, such as an improvement in ulcer grade based on the PEDIS classification compared to the ulcer grade before initiation of treatment. PEDIS is a routinely used, validated classification system for infections associated with wounds that has been developed by the International Working Group on the Diabetic Foot (IWGDF). IWGDF specifically developed a system for classifying wounds associated with diabetic foot infections that uses the acronym PEDIS, which stands for perfusion, extent (size), depth (tissue loss), infection, sensation (neuropathy). The classification originally was developed as a research tool (Schaper N C., 2004, Diabetes Metab Res Rev 20(Suppl 1):590-5), and offers a semi-quantitative gradation for the severity of each of the categories. Specifically, PEDIS Grade 1 corresponds to no symptoms or signs of infection; Grade 2 corresponds to a local infection involving only the skin and subcutaneous tissue (without involvement of deeper tissues and without systemic signs), while any erythema involved must be between 0.5 cm and 2 cm; Grade 3 corresponds to a local infection, as described for Grade 2, but involving an erythema of greater than 2 cm or involving structures deeper than skin and subcutaneous tissues (e.g., abscess, osteomyelitis, septic arthritis, fasciitis), but without any systemic inflammatory response signs; and Grade 4 corresponds to a local infection, as described for Grades 2 and 3, but with the signs of systemic inflammatory response syndrome, as manifested by more than two of the following: a temperature >38° C. or <36° C.; a heart rate >90 beats/min; a respiratory rate >20 breaths/min or partial pressure of arterial carbon dioxide <32 mm Hg; and a white blood cell count >12000 or <4000 cells/μL or >10% immature (band) forms (see, e.g., Lipsky, B A, et al., 2012, CID 54:e132-e173). Another classification system has been developed by the IDSA (the Infectious Diseases Society of America), which rates the infection severity of infected wounds, in particular, diabetic foot infections. Specifically, the IDSA rates PEDIS Grades 1-4 as "uninfected", "mild", "moderate", and "severe", respectively (see, again, Lipsky, B A, et al., 2012, CID 54:e132-e173).

In some embodiments, the PEDIS grade decreases from Grade 4 to Grade 3, Grade 2, or Grade 1, over a course of treatment with a BT composition of the present disclosure. In some embodiments, the PEDIS grade decreases from Grade 3 to Grade 2 or Grade 1, over a course of treatment with a BT composition of the present disclosure. In some embodiments, the PEDIS grade decreases from Grade 2 to Grade 1 over a course of treatment with a BT composition of the present disclosure. In some embodiments, the decrease in ulcer grade occurs by at least day 1 after treatment initiation (t1), day 2 after treatment initiation (t2), day 3 after treatment initiation (t3), day 4 after treatment initiation (t4), day 5 after treatment initiation (t5), day 6 after treatment initiation (t6), day 7 after treatment initiation (t7), day 8 after treatment initiation (t8), day 9 after treatment initiation (t9), day 10 after treatment initiation (t10), day 12 after treatment initiation (t12), day 15 after treatment initiation (t15), day 20 after treatment initiation (t20), day 25 after treatment initiation (t25), day 30 after treatment initiation (t30), day 35 after treatment initiation (t35), day 40 after treatment initiation (t40), day 45 after treatment initiation (t45), day 50 after treatment initiation (t50), day 55 after treatment initiation (t55), day 60 after treatment initiation (t60), day 65 after treatment initiation (t65), day 70 after treatment initiation (t70), day 75 after treatment initiation (t75), day 80 after treatment initiation (t80), or day 85 after treatment initiation (t85). In some embodiments, the decrease in ulcer grade occurs after day 85 after treatment initiation (t85+).

In some embodiments of the methods for treating a topical wound, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol and the composition is a suspension of microparticles comprising said BT compounds having a volumetric mean diameter (VMD) from about 0.4 µm to about 5 µm. In some embodiments, the BT compound is BisEDT.

In some embodiments of the methods for treating a topical wound, the BT composition comprises BisEDT and the applied BisEDT is present on the surface at a concentration greater than about 20 µg/cm$^2$. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for treating a topical wound, after administration of the BT composition, one or more of the following occurs: (i) reducing and or dispersing a microbial (e.g. bacterial and/or fungal) biofilm, (ii) impairing growth or formation of a microbial (e.g. bacterial and/or fungal) biofilm, and (iii) preventing reformation or spread of a microbial (e.g. bacterial and/or fungal) biofilm. In some embodiments, the BT composition treats, manages, and/or lessens the severity of the diabetic foot infection by one or both of: (i) prevention of the infection by the bacterial or fungal pathogen; and/or (ii) reduction of the bacterial or fungal pathogen. In some embodiments, the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm formation by the bacterial or fungal pathogen; (iv) inhibition of biofilm or microbial pathogen invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

BT compounds are known broad-spectrum antimicrobial (and anti-biofilm) small molecule drug products for the treatment of chronic, ultimately life-threatening infections. Its efficacy extends to Gram-positive (aerobic and anerobic), antibiotic-resistant pathogens including methicillin-resistant *Staphylococcus aureus* (MRSA, including community-associated [CA]-MRSA), methicillin-resistant *Staphylococcus epidermidis* (MRSE), and vancomycin-resistant *Enterococcus* (VRE). BT compounds are also potent against Multidrug-resistant (MDR) Gram-negative pathogens (aerobic and anerobic) including *Pseudomonas aeruginosa, Escherichia coli, Klebsiella pneumoniae* (including, in all of the afore-mentioned bacteria, carbapenem-resistant strains), and *Acinetobacter baumannii*.

BT compounds have the dual ability to overcome a) a very diversified spectrum of antibiotic resistance profiles (due to evolution/diversification driven by persistence, time and isolation in many different anatomical regions, and b) antibiotic-resistant and MDR biofilms.

In some embodiments, the infection contains one or more bacterial or fungal pathogens. In some embodiments, the disclosed methods comprise treating the DFI-related infection. In some embodiments, the disclosed methods comprise managing the DFI-related infection. In some embodiments, the disclosed methods comprise lessening the severity of the DFI-related infection.

In some embodiments, the bismuth-thiol composition comprises a plurality of microparticles that comprise a bismuth-thiol (BT) compound, substantially all of said microparticles having a volumetric mean diameter of from about 0.4 µm to about 5 µm, and wherein the BT compound comprises bismuth or a bismuth salt and a thiol-containing compound. In some embodiments, the bismuth salt is bismuth nitrate, bismuth subnitrate, or bismuth chloride. In some embodiments, the thiol-containing compound comprises one or more agents selected from 1,2-ethane dithiol, 2,3-dimercaptopropanol, pyrithione, dithioerythritol, 3,4 dimercaptotoluene, 2,3-butanedithiol, 1,3-propanedithiol, 2-hydroxypropanethiol, 1-mercapto-2-propanol, dithioerythritol, dithiothreitol and alpha-lipoic acid. In some embodiments, at least 70% of the microparticles have a volumetric mean diameter of from about 0.4 µm to about 3 µm, or from about 0.5 µm to about 2 µm, or from about 0.7 µm to about 2 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm, or any narrow ranges between the specific ranges described above.

In some embodiments, the BT composition comprises one or more BT compounds selected from bismuth-2,3-dimercaptopropanol (2:3 molar ratio, BisBAL)
bismuth-dithioerythritol (2:3 molar ratio, BisERY)
bismuth-4-methyl-1,2-benzenedithiol (2:3 molar ratio, BisTOL)
bismuth-2,3-butanedithiol (BisBDT)
bismuth-2,3-butanedithiol, 2-mercaptopyridine N-oxide (2:1:2 molar ratio, BisBDT/PYR)
bismuth-2,3-dimercaptopropanol, 2-mercaptopyridine N-oxide (2:1:2 molar ratio, BisBAL/PYR)

-continued bismuth-1,2-ethanedithiol, 2-mercaptopyridine N-oxide (2:1:2 molar ratio, BisEDT/PYR)
bismuth-4-methyl-1,2-benzenedithiol, 2-mercaptopyridine N-oxide (2:1:2 molar ratio, BisTOL/PYR)
bismuth-1,3-propanedithiol, 2-mercaptopyridine N-oxide (2:1:2 molar ratio, BisPDT/PYR)
bismuth-dithioerythritol, 2-mercaptopyridine N-oxide (2:1:2 molar ratio, BisERY/PYR)
bismuth-1-mercapto-2-propanol, 1,2-ethanedithiol (1:1:1 molar ratio, BisHPT/EDT)
bismuth with ethanedithiol and 2-mercaptobenzoimidazole (BisEDT/2MBI (1:1))
bismuth with ethanedithiol and 2-mercaptopyrimidine (BisEDT/SPN (2MPMD) (1:1))
bismuth with ethanedithiol and 3-mercapto-1,2,4-triazole (BisEDT/3MTZ (1:1))
bismuth with ethanedithiol and 1-propane thiol (BisEDT/PT (1:1))
bismuth with ethanedithiol and cysteamine (BisEDT/CSTMN (1:1))
bismuth with ethanedithiol and 3-mercaptopropionic acid (BisEDT/3MPA (1:1))
bismuth with lipoic acid (reduced) (BisALA (BisLipo) (1:1.5))
bismuth with 2-mercaptolpyridine N-oxide and 2-mercaptobenzoimidazole (BisPYR/2MBI (1:1))
bismuth with 2-mercaptolpyridine N-oxide and cysteamine (BisPYR/CSTMN (1:1))
bismuth with 2,3-dimercapto-1-propanol and 2-mercaptobenzoimidazole (BisBAL/2MBI (1:1))
bismuth with 2,3-dimercapto-1-propanol and cysteamine (BisBAL/CSTMN (1:1))
bismuth with 3,4 dimercapto toluene and 2-mercaptobenzoimidazole (BisTOL/2MBI (1:1))
bismuth with 3,4 dimercapto toluene and cysteamine (BisTOL/CSTMN (1:1))
bismuth with 2-mercapto pyridine (BisEDT/MPYR)

In some embodiments, the bismuth thiol compound is BisEDT, which has the following structure:

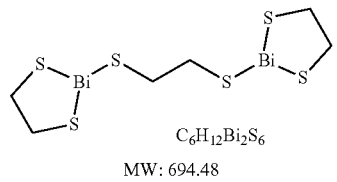

$C_6H_{12}Bi_2S_6$
MW: 694.48

In some embodiments of the methods for treating a topical wound, the administered BT composition is present on the surface at a concentration from about 1 µg/cm² to about 1,000,000 µg/cm² (e.g. about 1 µg/cm² to about 10,000 µg/cm²), including all integers and ranges therebetween. In some embodiments, the administered BT composition is present on the surface at a concentration from about 50 µg/cm² to about 200 µg/cm². In some embodiments, the applied BT composition is present on the surface at a concentration from about 250 µg/cm² to about 5,000 µg/cm². For example, in some embodiments, the bismuth thiol compound in the BT composition is BisEDT which is present on the surface at a concentration from about 1 µg/cm² to about 10,000 µg/cm² or from about 50 µg/cm² to about 200 µg/cm² or from about 250 µg/cm² to about 5,000 µg/cm². In some embodiments, the BT composition is present on the surface at a concentration of about 1 µg/cm², about 50 µg/cm², about 100 µg/cm², about 150 µg/cm², about 200 µg/cm², about 250 µg/cm², about 500 µg/cm², about 750 µg/cm², about 1000 µg/cm², about 1500 µg/cm², about 2000 µg/cm², about 2500 µg/cm², about 3000 µg/cm², about 3500 µg/cm², about 4000 µg/cm², about 4500 µg/cm², about 5000 µg/cm², about 5500 µg/cm², about 6000 µg/cm², about 6500 µg/cm², about 7000 µg/cm², about 7500 µg/cm², about 8000 µg/cm², about 8500 µg/cm², about 9000 µg/cm², about 9500 µg/cm², to about 10,000 µg/cm².

In some embodiments, the present disclosure provides methods of treating or preventing a bacterial infection in a subject in need thereof comprising administering to the subject a therapeutically effective amount of the pharmaceutical composition as described herein (e.g. a BisEDT-containing composition). In some embodiments, the bacterial infection is an infection by one or more of Staphylococcus aureus, MRSA, Escherichia coli, Pseudomonas aeruginosa, Citrobacter spp., Klebsiella oxytoca, Proteus spp, Mobiluncus spp., Gardenella spp., Atopibium spp., S. epidermidis, Enterococcus faecalis, Coagulase-negative Staphylococcus spp., Streptococcus spp., Corynebacterium spp., Proteus mirabilis, Bacteroides spp., Peptostreptococcus spp., Propionibacterium spp., Clostridium spp., Peptococcus spp., Prevotella spp., Finegoldia spp., Propionibacterium acnes, S. dysgalactiae, Serratia spp., Rhodopseudomonas spp., Bacteroides fragilis, Morganella morganii, Hemophilus spp., Enterococcus spp., Stenotrophomonas spp., Pseudomonas spp., Stenotrophomonas maltophilia, Enterobacter cloacae, Sphingomonas sp., Acinetobacter spp., Anerococcus spp., Dialister spp., Peptoniphilus spp., Finegoldia magna, Peptoniphilus asaccharolyticus, Veillonella atypia, Anaerococcus vaginalis. In some embodiments, the pharmaceutical composition is administered topically. In some embodiments, the subject is a mammal, e.g., a human. In some embodiments, the bacterial infection is diabetic foot infection. In some embodiments, the diabetic foot infection comprises a cutaneous ulcer. In some embodiments, the bacterial infection is associated with an area of non-intact skin selected from a sore associated with cellulitis, an erysipelas lesion, a burn wound, a chronic ulcer, a decubitus ulcer, and a pressure sore. In some embodiments, the treatment comprises topically administering the pharmaceutical composition to a cutaneous ulcer associated with diabetic foot infection. In some embodiments, administration follows mechanical debridement of the ulcer. In some embodiments, administration comprises use of at least one of a dressing, an instillation device, and a negative pressure wound therapy device.

In some embodiments of the methods for treating a topical wound, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the BT composition daily or weekly for a length of about 4 weeks to about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments of the methods for treating a topical wound, the wound area is from about 0.1 cm² to about 250 cm², including all integers and ranges therebetween. For example, the wound area may be about 0.1 cm², about 0.5 cm², about 1 cm², about 5 cm², about 10 cm², about 15 cm², about 20 cm², about 25 cm², about 30 cm², about 35 cm², about 40 cm², about 45 cm², about 50 cm², about 55 cm², about 60 cm², about 65 cm², about 70 cm², about 75 cm², about 80 cm², about 85 cm², about 90 cm², about 95 cm², about 100 cm², about 105 cm², about 110 cm² about 115 cm², about 120 cm², about 125 cm², about 130 cm², about 135 cm², about 140 cm² about 145 cm², about 150 cm², about 155 cm², about 160 cm², about 165 cm², about 170 cm², about 175 cm², about 180 cm², about 185 cm², about 190 cm², about 195 cm², about 200 cm², about 205 cm², about 210 cm², about 215 cm², about 220 cm², about 225 cm², about 230 cm², about 235 cm², about 240 cm², about 245 cm², or about 250 cm².

In some embodiments, the present disclosure provides methods for treating a bacterial infection, comprising administering to a subject in need thereof a therapeutically effective amount of a composition comprising a bismuth-thiol compound, wherein the composition is applied to the infection (e.g. applied to the surface of the infection). In some embodiments, the bacterial infection is a diabetic foot infection. In some embodiments, the bacterial infection comprises one or more of the following bacterial pathogens: *Staphylococcus aureus*, MRSA, *Escherichia coli, Pseudomonas aeruginosa, Citrobacter* spp., *Klebsiella oxytoca, Proteus* spp, *Mobiluncus* spp., *Gardenella* spp., *Atopibium* spp., *S. epidermidis, Enterococcus faecalis*, Coagulase-negative *Staphylococcus* spp., *Streptococcus* spp., *Corynebacterium* spp., *Proteus mirabilis, Bacteroides* spp., *Peptostreptococcus* spp., *Propionibacterium* spp., *Clostridium* spp., *Peptococcus* spp., *Prevotella* spp., *Finegoldia* spp., *Propionibacterium acnes, S. dysgalactiae, Serratia* spp., *Rhodopseudomonas* spp., *Bacteroides fragilis, Morganella morganii, Hemophilus* spp., *Enterococcus* spp., *Stenotrophomonas* spp., *Pseudomonas* spp., *Stenotrophomonas maltophilia, Enterobacter cloacae, Sphingomonas* sp., *Acinetobacter* spp., *Anerococcus* spp., *Dialister* spp., *Peptoniphilus* spp., *Finegoldia magna, Peptoniphilus asaccharolyticus, Veillonella atypia, Anaerococcus vaginalis.*

In some embodiments of the methods for treating a microbial (e.g. bacterial and/or fungal) infection, the infection is associated with a wound (e.g. an ulcer) and the subject experiences one or more of the following outcomes following the completion of dosing:

the wound is healed or substantially healed within 12 weeks (e.g. within 4 weeks) of the first administration of the composition; and/or the prevention of amputation and/or infection-related surgery; and/or the wound is closed partially or fully; and/or the wound is reduced in size from about a 1% reduction relative to the original wound size to total elimination of the wound; and/or the wound is 30 days old or greater and is healed or substantially healed. In some embodiments, the subject experiences two or more of the recited outcomes. In some embodiments, the subject experiences three or more of the recited outcomes. In some embodiments, the subject experiences four or more of the recited outcomes. In some embodiments, the subject experiences all of the recited outcomes.

In some embodiments of the methods for treating a microbial (e.g. bacterial and/or fungal) infection, the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol. In some embodiments, the BT compound is BisEDT. In some embodiments, the composition is a suspension of microparticles comprising said BT compounds having a volumetric mean diameter (VMD) from about 0.4 µm to about 5 µm. In some embodiments, at least 70% of the microparticles have a volumetric mean diameter of from about 0.4 µm to about 3 µm, or from about 0.5 µm to about 2 µm, or from about 0.7 µm to about 2 µm, or from about 0.8 µm to about 1.8 µm, or from about 0.8 µm to about 1.6 µm, or from about 0.9 µm to about 1.4 µm, or from about 1.0 µm to about 2.0 µm, or from about 1.0 µm to about 1.8 µm, or any narrow ranges between the specific ranges described above.

In some embodiments of the methods for treating a microbial (e.g. bacterial and/or fungal) infection, the BT composition comprises BisEDT and the applied BisEDT is present on the surface at a concentration greater than about 20 µg/cm².

In some embodiments of the methods for treating a microbial (e.g. bacterial and/or fungal) infection, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for treating a microbial (e.g. bacterial and/or fungal) infection, the method comprises at least one of: (i) reducing and or dispersing a microbial (e.g. bacterial and/or fungal) biofilm, (ii) impairing growth or formation of a microbial (e.g. bacterial and/or fungal) biofilm, and (iii) preventing reformation or spread of a microbial (e.g. bacterial and/or fungal) biofilm. In some embodiments, the BT composition treats, manages or lessens the severity of the diabetic foot infection by one or both of: (i) prevention of the infection by the bacterial or fungal pathogen; and (ii) reduction of the bacterial or fungal pathogen. In some embodiments, the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm or microbial pathogen formation by the bacterial or fungal pathogen; (iv) inhibition of biofilm invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

In some embodiments of the methods for treating a microbial (e.g. bacterial and/or fungal) infection, the applied BT composition is present on the surface at a concentration from about 1 µg/cm² to about 1,000,000 µg/cm² (e.g. about 1 µg/cm² to about 10,000 µg/cm²). In some embodiments, the applied BT composition is present on the surface at a concentration from about 50 µg/cm² to about 100 µg/cm². In some embodiments, the applied BT composition is present on the surface at a concentration from about 250 µg/cm² to about 5,000 µg/cm². For example, in some embodiments, the bismuth thiol compound in the BT composition is BisEDT which is present on the surface at a concentration from about 1 µg/cm² to about 10,000 µg/cm² or from about 50 µg/cm² to about 200 µg/cm² or from about 250 µg/cm² to about 5,000 µg/cm². In some embodiments, the BT composition is present on the surface at a concentration of about 1 µg/cm², about 50 µg/cm², about 100 µg/cm², about 150 µg/cm², about 200 µg/cm², about 250 µg/cm², about 500 µg/cm², about 750 µg/cm², about 1000 µg/cm², about 1500 µg/cm², about 2000 µg/cm², about 2500 µg/cm², about 3000 µg/cm², about 3500 µg/cm², about 4000 µg/cm², about 4500 µg/cm², about 5000 µg/cm², about 5500 µg/cm², about 6000 µg/cm², about 6500 µg/cm², about 7000 µg/cm², about 7500 µg/cm², about 8000 µg/cm², about 8500 µg/cm², about 9000 µg/cm², about 9500 µg/cm², to about 10,000 µg/cm².

In another embodiment, the dose volume may range from about 0.01 mL to about 10 mL or any range therein between. In another embodiment, the dose volume may range from about 0.1 mL to about 1 mL or any range therein between. In another embodiment, the minimal dose volume is about 0.1 mL to about 0.5 mL or any range therein between.

In some embodiments of the methods for treating a microbial (e.g. bacterial and/or fungal) infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the BT composition daily or weekly for a length of about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments of the methods for treating a microbial (e.g. bacterial and/or fungal) infection, the wound area is from about 0.1 cm² to about 250 cm². For example, the wound area may be about 0.1 cm², about 0.5 cm², about 1 cm², about 5 cm², about 10 cm², about 15 cm², about 20 cm², about 25 cm², about 30 cm², about 35 cm², about 40 cm², about 45 cm², about 50 cm², about 55 cm², about 60 cm², about 65 cm², about 70 cm², about 75 cm², about 80 cm², about 85 cm², about 90 cm², about 95 cm², about 100 cm², about 105 cm², about 110 cm², about 115 cm² about 120 cm², about 125 cm², about 130 cm², about 135 cm², about 140 cm², about 145 cm² about 150 cm², about 155 cm², about 160 cm², about 165 cm² about 170 cm², about 175 cm², about 180 cm², about 185 cm², about 190 cm², about 195 cm², about 200 cm², about 205 cm², about 210 cm², about 215 cm², about 220 cm², about 225 cm², about 230 cm², about 235 cm², about 240 cm², about 245 cm², or about 250 cm².

In some embodiments, the present disclosure provides methods for healing a wound in a subject having a diabetic foot infection, comprising administering the subject a therapeutically effective amount of a composition comprising BisEDT, wherein the composition is a suspension of microparticles comprising said BisEDT wherein at least 70% of the microparticles have a volumetric mean diameter (VMD) from about 0.4 µm to about 5 µm, and wherein the composition is applied to the infection (e.g. applied to the surface of the infection) and the wound is healed or substantially healed within 12 weeks of the first administration of the composition. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments of the methods for healing a wound in a subject having a diabetic foot infection, the applied BT composition is present on the surface at a concentration from about 1 µg/cm² to about 1,000,000 µg/cm² (e.g. about 1 µg/cm² to about 10,000 µg/cm²). In some embodiments, the applied BT composition is present on the surface at a concentration from about 50 µg/cm² to about 100 µg/cm². In some embodiments, the applied BT composition is present on the surface at a concentration greater than about 100 µg/cm² (e.g. as a dosage from about 250 µg/cm² to about 5,000 µg/cm²). For example, in some embodiments, the bismuth thiol compound in the BT composition is BisEDT which is present on the surface at a concentration from about 1 µg/cm² to about 10,000 µg/cm² or from about 50 µg/cm² to about 200 µg/cm² or from about 250 µg/cm² to about 5,000 µg/cm². In some embodiments, the BT composition is present on the surface at a concentration of about 1 µg/cm², about 50 µg/cm², about 100 µg/cm², about 150 µg/cm², about 200 µg/cm², about 250 µg/cm², about 500 µg/cm², about 750 µg/cm², about 1000 µg/cm², about 1500 µg/cm², about 2000 µg/cm², about 2500 µg/cm², about 3000 µg/cm², about 3500 µg/cm², about 4000 µg/cm², about 4500 µg/cm², about 5000 µg/cm², about 5500 µg/cm², about 6000 µg/cm², about 6500 µg/cm², about 7000 µg/cm², about 7500 µg/cm², about 8000 µg/cm², about 8500 µg/cm², about 9000 µg/cm², about 9500 µg/cm², to about 10,000 µg/cm².

In some embodiments of the methods for healing a wound in a subject having a diabetic foot infection, the BT composition is administered three times per day, two times per day, once daily, every other day, once every three days, three times per week, once every week, once every other week, once every month, or once every other month. In some embodiments, the wound is healed 4 weeks, 8 weeks or 12 weeks after the first administration of the BT composition. In some embodiments, the subject is administered multiple doses of the BT composition daily or weekly for a length of time ranging from about one week to about 12 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the BT composition daily or weekly for a length of about 4 weeks. In some embodiments, the subject is administered multiple doses of the BT composition daily or weekly for a length of about 4 weeks to about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments of the methods for healing a wound in a subject having a diabetic foot infection, the wound area is from about 0.1 $cm^2$ to about 250 $cm^2$. For example, the wound area may be about 0.1 $cm^2$, about 0.5 $cm^2$, about 1 $cm^2$, about 5 $cm^2$, about 10 $cm^2$, about 15 $cm^2$, about 20 $cm^2$, about 25 $cm^2$, about 30 $cm^2$, about 35 $cm^2$, about 40 $cm^2$, about 45 $cm^2$, about 50 $cm^2$, about 55 $cm^2$, about 60 $cm^2$, about 65 $cm^2$, about 70 $cm^2$, about 75 $cm^2$, about 80 $cm^2$, about 85 $cm^2$, about 90 $cm^2$, about 95 $cm^2$, about 100 $cm^2$, about 105 $cm^2$, about 110 $cm^2$, about 115 $cm^2$, about 120 $cm^2$, about 125 $cm^2$, about 130 $cm^2$, about 135 $cm^2$, about 140 $cm^2$, about 145 $cm^2$ about 150 $cm^2$ about 155 $cm^2$ about 160 $cm^2$ about 165 $cm^2$ about 170 $cm^2$ about 175 $cm^2$ about 180 $cm^2$, about 185 $cm^2$, about 190 $cm^2$, about 195 $cm^2$, about 200 $cm^2$, about 205 $cm^2$ about 210 $cm^2$, about 215 $cm^2$, about 220 $cm^2$, about 225 $cm^2$, about 230 $cm^2$, about 235 $cm^2$, about 240 $cm^2$, about 245 $cm^2$, or about 250 $cm^2$.

In some embodiments, the present disclosure provides methods for reducing the risk of amputation and/or infection-related surgery in a subject having a diabetic foot infection, comprising administering to the subject a therapeutically effective amount of a composition comprising BisEDT, wherein the composition is applied to the infection (e.g. applied to the surface of the infection) and the risk of amputation and/or infection-related surgery is reduced from about 1% to about 100% relevant to a similarly situated subject not treated with a therapeutically effective amount of a composition comprising a bismuth-thiol compound. In some embodiments, the composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for reducing the risk of amputation and/or infection-related surgery in a subject having a diabetic foot infection, the applied BT composition is present on the surface at a concentration from about 1 μg/$cm^2$ to about 1,000,000 μg/$cm^2$ (e.g. about 1 μg/$cm^2$ to about 10,000 μg/$cm^2$). In some embodiments, the applied BT composition is present on the surface at a concentration from about 50 μg/$cm^2$ to about 100 μg/$cm^2$. In some embodiments, the applied BT composition is present on the surface at a concentration greater than about 100 μg/$cm^2$ (e.g. as a dosage from about 250 μg/$cm^2$ to about 5,000 μg/$cm^2$). For example, in some embodiments, the bismuth thiol compound in the BT composition is BisEDT which is present on the surface at a concentration from about 1 μg/$cm^2$ to about 10,000 μg/$cm^2$ or from about 50 μg/$cm^2$ to about 200 μg/$cm^2$ or from about 250 μg/$cm^2$ to about 5,000 μg/$cm^2$. In some embodiments, the BT composition is present on the surface at a concentration of about 1 μg/$cm^2$, about 50 μg/$cm^2$, about 100 μg/$cm^2$, about 150 μg/$cm^2$, about 200 μg/$cm^2$, about 250 μg/$cm^2$, about 500 μg/$cm^2$, about 750 μg/$cm^2$, about 1000 μg/$cm^2$, about 1500 μg/$cm^2$, about 2000 μg/$cm^2$, about 2500 μg/$cm^2$, about 3000 μg/$cm^2$, about 3500 μg/$cm^2$, about 4000 μg/$cm^2$, about 4500 μg/$cm^2$, about 5000 μg/$cm^2$, about 5500 μg/$cm^2$, about 6000 μg/$cm^2$, about 6500 μg/$cm^2$, about 7000 μg/$cm^2$, about 7500 μg/$cm^2$, about 8000 μg/$cm^2$, about 8500 μg/$cm^2$, about 9000 μg/$cm^2$, about 9500 μg/$cm^2$, to about 10,000 μg/$cm^2$.

In some embodiments, of the methods for reducing the risk of amputation and/or infection-related surgery in a subject having a diabetic foot infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the BT composition daily or weekly for a length of about 4 weeks. In some embodiments, the subject is administered multiple doses of the BT composition daily or weekly for a length of about 4 weeks to about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments, of the methods for reducing the risk of amputation and/or infection-related surgery in a subject having a diabetic foot infection, the wound area is from about 0.1 $cm^2$ to about 250 $cm^2$. For example, the wound area may be about 0.1 $cm^2$, about 0.5 $cm^2$, about 1 $cm^2$, about 5 $cm^2$, about 10 $cm^2$, about 15 $cm^2$, about 20 $cm^2$, about 25 $cm^2$, about 30 $cm^2$, about 35 $cm^2$, about 40 $cm^2$, about 45 $cm^2$, about 50 $cm^2$, about 55 $cm^2$, about 60 $cm^2$, about 65 $cm^2$, about 70 $cm^2$, about 75 $cm^2$, about 80 $cm^2$, about 85 $cm^2$, about 90 $cm^2$, about 95 $cm^2$, about 100 $cm^2$, about 105 $cm^2$, about 110 $cm^2$, about 115 $cm^2$, about 120 $cm^2$, about 125 $cm^2$, about 130 $cm^2$, about 135 $cm^2$, about 140 $cm^2$, about 145 $cm^2$, about 150 $cm^2$, about 155 $cm^2$, about 160 $cm^2$, about 165 $cm^2$, about 170 $cm^2$, about 175 $cm^2$, about 180 $cm^2$, about 185 $cm^2$, about 190 $cm^2$, about 195 $cm^2$, about 200 $cm^2$, about 205 $cm^2$, about 210 $cm^2$, about 215 $cm^2$, about 220 $cm^2$, about 225 $cm^2$, about 230 $cm^2$, about 235 $cm^2$, about 240 $cm^2$, about 245 $cm^2$, or about 250 $cm^2$.

In some embodiments, the present disclosure provides methods for closing a wound in a subject having a diabetic foot infection, comprising administering to the subject a therapeutically effective amount of a composition comprising BisEDT. In some embodiments, the composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for closing a wound in a subject having a diabetic foot infection, the applied BT composition is present on the surface at a concentration from about 1 μg/$cm^2$ to about 1,000,000 μg/$cm^2$ (e.g. about 1 μg/$cm^2$ to about 10,000 μg/$cm^2$). In some embodiments, the applied BT composition is present on the surface at a concentration from about 50 μg/$cm^2$ to about 100 μg/$cm^2$. In some embodiments, the applied BT composition is present on the surface at a concentration greater than about 100 μg/$cm^2$ (e.g. as a dosage from about 250 μg/$cm^2$ to about 5,000 μg/$cm^2$). For example, in some embodiments, the bismuth thiol compound in the BT composition is BisEDT which is present on the surface at a concentration from about 1 μg/$cm^2$ to about 10,000 μg/$cm^2$ or from about 50 μg/$cm^2$ to about 200 μg/$cm^2$ or from about 250 μg/$cm^2$ to about 5,000 μg/$cm^2$. In some embodiments, the BT composition is present on the surface at a concentration of about 1 μg/$cm^2$, about 50 μg/$cm^2$, about 100 μg/$cm^2$, about 150 μg/$cm^2$, about 200 μg/$cm^2$, about 250 μg/$cm^2$, about 500 μg/$cm^2$, about 750 μg/$cm^2$, about 1000 μg/$cm^2$, about 1500 μg/$cm^2$, about 2000 μg/$cm^2$, about 2500 μg/$cm^2$, about 3000 μg/$cm^2$, about 3500 μg/$cm^2$, about 4000 μg/$cm^2$, about 4500 μg/$cm^2$, about 5000 μg/$cm^2$, about 5500 μg/$cm^2$, about 6000 μg/$cm^2$, about 6500 μg/$cm^2$, about 7000 μg/$cm^2$, about 7500 μg/$cm^2$, about 8000 μg/$cm^2$, about 8500 μg/$cm^2$, about 9000 μg/$cm^2$, about 9500 μg/$cm^2$, to about 10,000 μg/$cm^2$.

In some embodiments, of the methods for closing a wound in a subject having a diabetic foot infection, the composition is applied to the infection (e.g. applied to the surface of the infection) and the wound is closed within 12 weeks of the first administration of the composition. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the subject is administered multiple doses of the BT composition daily or weekly for a length of about 4 weeks. In some embodiments, the subject is administered multiple doses of the BT composition daily or weekly for a length of about 4 weeks to about 10 weeks. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments, of the methods for closing a wound in a subject having a diabetic foot infection, the wound area is from about 0.1 $cm^2$ to about 250 $cm^2$. For example, the wound area may be about 0.1 $cm^2$, about 0.5 $cm^2$, about 1 $cm^2$, about 5 $cm^2$, about 10 $cm^2$, about 15 $cm^2$, about 20 $cm^2$, about 25 $cm^2$, about 30 $cm^2$, about 35 $cm^2$, about 40 $cm^2$, about 45 $cm^2$, about 50 $cm^2$, about 55 $cm^2$, about 60 $cm^2$, about 65 $cm^2$, about 70 $cm^2$, about 75 $cm^2$, about 80 $cm^2$, about 85 $cm^2$, about 90 $cm^2$, about 95 $cm^2$, about 100 $cm^2$, about 105 $cm^2$, about 110 $cm^2$, about 115 $cm^2$, about 120 $cm^2$, about 125 $cm^2$, about 130 $cm^2$, about 135 $cm^2$, about 140 $cm^2$, about 145 $cm^2$ about 150 $cm^2$ about 155 $cm^2$ about 160 $cm^2$ about 165 $cm^2$ about 170 $cm^2$ about 175 $cm^2$ about 180 $cm^2$, about 185 $cm^2$, about 190 $cm^2$, about 195 $cm^2$, about 200 $cm^2$, about 205 $cm^2$ about 210 $cm^2$, about 215 $cm^2$, about 220 $cm^2$, about 225 $cm^2$, about 230 $cm^2$, about 235 $cm^2$, about 240 $cm^2$, about 245 $cm^2$, or about 250 $cm^2$.

In some embodiments, the present disclosure provides methods for wound size reduction in a subject having a diabetic foot infection, comprising administering to the subject a therapeutically effective amount of a composition comprising BisEDT, wherein the composition is applied to the infection (e.g. applied to the surface of the infection) and the wound is reduced in size from about a 1% reduction relative to the original wound size to total elimination of the wound within 12 weeks of the first administration of the composition. In some embodiments, the wound is reduced by about 10%, 20%, 30%, 40%, 50%, 60%, 70%, 80%, or 90%. In some embodiments, the wound is reduced by about 50%.

In some embodiments, of the methods for wound size reduction in a subject having a diabetic foot infection, the composition is a suspension of microparticles comprising said BisEDT wherein at least 70% of the microparticles have a volumetric mean diameter (VMD) from about 0.4 μm to about 5 μm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for wound size reduction in a subject having a diabetic foot infection, the applied BT composition is present on the surface at a concentration from about 1 μg/$cm^2$ to about 1,000,000 μg/$cm^2$ (e.g. about 1 μg/$cm^2$ to about 10,000 μg/$cm^2$). In some embodiments, the applied BT composition is present on the surface at a concentration from about 50 μg/$cm^2$ to about 100 μg/$cm^2$. In some embodiments, the applied BT composition is present on the surface at a concentration greater than about 100 μg/$cm^2$ (e.g. as a dosage from about 250 μg/$cm^2$ to about 5,000 μg/$cm^2$). For example, in some embodiments, the bismuth thiol compound in the BT composition is BisEDT which is present on the surface at a concentration from about 1 μg/$cm^2$ to about 10,000 μg/$cm^2$ or from about 50 μg/$cm^2$ to about 200 μg/$cm^2$ or from about 250 μg/$cm^2$ to about 5,000 μg/$cm^2$. In some embodiments, the BT composition is present on the surface at a concentration of about 1 μg/$cm^2$, about 50 μg/$cm^2$, about 100 μg/$cm^2$, about 150 μg/$cm^2$, about 200 μg/$cm^2$, about 250 μg/$cm^2$, about 500 μg/$cm^2$, about 750 μg/$cm^2$, about 1000 μg/$cm^2$, about 1500 μg/$cm^2$, about 2000 μg/$cm^2$, about 2500 μg/$cm^2$, about 3000 μg/$cm^2$, about 3500 μg/$cm^2$, about 4000 μg/$cm^2$, about 4500 μg/$cm^2$, about 5000 μg/$cm^2$, about 5500 μg/$cm^2$, about 6000 μg/$cm^2$, about 6500 μg/$cm^2$, about 7000 μg/$cm^2$, about 7500 μg/$cm^2$, about 8000 μg/$cm^2$, about 8500 μg/$cm^2$, about 9000 μg/$cm^2$, about 9500 μg/$cm^2$, to about 10,000 μg/$cm^2$.

In some embodiments, of the methods for wound size reduction in a subject having a diabetic foot infection, the BT composition is administered three times per day, two times per day, once daily, every other day, once every three days, three times per week, once every week, once every other week, once every month, or once every other month. In some embodiments, the BT composition is administered once daily or three times per week. In some embodiments, the subject is administered multiple doses of the BT composition daily or weekly for a length of time ranging from about one week to about 12 weeks. In some embodiments, the subject is administered multiple doses of the BT composition daily or weekly for a length of about 4 weeks. In some embodiments, the subject is administered multiple doses of the BT composition daily or weekly for a length of about 4 weeks to about 10 weeks. In some embodiments, the subject is administered multiple doses of the BT composition daily or weekly for a length of time longer than about 12 weeks. For example, about 4 months, about 5 months, about 6 months, about 7 months, about 8 months, about 9 months, about 10 months, about 11 months, or about 1 year. In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments, of the methods for wound size reduction in a subject having a diabetic foot infection, the wound area is from about 0.1 cm$^2$ to about 250 cm$^2$. For example, the wound area may be about 0.1 cm$^2$, about 0.5 cm$^2$, about 1 cm$^2$, about 5 cm$^2$, about 10 cm$^2$, about 15 cm$^2$, about 20 cm$^2$, about 25 cm$^2$, about 30 cm$^2$, about 35 cm$^2$, about 40 cm$^2$, about 45 cm$^2$, about 50 cm$^2$, about 55 cm$^2$, about 60 cm$^2$, about 65 cm$^2$, about 70 cm$^2$, about 75 cm$^2$, about 80 cm$^2$, about 85 cm$^2$, about 90 cm$^2$, about 95 cm$^2$, about 100 cm$^2$, about 105 cm$^2$, about 110 cm$^2$ about 115 cm$^2$, about 120 cm$^2$, about 125 cm$^2$, about 130 cm$^2$, about 135 cm$^2$, about 140 cm$^2$ about 145 cm$^2$, about 150 cm$^2$, about 155 cm$^2$, about 160 cm$^2$, about 165 cm$^2$, about 170 cm$^2$, about 175 cm$^2$, about 180 cm$^2$, about 185 cm$^2$, about 190 cm$^2$, about 195 cm$^2$, about 200 cm$^2$, about 205 cm$^2$, about 210 cm$^2$, about 215 cm$^2$, about 220 cm$^2$, about 225 cm$^2$, about 230 cm$^2$, about 235 cm$^2$ about 240 cm$^2$, about 245 cm$^2$, or about 250 cm$^2$. In some embodiments, the wound surface area of said wound is reduced by 50% 12 weeks after the first administration of the BT composition, and the BT composition is BisEDT. In some embodiments, the wound surface area of said wound is reduced by 50% 4 weeks after the first administration of the BisEDT composition. In some embodiments, the wound surface area is measured using digital photographs or hand measurements.

In some embodiments, the present disclosure provides a method for preventing amputation and/or infection-related surgery in a subject having a diabetic foot infection, comprising administering to the subject a therapeutically effective amount of a BT composition. In some embodiments, the BT composition is a suspension of microparticles comprising said BisEDT wherein at least 70% of the microparticles have a volumetric mean diameter (VMD) from about 0.4 µm to about 5 µm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, of the methods for preventing amputation and/or infection-related surgery in a subject having a diabetic foot infection, the applied BT composition is present on the surface at a concentration from about 1 µg/cm$^2$ to about 1,000,000 µg/cm$^2$ (e.g. about 1 µg/cm$^2$ to about 10,000 µg/cm$^2$). In some embodiments, the applied BT composition is present on the surface at a concentration from about 50 µg/cm$^2$ to about 100 µg/cm$^2$. In some embodiments, the applied BT composition is present on the surface at a concentration greater than about 100 µg/cm$^2$ (e.g. as a dosage from about 250 µg/cm$^2$ to about 5,000 µg/cm$^2$). For example, in some embodiments, the bismuth thiol compound in the BT composition is BisEDT which is present on the surface at a concentration from about 1 µg/cm$^2$ to about 10,000 µg/cm$^2$ or from about 50 µg/cm$^2$ to about 200 µg/cm$^2$ or from about 250 µg/cm$^2$ to about 5,000 µg/cm$^2$. In some embodiments, the BT composition is present on the surface at a concentration of about 1 µg/cm$^2$, about 50 µg/cm$^2$, about 100 µg/cm$^2$, about 150 µg/cm$^2$, about 200 µg/cm$^2$, about 250 µg/cm$^2$, about 500 µg/cm$^2$, about 750 µg/cm$^2$, about 1000 µg/cm$^2$, about 1500 µg/cm$^2$, about 2000 µg/cm$^2$, about 2500 µg/cm$^2$, about 3000 µg/cm$^2$, about 3500 µg/cm$^2$, about 4000 µg/cm$^2$, about 4500 µg/cm$^2$, about 5000 µg/cm$^2$, about 5500 µg/cm$^2$, about 6000 µg/cm$^2$, about 6500 µg/cm$^2$, about 7000 µg/cm$^2$, about 7500 µg/cm$^2$, about 8000 µg/cm$^2$, about 8500 µg/cm$^2$, about 9000 µg/cm$^2$, about 9500 µg/cm$^2$, to about 10,000 µg/cm$^2$.

In some embodiments, the present disclosure provides methods of treating a wound in a subject, wherein the wound is 30 days old or greater, comprising administering to the subject a therapeutically effective amount of a BT composition. In some embodiments, the subject has a diabetic foot infection. In some embodiments, the BT composition is a suspension of microparticles comprising BisEDT wherein at least 70% of the microparticles have a volumetric mean diameter (VMD) from about 0.4 µm to about 5 µm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In some embodiments, the present disclosure provides methods of treating a wound in a subject, wherein the wound is 30 days old or less, comprising administering to the subject a therapeutically effective amount of a BT composition. In some embodiments, the subject has a diabetic foot infection. In some embodiments, the BT composition is a suspension of microparticles comprising BisEDT having a volumetric mean diameter (VMD) from about 0.4 µm to about 5 µm. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4. For example, the wound may be about 1 day old, about 2 days old, about 3 days old, about 4 days old, about 5 days old, about 6 days old, about 7 days old, about 8 days old, about 9 days old, about 10 days old, about 11 days old, about 12 days old, about 13 days old, about 14 days old, about 15 days old, about 16 days old, about 17 days old, about 18 days old, about 19 days old, about 20 days old, about 21 days old, about 22 days old, about 23 days old, about 24 days old, about 25 days old, about 26 days old, about 27 days old, about 28 days old, about 29 days old, or about 30 days old.

In some embodiments, of the methods of treating a wound in a subject, wherein the wound is 30 days old or greater, the applied BT composition is present on the surface at a concentration from about 1 µg/cm$^2$ to about 1,000,000 µg/cm$^2$ (e.g. about 1 µg/cm$^2$ to about 10,000 µg/cm$^2$). In some embodiments, the applied BT composition is present on the surface at a concentration from about 50 µg/cm$^2$ to about 100 µg/cm$^2$. In some embodiments, the applied BT composition is present on the surface at a concentration greater than about 100 µg/cm$^2$ (e.g. as a dosage from about 250 µg/cm$^2$ to about 5,000 µg/cm$^2$). For example, in some embodiments, the bismuth thiol compound in the BT composition is BisEDT which is present on the surface at a concentration from about 1 µg/cm$^2$ to about 10,000 µg/cm$^2$ or from about 50 µg/cm² to about 200 µg/cm² or from about 250 µg/cm² to about 5,000 µg/cm². In some embodiments, the BT composition is present on the surface at a concentration of about 1 µg/cm², about 50 µg/cm², about 100 µg/cm², about 150 µg/cm², about 200 µg/cm², about 250 µg/cm², about 500 µg/cm², about 750 µg/cm², about 1000 µg/cm², about 1500 µg/cm², about 2000 µg/cm², about 2500 µg/cm², about 3000 µg/cm², about 3500 µg/cm², about 4000 µg/cm², about 4500 µg/cm², about 5000 µg/cm², about 5500 µg/cm², about 6000 µg/cm², about 6500 µg/cm², about 7000 µg/cm², about 7500 µg/cm², about 8000 µg/cm², about 8500 µg/cm², about 9000 µg/cm², about 9500 µg/cm², to about 10,000 µg/cm².

In some embodiments, of the methods of treating a wound in a subject, wherein the wound is 30 days old or less, the applied BT composition is present on the surface at a concentration from about 1 µg/cm² to about 1,000,000 µg/cm² (e.g. about 1 µg/cm² to about 10,000 µg/cm²). In some embodiments, the applied BT composition is present on the surface at a concentration from about 50 µg/cm² to about 100 µg/cm². In some embodiments, the applied BT composition is present on the surface at a concentration greater than about 100 µg/cm² (e.g. as a dosage from about 250 µg/cm² to about 5,000 µg/cm²). For example, in some embodiments, the bismuth thiol compound in the BT composition is BisEDT which is present on the surface at a concentration from about 1 µg/cm² to about 10,000 µg/cm² or from about 50 µg/cm² to about 200 µg/cm² or from about 250 µg/cm² to about 5,000 µg/cm². In some embodiments, the BT composition is present on the surface at a concentration of about 1 µg/cm², about 50 µg/cm², about 100 µg/cm², about 150 µg/cm², about 200 µg/cm², about 250 µg/cm², about 500 µg/cm², about 750 µg/cm², about 1000 µg/cm², about 1500 µg/cm², about 2000 µg/cm², about 2500 µg/cm², about 3000 µg/cm², about 3500 µg/cm², about 4000 µg/cm², about 4500 µg/cm², about 5000 µg/cm², about 5500 µg/cm², about 6000 µg/cm², about 6500 µg/cm², about 7000 µg/cm², about 7500 µg/cm², about 8000 µg/cm², about 8500 µg/cm², about 9000 µg/cm², about 9500 µg/cm², to about 10,000 µg/cm².

In some embodiments, of the methods of treating a wound in a subject, wherein the wound is 30 days old or greater, the wound is greater than 2 months old, greater than 3 months old, greater than 4 months old, greater than 5 months old, greater than 6 months old, greater than 7 months old, greater than 8 months old, greater than 9 months old, greater than 10 months old, greater than 11 months old, or greater than 1 year old. In some embodiments, the wound is greater than 2 months old. In some embodiments, the wound is greater than 3 months old.

In any of the embodiments of the methods described herein, the BT composition that is ultimately applied or administered to the subject has a concentration from about 1 µg/mL to about 1,000,000 µg/mL (e.g. about 1 µg/cm² to about 10,000 µg/cm²). In some embodiments, the BT composition has a concentration from about 50 µg/mL to about 100 µg/mL. In some embodiments, the applied BT the BT composition has a concentration from about 250 µg/mL to about 5,000 µg/mL. For example, in some embodiments, the bismuth thiol compound in the BT composition is BisEDT which has a concentration from about 1 µg/mL to about 10,000 µg/mL or from about 50 µg/mL to about 200 µg/mL or from about 250 µg/mL to about 5,000 µg/mL. In some embodiments, the BT composition has a concentration of about 1 µg/mL, about 50 µg/mL, about 100 µg/mL, about 150 µg/mL, about 200 µg/mL, about 250 µg/mL, about 500 µg/mL, about 750 µg/mL, about 1000 µg/mL, about 1500 µg/mL, about 2000 µg/mL, about 2500 µg/mL, about 3000 µg/mL, about 3500 µg/mL, about 4000 µg/mL, about 4500 µg/mL, about 5000 µg/mL, about 5500 µg/mL, about 6000 µg/mL, about 6500 µg/mL, about 7000 µg/mL, about 7500 µg/mL, about 8000 µg/mL, about 8500 µg/mL, about 9000 µg/mL, about 9500 µg/mL, to about 10,000 µg/mL. In some embodiments of the methods described herein, the BT composition that is ultimately applied or administered to the subject has a concentration greater than about 1,000,000 µg/mL.

In a specific embodiment, the present invention may be a pharmaceutical composition comprising bismuth-thiol (BT) composition that comprises BisEDT suspended therein, wherein the BT composition comprises a plurality of microparticles. In a specific embodiment, the D90 of said microparticles is less than or equal to 4.5 µm, or 4.0 µm, or 3.5 µm, or 3.0 µm, or 2.5 µm, or 2.0 µm, or 1.9 µm, or 1.8 µm, or m 1.7 µm, or 1.6 µm, or 1.5 µm or any ranges in between. In a specific embodiment, the D90 of said microparticles is less than or equal to 1.9 µm. In another specific embodiment, the D90 of said microparticles is less than or equal to 1.6 µm. In another specific embodiment, the D50 of said microparticles is less than or equal to 2.5 µm, or 2.0 µm, or 1.5 µm, or 1.3 µm, or 1.2 µm, or 1.1 µm, or 1.0 µm, or 0.9 µm, or 0.87 µm, or 0.72 µm or any ranges in between. In another specific embodiment, the D10 of said microparticles is less than or equal to 0.9 µm, or 0.8 µm, or 0.7 µm, or 0.6 µm, or 0.50 µm, or 0.40 µm, or 0.39 µm, or 0.38 µm, or 0.37 µm, or 0.36 µm, or 0.35 µm, or 0.34 µm, or 0.33 µm, or any ranges in between. In a specific embodiment, the pharmaceutical composition comprising bismuth-thiol (BT) composition comprises BisEDT suspended therein, wherein the BT composition comprises a plurality of microparticles, wherein the D90 of said microparticles is less than or equal to about 1.6 µm. In a specific embodiment, the BT composition comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7. In another specific embodiment, the compositions described above can be administered to a subject for treating a topical wound in a subject, or any specific methods described herein. In another specific embodiment, the compositions described above can be administered to a subject for treating a diabetic foot infection or diabetic foot ulcer. In a specific embodiment, the methods may include administering the compositions described above to a subject, wherein the subject experiences one or more of the following outcomes following the completion of dosing of said composition:
 a) the wound is healed or substantially healed within 12 weeks of the first administration of the composition; and/or
 b) the prevention of amputation and/or infection-related surgery; and/or
 c) the wound is closed partially or fully; and/or
 d) the wound is reduced in size from about a 1% reduction relative to the original wound size to total elimination of the wound; and/or
 e) the wound is 30 days old or greater and is healed or substantially healed.

Combination Treatments

In some embodiments, the present disclosure provides methods of treating and/or preventing diabetic foot infections comprising administering a BT composition of the present disclosure in combination with a standard and/or non-standard therapy for diabetic foot infections. Standard therapies for diabetic foot infections, including but not limited to cutaneous ulcers associated therewith, includes extracellular matrix replacement therapy (including the use of autologous cells), moist wound therapy, negative pressure wound therapy, arterial re-vascularization therapy, hyperbaric oxygen therapy, administration of an antimicrobial agent, administration of an antibiotic agent, topical oxygen therapy, photodynamic therapy, high energy acoustic shockwave therapy, ultrasound therapy, and administration of a growth factor (Blume et al. 2008 Diabetes Care 31: 631-636). In some embodiments, the therapy is negative pressure wound therapy. As used herein, the term "in combination" or "in further combination" or "further in combination" refers to the use of an additional prophylactic and/or therapeutic agent as well as a BT composition of the present disclosure.

The use of the term "in combination" does not restrict the order in which prophylactic and/or therapeutic agents are administered to a subject. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject.

In some embodiments, a BT composition of the present disclosure is administered topically, e.g., to the site of a diabetic foot ulcer, while an additional agent is administered systemically. For example, in some embodiments, a BT composition of the present disclosure is administered topically, e.g., to the site of a diabetic foot ulcer, while an antibiotic agent is administered systemically. In still more embodiments involving the treatment of diabetic foot ulcers, the systemically administered antibiotic agent has antibacterial activity against *Staphylococcus aureus*, MIRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*. In some embodiments, a BT composition of the present disclosure is administered topically, e.g., to the site of a diabetic foot ulcer, along with an additional agent, also being administered topically. For example, in some embodiments, a BT composition of the present disclosure is administered topically along with a growth factor, e.g., to the site of a diabetic foot ulcer.

In some embodiments, the method is used in combination with a standard therapy for diabetic foot infection, e.g., a standard therapy selected from the group consisting of extracellular matrix replacement therapy (including the use of autologous cells), moist wound therapy, negative pressure wound therapy, arterial re-vascularization therapy, hyperbaric oxygen therapy, administration of an antimicrobial agent, administration of an antibiotic agent, topical oxygen therapy, photodynamic therapy, high energy acoustic shockwave therapy, ultrasound therapy, and administration of a growth factor (Blume et al. 2008 Diabetes Care 31: 631-636). In some embodiments, the therapy is negative pressure wound therapy. In some embodiments, the moist wound therapy comprises use of an adhesive-backing film, a silicone-coated foam, a hydrogel, and/or a hydrocolloid. In some embodiments, the extracellular matrix replacement therapy comprises use of bio-engineered tissue. In some embodiments, administration of the antibiotic agent comprises systemic administration. In some embodiments, the growth factor is at least one selected from the group consisting of platelet-derived growth factor, granulocyte colony-stimulating factor, epidermal growth factor, fibroblast growth factor, nerve growth factor, and vascular endothelial growth factor. In some embodiments, administration of the growth factor comprises topical administration. In some embodiments, the method is used in combination with a non-standard therapy for diabetic foot infection, e.g., where diabetic foot infection is refractory to a standard therapy.

Extracellular matrix therapy is used in the treatment, management, control, and/or prevention of non-healing areas of non-intact skin, and is a standard therapy for diabetic foot ulcers. The synthesis of the extracellular matrix (ECM) is a key feature in wound healing, especially when there has been a significant loss of tissue. Extracellular matrix therapy is designed to reduce protease levels in wound fluids by providing a competitive substrate (collagen) for the proteases, thereby reducing proteolytic destruction of essential extracellular matrix (ECM) components and promotes healing. For example, ECM therapy may comprise administration of agents that reduce proteolytic destruction of fibronectin and/or platelet-derived growth factors (PDGFs); as well as reduce the synthesis of matrix metalloproteinases (MMPs), such as a mixture of metal cations. ECM therapy also may comprise administration of amelogenin, an ECM protein with biological activity in the regeneration and repair of skin (Romanelli M. 2010 Wounds—Clinical Review 6(2):47-52).

ECM therapy also may comprise use of bio-engineered tissue, e.g., to replace the lost ECM. Bio-engineered tissues, also called "skin-replacement products" or "skin substitutes", often comprise biologic matrices, either with or without living cells (Brian D L et al. 2011. Expert Rev Dermatol. 6(3):255-262). Most bio-engineered tissues can be divided into living tissue substitutes versus bioactive adjuncts. The bio-engineered tissue may look like a thin, circular piece of real skin and can be placed directly on an area of non-intact skin. While the precise mechanism of healing is not completely understood, it is believed that bioengineered tissues improve healing by filling the wound with extracellular matrix proteins, and possibly also expressing additional growth factors and cytokines that facilitate healing. Particular examples of bioengineered tissues used in the treatment of diabetic foot ulcers include Apligraf and Dermagraft, which are commercially available.

Arterial revascularization therapy (ART) also is used in the treatment, management, control, and/or prevention of non-healing areas of non-intact skin, and also is a standard therapy for diabetic foot ulcers. A preferred approach in treating diabetic foot infections includes the percutaneous method of ART, which involves percutaneous balloon angioplasty, possibly with stenting. Other revascularization approaches include aortoiliac reconstruction with aortofemoral bypass and femoral-popliteal-tibial bypass using the saphenous vein.

Hyperbaric oxygen therapy (HBOT) also is used in the treatment, management, control, and/or prevention of non-healing areas of non-intact skin, and also is a standard therapy for diabetic foot ulcers. HBOT refers to intermittent treatment of the entire body at greater than normal atmospheric pressures, often with increased oxygen content compared to that of normal air. For example, using a hyperbaric oxygen chamber, pressure may be increased up to two times normal atmospheric pressure. Also, the patient may be exposed to oxygen at a concentration of up to 100%. The increased pressure, combined with the increase in oxygen content, dissolves oxygen in the blood plasma, body cells, tissues, and fluids, which in turn aids the wound-healing process. It is believed that HBOT can stimulate the growth of new blood vessels to locations with reduced circulation, improving blood flow to areas with arterial blockage.

In some other embodiments, the present disclosure provides methods of treating and/or preventing diabetic foot infections comprising administering a BT composition of the present disclosure in combination with a non-standard therapy for diabetic foot infections. Non-standard therapies generally are used where the diabetic foot ulcer is refractory to one or more standard therapies.

In certain embodiments, compositions disclosed herein can be used alone or in combination with another type of therapeutic agent. In certain embodiments, the BT compound is administered locally during any surgery described herein and a systemic antibiotic is administered at regular intervals pre- or post-surgically. In some embodiments, the systemic antibiotic is administered prior to surgery.

In certain embodiments, compositions of the disclosure are administered in combination with one or more additional therapeutic agent(s) provides improved efficacy relative to each individual administration of the compound of the disclosure or the one or more additional therapeutic agent(s). In certain such embodiments, coadministration provides an additive or synergistic effect, wherein an additive effect refers to the sum of each of the effects of individual administration of the compound of the disclosure and the one or more additional therapeutic agent(s). In some embodiments, the subject receives conjoint administration of a therapy for another disease, disorder, or condition. In some embodiments, the other therapy is an immunosuppressive treatment.

Standard antibiotics that may be used with compositions of the present disclosure include, but are not limited to, amikacin, gentamicin, kanamycin, neomycin, netilmicin, paromomycin, rhodostreptomycin, streptomycin, tobramycin, apramycin, rifamycin, naphthomycin, mupirocin, geldanamycin, ansamitocin, carbacephems, imipenem, meropenem, ertapenem, faropenem, doripenem, panipenem/betamipron, biapenem, PZ-601, cephalosporins, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefteram, ceftibuten, ceftiofur, ceftiolene, ceftizoxime, ceftriaxone, cefoperazone, ceftazidime latamoxef, cefclidine, cefepime, cefluprenam, cefoselis, cefozopran, cefpirome, cefquinome, flomoxef, ceftobiprole, azithromycin, clarithromycin, dirithromycin, erythromycin, roxithromycin, aztreonam, pencillin and penicillin derivatives, actinomycin, bacitracin, colistin, polymyxin B, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, garenoxacin, gemifloxacin, stifloxacin, trovalfloxacin, prulifloxacin, acetazolamide, benzolamide, bumetanide, celecoxib, chlorthalidone, clopamide, dichlorphenamide, dorzolamide, ethoxyzolamide, furosemide, hydrochlorothiazide, indapamide, mafendide, mefruside, metolazone, probenecid, sulfacetamide, sulfadimethoxine, sulfadoxine, sulfanilamides, sulfamethoxazole, sulfasalazine, sultiame, sumatriptan, xipamide, tetracycline, chlortetracycline, oxytetracycline, doxycycline, lymecycline, meclocycline, methacycline, minocycline, rolitetracycline, methicillin, nafcillin, oxacilin, cloxacillin, vancomycin, teicoplanin, clindamycin, co-trimoxazole, flucloxacillin, dicloxacillin, ampicillin, amoxicillin and any combination thereof in amounts that are effective to additively or synergistically enhance the therapeutic and/or prophylactic effect of the composition for a given infection. In some embodiments, the methods of the present disclosure comprise coadministering to the subject an antibiotic selected from amikacin, tobramycin, gentamicin, piperacillin, mezlocillin, ticarcillin, imipenem, ciprofloxacin, ceftazidime, aztreonam, ticaricillin-clavulanate, dicloxacillin, amoxicillin, ticarcillin-clavulanate, trimethoprim-sulfamethoxazole, cephalexin, piperacillin-tazobactam, linezolid, daptomycin, vancomycin, metronidazole, clindamycin, colistin, tetracycline, levofloxacin, amoxicillin and clavulanic acid (Augmentin®), cloxacillin, dicloxacillin, cefdinir, cefprozil, cefaclor, cefuroxime, erythromycin/sulfisoxazole, erythromycin, clarithromycin, azithromycin, doxycycline, minocycline, tigecycline, imipenem, meripenem, colistimethate/Colistin®, methicillin, oxacillin, nafcillin, cabenicillin, azlocillin, piperacillin, dalbavancin, oritavancin, tedizolid, delafloxacin, and tazobactam (Zosyn®), cefepime, and meropenem.

In certain embodiments of the present disclosure, the therapeutic agents that can be coadministered with compounds of the disclosure, such as a bismuth-thiol compound, include known antibiotics. In some embodiments, the antibiotic is selected from methicillin, vancomycin, nafcillin, gentamicin, ampicillin, chloramphenicol, doxycycline, tobramycin, and levofloxacin. In some embodiments, the antibiotic is selected from tobramycin, imipenem, tetracycline, and minocycline. In some embodiments, the antibiotic is administered systemically after revision surgery. In some embodiments, the antibiotic is administered prior to revision surgery. The conjointly administered therapeutic agent, such as an antibiotic, can be administered with any suitable frequency and at any suitable dosage. Such dosage amount and frequency can be determined by those of ordinary skill in the art.

In certain embodiments, BT compounds of the disclosure can be conjointly administered with one or more other BT compounds of the disclosure. Moreover, such combinations can be conjointly administered with other therapeutic agents.

Pharmaceutical Compositions

In some embodiments, the BT composition comprises one or more BT compounds selected from BisBAL, BisEDT, Bis-dimercaprol, BisDTT, Bis-2-mercaptoethanol, BisDTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol. and the composition is a suspension of microparticles comprising said BT compounds having a volumetric mean diameter (VMD) from about 0.4 µm to about 5 μm. In some embodiments, the BT compound is BisEDT.

In some embodiments, at least 70% of the microparticles have a volumetric mean diameter of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm, or any narrow ranges between the specific ranges described above.

In some embodiments, the BT composition comprises BisEDT at a concentration greater than about 100 μg/mL. In some embodiments, the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

In certain embodiments, the BT composition is a suspension of one or more BT compounds in Tween (e.g. Tween 80) and/or in a buffer (e.g. sodium phosphate buffer). For example, in some embodiments, the BT composition is a suspension of one or more BT compounds in from about 0.1% Tween 80 to about 1.0% Tween 80, including all ranges therebetween. For example, the BT composition is a suspension of one or more BT compounds in about 0.1% Tween 80, about 0.2% Tween 80, about 0.3% Tween 80, about 0.4% Tween 80, about 0.5% Tween 80, about 0.6% Tween 80, about 0.7% Tween 80, about 0.8% Tween 80, about 0.9% Tween 80, or about 1% Tween 80. In some embodiments, the BT composition is a suspension of one or more BT compounds in about 0.5% Tween 80. In some embodiments, the BT composition is a suspension of one or more BT compounds in about 1.1% Tween 80, about 1.2% Tween 80, about 1.3% Tween 80, about 1.4% Tween 80, about 1.5% Tween 80, about 1.6% Tween 80, about 1.7% Tween 80, about 1.8% Tween 80, about 1.9% Tween 80, or about 2% Tween 80.

The BT compositions and methods of the present disclosure can be utilized to treat a subject in need thereof. In certain embodiments, the subject is a mammal such as a human, or a non-human mammal. When administered to subject, such as a human, the composition or the compound may be administered as a pharmaceutical composition comprising, for example, a compound of the disclosure and a pharmaceutically acceptable carrier. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, methyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols and sugar alcohols, such as glycerin, sorbitol, mannitol, xylitol, erythritol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances, including salts such as sodium chloride, employed in pharmaceutical formulations. In some embodiments, when such pharmaceutical compositions are for human administration, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as lyophile for reconstitution, powder, solution, syrup, injection or the like. The composition can also be present in a solution suitable for topical administration.

In some embodiments, the pharmaceutical compositions of the present disclosure are formulated for topical administration, e.g., to an area of non-intact skin. Non-intact skin can include, but is not limited to, skin lesions, vesicles, chronic ulcers, cysts, blisters, bullae, open sores such as decubitus ulcers (bed sores) and other pressure sores, cellulitis sores, erysipelas lesions, wounds, burn wounds, carbuncles, cutaneous ulcers, e.g., cutaneous ulcers associated with diabetic foot infections, or other conditions where the skin is damaged, broken, cracked, breached and/or otherwise compromised. Topical formulations generally include a sterile buffer, such as a sterile PBS, water, or saline buffer, or a sterile SM buffer. A variety of buffers may be used in the context of the present disclosure and will be readily apparent to a person having ordinary skill in the art. For example, in some embodiments, suitable buffers include sodium or potassium citrate, citric acid, phosphate buffers such as sodium phosphate, boric acid, sodium bicarbonate and various mixed phosphate buffers including combinations of $Na_2HPO_4$, $NaH_2PO_4$ and $KH_2PO_4$. In some embodiments, sodium phosphate buffer is used. In some embodiments, sodium citrate buffer is used. Accordingly, the formulation pH may vary from about 5 to about 10. In some embodiments, the formulation pH is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10. In some embodiments, the formulation pH is about 7.4.

In some embodiments, the BT composition is a suspension of one or more BT compounds in about 0.5% Tween 80 in sodium phosphate buffer at a pH of about 7.4. In some embodiments, the one or more BT compounds are present in the composition at a concentration ranging from about 100 μg/mL to about 1000 mg/mL including all integers and ranges therebetween. For example, in some embodiments, the one or more BT compounds are present in the composition at a concentration ranging from about 100 μg/mL, 200 μg/mL, 300 μg/mL, 400 μg/mL, 500 μg/mL, 600 μg/mL, 700 μg/mL, 800 μg/mL, 900 μg/mL, 1000 μg/mL, 10 mg/mL, 25 mg/mL, 50 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, 400 mg/mL, 425 mg/mL, 450 mg/mL, 475 mg/mL, 500 mg/mL, 525 mg/mL, 550 mg/mL, 575 mg/mL, 600 mg/mL, 625 mg/mL, 650 mg/mL, 675 mg/mL, 700 mg/mL, 725 mg/mL, 750 mg/mL, 775 mg/mL, 800 mg/mL, 825 mg/mL, 850 mg/mL, 875 mg/mL, 900 mg/mL, 925 mg/mL, 950 mg/mL, 975 mg/mL, to about 1000 mg/mL. In some embodiments, the one or more BT compounds are present in the composition at a concentration ranging from about 100 μg/mL to about 1000 μg/mL.

In some embodiments, the BT composition is a suspension of BisEDT in Tween (e.g. Tween 80) in a buffer (e.g. sodium phosphate buffer). In some embodiments, the BT composition is a suspension of BisEDT in about 0.5% Tween 80 in a sodium phosphate buffer at a pH of about 7.4.

For topical application to the skin, the pharmaceutical compositions of the present disclosure may be combined with one or a combination of carriers for topical formulations, which can include, but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, carbomer polymers such as carbomer homopolymers, carbomer copolymers, and Carbopol® polymers, and combinations thereof. Carbopol® polymers are polymers of acrylic acid cross-linked e.g., with polyalkenyl ethers or divinyl glycol. In some embodiments, the Carbopol® polymer is Carbopol® 71G, Carbopol® 971P, Carbopol® 974P, Carbopol® 980, Carbopol® 981, Carbopol® 5984, Carbopol® 934, Carbopol® 934P, Carbopol® 940, Carbopol® 941, and Carbopol® 1342.

Carriers for topical formulations may comprise semi-solid and/or gel-like vehicles, which may include a polymer thickener, water, preservatives, active surfactants, emulsifiers, and/or a solvent or mixed solvent system. U.S. Pat. No. 5,863,560 discloses a number of different carrier combinations that can aid in the exposure of skin to a medicament, and its contents are incorporated herein by reference. The carrier may or may not involve a controlled-release formulation, e.g., as disclosed in US 2008/0260697, the contents of which are incorporated herein by reference. In some embodiments, the carrier may or may not involve a viscous formulation, e.g., a gel, e.g., as disclosed in US 2009/0191254, the contents of which are incorporated herein by reference.

In some embodiments, topical pharmaceutical compositions of the present disclosure are provided in a hermetically sealed container. The container may a vial, syringe, tube, bottle, ampoule (e.g. blow-fill-seal polypropylene ampules), sachet, or the like; and may comprise or consist of glass, plastic, or other suitable material. Ampoules, for example, generally are produced industrially from short lengths of glass tubing, shaped by heating with gas torches and gravity. Computer vision techniques often are employed, e.g., for quality control. The filling and sealing of ampoules may be done by automated machinery. Blank ampoules can be purchased from scientific glass supply houses and sealed, e.g., with a small gas torch, preferably under inert atmospheres. In some embodiments, the container also may be filled with an inert gas, in addition to the pharmaceutical composition. In some embodiments, the composition is provided in an ampoule, or other suitable container, and transferred for use to a vehicle suitable for direct contact with non-intact skin, e.g., a patch, wipe, bandage, dressing, as described below.

The topical mode of delivery may include a smear (e.g. finger swipe or with an applicator), a spray, a foam, a bandage, a time-release patch, a liquid-absorbed wipe, and combinations thereof. In some embodiments, the compositions of the present disclosure are provided, either directly or in a carrier(s), in a patch, wipe, bandage, dressing, or other vehicle suitable for direct contact with the skin, in particular, non-intact skin.

In some embodiments, topical administration of a pharmaceutical composition of the present disclosure comprises use of a dressing. The pharmaceutical composition of the present disclosure may be incorporated into a dressing and/or applied separately along with the use of a dressing. A dressing promotes healing by keeping a wound moist, creating a barrier against infection, and/or keeping the surrounding skin dry.

In some embodiments, the dressing comprises a moist wound dressing. Moist wound therapy, comprising use of moist wound dressings, represents a standard therapy in the treatment and control of non-healing wounds, including diabetic foot ulcers, for example. In moist wound therapy, wounds are dressed with materials that offer protection from outside contaminants, prevent wound desiccation, and provide an environment conducive to wound closure. The degree of moisture in a wound is to be considered when treating a diabetic ulcer. High levels of exudate warrant the choice of a moisture-absorbing material, including but not limited to alginates, foams, collagen-alginate combinations, carboxymethylcellulose materials, or gauze. Low exudate and desiccated wounds generally respond well to hydrogels. Hydrogel sheets often comprise three-dimensional networks of cross-linked hydrophilic polymers. Amorphous hydrogels are similar in composition to hydrogel sheets but lack the cross-linking. The gel also may comprise additional ingredients, such as collagens, alginate, or complex carbohydrates.

Standard dressing care for the treatment of diabetic foot ulcers in the US is still the use of wet-to-dry or wet-to-moist saline gauze dressings. Alginate dressings often comprise calcium or calcium-sodium salts of natural polysaccharides derived from brown seaweed. When the alginate material comes into contact with sodium-rich wound exudates, an ion exchange takes place, producing a hydrophilic gel.

Additional dressing choices include but are not limited to films including adhesive-backing films, gels, and foams including silicone-coated foams, hydrocolloids, collagen-based dressings, absorbent polymers, and the like. Hydrocolloid dressings often comprise adhesive, absorbent, and elastomeric components. Carboxymethylcellulose, for example, is a common absorptive ingredient. Hydrofiber dressing also often comprise carboxymethylcellulose, for example, sodium carboxymethylcellulose. Foam dressings often comprise a polymer, often polyurethane, with small, open cells that are able to hold fluids. Some varieties of foam dressings have a waterproof film covering the top surface and may have an adhesive coating on the wound contact side or on the wound border. Film dressings often comprise a single thin transparent sheet of polyurethane coated on one side with an adhesive. The sheet is permeable to gases and water vapor but impermeable to wound fluids. Hydrofiber dressings often comprise sodium carboxymethylcellulose fibers. Collagen-based dressings often comprise purified collagen derived from bovine, porcine, equine, or avian sources. Collagen-based dressings are believed to aid wound healing e.g., by stimulating fibroblast production.

In some embodiments, topical administration of a pharmaceutical composition of the present disclosure comprises instillation. The pharmaceutical compositions of the present disclosure may be incorporated into an instillation and/or applied separately along with the use of an instillation. Instillation refers to administration by introduction of the fluid pharmaceutical composition gradually, e.g., drop by drop of the fluid. Typical instillation therapy instills fluid into a wound under a low positive pressure. Devices for use in instillation include, e.g., Kritter-type instillation catheters (see, e.g., Brent H. et al. 2005. Wounds 17(2):37-48). Techniques known in the art to improve instillation and distribution of the fluid include, but are not limited to, filling a wound with instillation fluid, applying porous wound fillers, and/or combining with negative pressure wound therapy.

In some embodiments, topical administration of a pharmaceutical composition of the disclosure comprises negative pressure wound therapy. Negative pressure wound therapy (NPWT) refers to use of reduced pressure in proximity to a wound, or other area of non-intact skin, to augment and/or accelerates the growth of new tissue. The therapy involves controlled application of sub-atmospheric pressure to the area, using a sealed wound dressing connected to a vacuum pump. "Negative pressure wound therapy" may also be referred to as "reduced pressure therapy" or "vacuum therapy". Typically, reduced pressure is applied to the area of non-intact skin through a porous pad. The porous pad will contain pores capable of distributing the reduced pressure to the area and/or channeling fluids drawn out.

A number of devices can be used in NPWT. NPWT devices often comprise a vacuum pump, drainage tubing, and/or a dressing set. The pump may be stationary or portable, rely on A C or battery power, and/or allow for regulation of the suction strength. The dressing sets may comprise foam or gauze dressing, e.g., to be placed on the wound, and an adhesive film drape for sealing the area. The drainage tubes may come in a variety of configurations depending on the dressings used or wound to be treated. Once the dressing is sealed, the vacuum pump can be set to deliver continuous or intermittent pressures, with levels of generally varying between −125 and −75 mmHg NPWT may be used for administration of a pharmaceutical composition of the present disclosure, e.g., where the NPWT device used allows for delivery of fluids, such as a fluid pharmaceutical composition. (See, e.g., Gerry R, et al. 2007. Ann Plast Surg 59(1):58-62).

Modes of administration described herein and/or known in the art may be used to deliver desired dosages of compositions of the disclosure and in accordance with suitable dosage regimens. Dosages and dosage regimens may vary depending on the particular formulation, route of administration, condition being treated, and other factors. Animal experiments may provide reliable guidance for the determination of effective doses in human therapy, e.g., as within the skill of the ordinary physician. Interspecies scaling of effective doses can be performed by one of ordinary skill in the art following the principles described, e.g., by Mordenti, J. et al. "The use of interspecies scaling in toxicokinetics" in Toxicokinetics and New Drug Development, Yacobi et al., Eds., Pergamon Press, New York 1989, pp 42-96.

The pharmaceutical compositions of the present disclosure can be administered according to a dosage regimen. In the treatment of chronic ulcers and diabetic foot infections, e.g., including but not limited to the treatment of cutaneous ulcers associated therewith, a first dosage regimen may be followed initially, e.g., during an induction phase, and a second dosage regimen may be followed after, e.g., during a maintenance phase. In some embodiments, an induction phase dosage regimen is followed over an initial about 12 hours of treatment, or over an initial about 18 hours, about 24 hours, about 36 hours, or about 48 hours. In some embodiments, the induction phase dosage regimen comprises administration of a pharmaceutical composition of the present disclosure about every hour, about every 2 hours, 4 hours, 6 hours, 8 hours, 10 hours, or 12 hours. In some embodiments, the induction phase dosage regimen comprises administration of a pharmaceutical composition of the present disclosure about every 4 hours or about every 6 hours, e.g., over an initial 24 hours. In some embodiments, the induction phase dosage regimen comprises administration of a pharmaceutical composition of the present disclosure once a day for the initial period (e.g. the first 2-4 weeks) following by a decrease in dose frequency, such as twice weekly, for the subsequent period (e.g. weeks 4-12). In some embodiments, the pharmaceutical composition is administered topically in accordance with an induction phase dosage regimen.

In some embodiments, the induction phase is followed by a maintenance phase, e.g., where a different dosage regimen may be followed. The maintenance phase may continue for a number of days, weeks, months, or longer, following initial treatment. In some embodiments, the maintenance phase continues for about 1, 2, 3, 4, 5, 6, or 7 days following the induction phase. In some embodiments, the pharmaceutical composition is administered for 2, 3, or 4 weeks; 2, 4, 6, 8, 10, or 12 months; or 2, 3, 4, 5 or more years. In still some embodiments, the pharmaceutical composition according to the present disclosure is administered chronically, e.g. for several years or over the life of the patient.

In some embodiments, the maintenance phase dosage regimen comprises administration of a pharmaceutical composition of the present disclosure at a lower frequency of doses compared to the induction phase dosage regimen. For example, in some embodiments, the pharmaceutical composition is administered about every 6 hours, 8 hours, 10 hours, 12 hours, 16 hours, 20 hours, 24 hours, 30 hours, 36 hours, 42 hours, or 48 hours. In some embodiments, the maintenance phase dosage regimen comprises administration of a pharmaceutical composition of the present disclosure about every 12 hours or about every 24 hours, e.g., for at least about 3 or 4 additional following the induction phase. In some embodiments, the pharmaceutical composition is administered topically in accordance with a maintenance phase dosage regimen. In some embodiments, the maintenance phase dosage regimen pharmaceutical composition is administered less frequently, for example 1, 2, or 3 times per week for at least about 3 or 4 additional following the induction phase.

The formulations may conveniently be presented in unit dosage form and can be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect.

Compositions can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions that can be dissolved in sterile water, or some other sterile injectable medium immediately before use.

Liquid dosage forms useful for topical administration include pharmaceutically acceptable emulsions, lyophiles for reconstitution, microemulsions, solutions, suspensions, gels, syrups and elixirs. In addition to the active ingredient, the liquid dosage forms can contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (such as cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the topical compositions can also include adjuvants such as wetting agents, emulsifying and suspending agents, and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound can be mixed under sterile conditions with a pharmaceutically acceptable carrier, and with any preservatives or buffers that can be required.

The ointments, pastes, creams and gels can contain, in addition to an active compound, one or more excipients or carriers, such as animal and vegetable fats, oils, waxes, paraffins, starch, tragacanth, cellulose derivatives, polyethylene glycols, silicones, bentonites, silicic acid, talc, polymers, salts, and zinc oxide, or mixtures thereof. In some embodiments, the BT composition is in the form of an aqueous solution. In some embodiments, the excipient comprises a salt selected from sodium chloride or potassium chloride. In some embodiments, the excipient comprises sodium chloride.

In some cases, in order to prolong the effect of a drug, it is desirable to slow the absorption of the drug. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally administered drug form is accomplished by dissolving or suspending the drug in an oil vehicle.

Actual dosage levels of the active ingredients in the pharmaceutical compositions can be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount can include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable dose of an active compound used in the compositions and methods of the disclosure will be that amount of the compound that is the lowest dose effective to produce a therapeutic effect. Such an effective dose will generally depend upon the factors described above.

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Embodiments

1. A method for treating a topical wound, comprising administering to a subject in need thereof a therapeutically effective amount of a composition comprising a bismuth-thiol compound, wherein the composition is applied to the infection.

2. The method of embodiment 1, wherein the topical wound is a skin ulcer (e.g. a skin ulcer on a lower extremity).

3. The method of embodiment 2, wherein the skin ulcer is one or more of foot ulcer, diabetic foot ulcer, ischemic ulcer, gangrenous ulcer, venous stasis ulcer, decubitus ulcer, Buruli ulcer, or traumatic ulcer.

4. The method of any one of embodiments 1-3, wherein the topical wound is infected by one or more bacterial and/or fungal pathogens.

5. The method of any of the preceding embodiments, wherein the topical wound is a diabetic foot ulcer.

6. The method of embodiment 5, wherein the diabetic foot ulcer is a diabetic foot ulcer infection.

7. The method of any of the preceding embodiments, wherein the topical wound is infected with one or more of the following bacterial pathogens: *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*.

8. The method of any of the preceding embodiments, wherein the subject experiences one or more of the following outcomes following the completion of dosing:
a) the wound is healed or substantially healed within 12 weeks of the first administration of the composition; and/or
b) the prevention of amputation and/or infection-related surgery; and/or
c) the wound is closed partially or fully; and/or
d) the wound is reduced in size from about a 1% reduction relative to the original wound size to total elimination of the wound; and/or
e) the wound is 30 days old or greater and is healed or substantially healed.

9. The method of embodiment 8, wherein the subject experiences two or more of the recited outcomes.

10. The method of embodiment 8, wherein the subject experiences three or more or four or more of the recited outcomes.

11. The method of embodiment 8, wherein the subject experiences all of the recited outcomes.

12. The method of any of the preceding embodiments, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

13. The method of embodiment 12, wherein the BT compound is BisEDT.

14. The method of any one of embodiment 1-12, wherein the composition is a suspension of microparticles comprising said BT compounds having a volumetric mean diameter (VMD) from about 0.4 μm to about 5 μm.

15. The method of any preceding embodiment, wherein the BT composition comprises BisEDT and the applied BisEDT is present on the surface at a concentration greater than about 20 μg/cm$^2$.

16. The method of any of the preceding embodiments, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

17. The method of any of the preceding embodiments, wherein after administration of the BT composition, one or more of the following occurs: (i) reducing and or dispersing a bacterial and/or fungal biofilm, (ii) impairing growth or formation of a bacterial and/or fungal biofilm, and (iii) preventing reformation or spread of a bacterial and/or fungal biofilm.

18. The method of any of the preceding embodiments, wherein the BT composition treats, manages, and/or lessens the severity of the diabetic foot infection by one or both of: (i) prevention of the infection by the bacterial or fungal pathogen; and/or (ii) reduction of the bacterial or fungal pathogen.

19. The method of any of the preceding embodiments, wherein the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm formation by the bacterial or fungal pathogen; (iv) inhibition of biofilm or microbial pathogen invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

20. The method of any of the preceding embodiments, wherein the administered BT composition is present on the surface at a concentration from about 1 μg/cm$^2$ to about 1,000,000 μg/cm$^2$.

21. The method of any of the preceding embodiments, wherein the administered BT composition is present on the surface at a concentration from about 50 μg/cm$^2$ to about 200 μg/cm$^2$.

22. The method of any of the preceding embodiments, wherein the applied BT composition is present on the surface at a concentration from about 250 μg/cm$^2$ to about 5,000 μg/cm$^2$.

23. The method of any of the preceding embodiments, wherein the BT composition is administered three times per day, two times per day, once daily, every other day, once every three days, three times per week, once every week, once every other week, once every month, or once every other month.

24. The method of embodiment 22, wherein the BT composition is administered once daily or three times per week.

25. The method of any of the preceding embodiments, wherein the subject is administered multiple doses of the BT composition daily or weekly for a length of time ranging from about one week to about 12 weeks.

26. The method of embodiment 25, wherein the subject is administered multiple doses of the BT composition daily or weekly for a length of about 4 weeks to about 10 weeks.

27. The method of any of the preceding embodiments, wherein the wound area is from about 0.1 cm$^2$ to about 250 cm$^2$.

28. A method for treating a microbial infection, comprising administering to a subject in need thereof a therapeutically effective amount of a composition comprising a bismuth-thiol compound, wherein the composition is applied to the infection.

29. The method of embodiment 28, wherein the microbial infection is a diabetic foot infection.

30. The method of embodiment 28 or embodiment 29, wherein the microbial infection comprises one or more of the following bacterial pathogens: *Staphylococcus aureus*, MRSA, *Escherichia coli*, *Pseudomonas aeruginosa*, *Citrobacter* spp., *Klebsiella oxytoca*, *Proteus* spp, *Mobiluncus* spp., *Gardenella* spp., *Atopibium* spp., *S. epidermidis*, *Enterococcus faecalis*, Coagulase-negative *Staphylococcus* spp., *Streptococcus* spp., *Corynebacterium* spp., *Proteus mirabilis*, *Bacteroides* spp., *Peptostreptococcus* spp., *Propionibacterium* spp., *Clostridium* spp., *Peptococcus* spp., *Prevotella* spp., *Finegoldia* spp., *Propionibacterium acnes*, *S. dysgalactiae*, *Serratia* spp., *Rhodopseudomonas* spp., *Bacteroides fragilis*, *Morganella morganii*, *Hemophilus* spp., *Enterococcus* spp., *Stenotrophomonas* spp., *Pseudomonas* spp., *Stenotrophomonas maltophilia*, *Enterobacter cloacae*, *Sphingomonas* sp., *Acinetobacter* spp., *Anerococcus* spp., *Dialister* spp., *Peptoniphilus* spp., *Finegoldia magna*, *Peptoniphilus asaccharolyticus*, *Veillonella atypia*, *Anaerococcus vaginalis*.

31. The method of any of embodiments 28-30, wherein the infection is associated with a wound (e.g. an ulcer) and the subject experiences one or more of the following outcomes following the completion of dosing:

a) the wound is healed or substantially healed within 12 weeks (e.g. within 4 weeks) of the first administration of the composition; and/or b) the prevention of amputation and/or infection-related surgery; and/or c) the wound is closed partially or fully; and/or d) the wound is reduced in size from about a 1% reduction relative to the original wound size to total elimination of the wound; and/or e) the wound is 30 days old or greater and is healed or substantially healed.

32. The method of embodiment 31, wherein the subject experiences two or more of the recited outcomes.

33. The method of embodiment 31, wherein the subject experiences three or more or four or more of the recited outcomes.

34. The method of embodiment 31, wherein the subject experiences all of the recited outcomes.

35. The method of any of embodiments 28-34, wherein the BT composition comprises one or more BT compounds selected from BisBAL, BisEDT, Bis-dimercaprol, BisDTT, Bis-2-mercaptoethanol, Bis-DTE, Bis-Pyr, Bis-Ery, Bis-Tol, Bis-BDT, Bis-PDT, Bis-Pyr/Bal, Bis-Pyr/BDT, BisPyr/EDT, Bis-Pyr/PDT, Bis-Pyr/Tol, Bis-Pyr/Ery, bismuth-1-mercapto-2-propanol, and Bis-EDT/2-hydroxy-1-propanethiol.

36. The method of embodiment 35, wherein the BT compound is BisEDT.

37. The method of any one of embodiments 28-36, wherein the composition is a suspension of microparticles comprising said BT compounds having a volumetric mean diameter (VMD) from about 0.4 μm to about 5 μm 38. The method of embodiment 36, wherein the BT composition comprises BisEDT and the applied BisEDT is present on the surface at a concentration greater than about 20 μg/cm$^2$.

39. The method of any of embodiments 28-38, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

40. The method of any of embodiments 28-39, wherein the method comprises at least one of: (i) reducing and or dispersing a bacterial and/or fungal biofilm, (ii) impairing growth or formation of a bacterial and/or fungal biofilm, and (iii) preventing reformation or spread of a bacterial and/or fungal biofilm.

41. The method of any of embodiments 28-40, wherein the BT composition treats, manages or lessens the severity of the diabetic foot infection by one or both of: (i) prevention of the infection by the bacterial or fungal pathogen; and (ii) reduction of the bacterial or fungal pathogen.

42. The method of any of embodiments 28-41, wherein the BT composition treats, manages or lessens the severity of the infection by one or more of: (i) prevention of elaboration or secretion of exotoxins from the bacterial or fungal pathogen; (ii) inhibition of cell viability or cell growth of planktonic cells of the bacterial or fungal pathogen; (iii) inhibition of biofilm or microbial pathogen formation by the bacterial or fungal pathogen; (iv) inhibition of biofilm invasiveness to underlying tissues (e.g. subcutaneous tissue); (v) inhibition of biofilm or microbial pathogen pathogenicity to underlying tissues (e.g. subcutaneous tissue); (vi) inhibition of biofilm viability or biofilm growth of biofilm-forming cells of the bacterial or fungal pathogen; and/or (vii) prevents the reformation of biofilm after debridement.

43. The method of any of embodiments 28-42, wherein the applied BT composition is present on the surface at a concentration from about 1 μg/cm$^2$ to about 1,000,000 μg/cm$^2$.

44. The method of any of embodiments 28-43, wherein the applied BT composition is present on the surface at a concentration from about 50 μg/cm$^2$ to about 100 μg/cm$^2$.

45. The method of any of embodiments 28-43, wherein the applied BT composition is present on the surface at a concentration from about 250 μg/cm$^2$ to about 5,000 μg/cm$^2$.

46. The method of any one of embodiments 28-45, wherein the BT composition is administered three times per day, two times per day, once daily, every other day, once every three days, three times per week, once every week, once every other week, once every month, or once every other month.

47. The method of embodiment 45, wherein the BT composition is administered once daily or three times per week.

48. The method of any of embodiments 28-47, wherein the subject is administered multiple doses of the BT composition daily or weekly for a length of time ranging from about one week to about 12 weeks.

49. The method of embodiment 48, wherein the subject is administered multiple doses of the BT composition daily or weekly for a length of about 10 weeks.

50. The method of any of embodiments 28-49, wherein the wound area is from about 0.1 cm$^2$ to about 250 cm$^2$.

51. A method for healing a wound in a subject having a diabetic foot infection, comprising administering the subject a therapeutically effective amount of a composition comprising BisEDT, wherein the composition is a suspension of microparticles comprising said BisEDT wherein at least 70% of the microparticles have a volumetric mean diameter (VMD) from about 0.4 μm to about 5 μm, and wherein the composition is applied to the infection and the wound is healed or substantially healed within 12 weeks of the first administration of the composition.

52. The method of embodiment 51, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

53. The method of embodiment 51 or embodiment 52, wherein the applied BT composition is present on the surface at a concentration from about 1 μg/cm$^2$ to about 1,000,000 μg/cm$^2$.

54. The method of any of embodiments 51-53, wherein the applied BT composition is present on the surface at a concentration from about 50 μg/$cm^2$ to about 100 μg/$cm^2$.

55. The method of any of embodiments 51-54, wherein the applied BT composition is present on the surface at a concentration greater than about 100 μg/$cm^2$ (e.g. as a dosage from about 250 μg/$cm^2$ to about 5,000 μg/$cm^2$).

56. The method of any one of embodiments 51-55, wherein the BT composition is administered three times per day, two times per day, once daily, every other day, once every three days, three times per week, once every week, once every other week, once every month, or once every other month.

57. The method of embodiment 51-56, wherein the wound is healed 4 weeks, 8 weeks or 12 weeks after the first administration of the BT composition.

58. The method of any of embodiments 51-57, wherein the subject is administered multiple doses of the BT composition daily or weekly for a length of time ranging from about one week to about 12 weeks.

59. The method of embodiment 58, wherein the subject is administered multiple doses of the BT composition daily or weekly for a length of about 4 weeks.

60. The method of any of embodiments 51-59, wherein the wound area is from about 0.1 $cm^2$ to about 250 $cm^2$.

61. A method for reducing the risk of amputation and/or infection-related surgery in a subject having a diabetic foot infection, comprising administering to the subject a therapeutically effective amount of a composition comprising BisEDT, wherein the composition is applied to the infection and the risk of amputation and/or infection-related surgery is reduced from about 1% to about 100% relevant to a similarly situated subject not treated with a therapeutically effective amount of a composition comprising a bismuth-thiol compound.

62. The method of embodiment 61, wherein the composition is a suspension of microparticles comprising said BisEDT and at least 70% of the microparticles have a volumetric mean diameter (VMD) from about 0.4 μm to about 5 μm.

63. The method of embodiment 61 or 62, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

64. The method of any one of embodiments 61-63, wherein the applied BT composition is present on the surface at a concentration from about 1 μg/$cm^2$ to about 1,000,000 μg/$cm^2$.

65. The method of any of embodiments 61-64, wherein the applied BT composition is present on the surface at a concentration from about 50 μg/$cm^2$ to about 100 μg/$cm^2$.

66. The method of any of embodiments 61-65, wherein the applied BT composition is present on the surface at a concentration greater than about 100 μg/$cm^2$ (e.g. as a dosage from about 250 μg/$cm^2$ to about 5,000 μg/$cm^2$).

67. The method of any one of embodiments 61-66, wherein the BT composition is administered three times per day, two times per day, once daily, every other day, once every three days, three times per week, once every week, once every other week, once every month, or once every other month.

68. The method of embodiment 67, wherein the BT composition is administered once daily or three times per week.

69. The method of any of embodiments 61-68, wherein the subject is administered multiple doses of the BT composition daily or weekly for a length of time ranging from about one week to about 12 weeks.

70. The method of embodiment 69, wherein the subject is administered multiple doses of the BT composition daily or weekly for a length of about 4 weeks.

71. The method of any of embodiments 61-70, wherein the wound area is from about 0.1 $cm^2$ to about 250 $cm^2$.

72. A method for closing a wound in a subject having a diabetic foot infection, comprising administering to the subject a therapeutically effective amount of a composition comprising BisEDT.

73. The method of embodiment 72, wherein the composition is a suspension of microparticles comprising said BisEDT wherein at least 70% of the microparticles have a volumetric mean diameter (VMD) from about 0.4 μm to about 5 μm.

74. The method of embodiment 72 or 73, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

75. The method of any one of embodiments 72-74, wherein the applied BT composition is present on the surface at a concentration from about 1 μg/$cm^2$ to about 1,000,000 μg/$cm^2$.

76. The method of any of embodiments 72-75, wherein the applied BT composition is present on the surface at a concentration from about 50 μg/$cm^2$ to about 100 μg/$cm^2$.

77. The method of any of embodiments 72-76, wherein the applied BT composition is present on the surface at a concentration greater than about 100 μg/$cm^2$ (e.g. as a dosage from about 250 μg/$cm^2$ to about 5,000 μg/$cm^2$).

78. The method of embodiment 77, wherein the composition is applied to the infection and the wound is closed within 12 weeks of the first administration of the composition.

79. The method of embodiment 78, wherein the BT composition is administered once daily or three times per week.

80. The method of any of embodiments 72-79, wherein the subject is administered multiple doses of the BT composition daily or weekly for a length of time ranging from about one week to about 12 weeks.

81. The method of embodiment 80, wherein the subject is administered multiple doses of the BT composition daily or weekly for a length of about 4 weeks.

82. The method of any of embodiments 72-81, wherein the wound area is from about 0.1 $cm^2$ to about 250 $cm^2$.

83. A method for wound size reduction in a subject having a diabetic foot infection, comprising administering to the subject a therapeutically effective amount of a composition comprising BisEDT, wherein the composition is applied to the infection and the wound is reduced in size from about a 1% reduction relative to the original wound size to total elimination of the wound within 12 weeks of the first administration of the composition.

84. The method of embodiment 83, wherein the wound is reduced by about 10%, 20%, 30%, 40%, 50%, 60%, 70%, 80%, or 90%.

85. The method of embodiment 84, wherein the wound is reduced by about 50%.

86. The method of any one of embodiments 83-85, wherein the composition is a suspension of microparticles comprising said BisEDT wherein at least 70% of the microparticles have a volumetric mean diameter (VMD) from about 0.4 μm to about 5 μm.

87. The method of any one of embodiments 83-86, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

88. The method of any one of embodiments 83-87, wherein the applied BT composition is present on the surface at a concentration from about 1 μg/$cm^2$ to about 1,000,000 μg/$cm^2$.

89. The method of any of embodiments 83-88, wherein the applied BT composition is present on the surface at a concentration from about 50 μg/$cm^2$ to about 100 μg/$cm^2$.

90. The method of any of embodiments 83-89, wherein the applied BT composition is present on the surface at a concentration greater than about 100 μg/$cm^2$ (e.g. as a dosage from about 250 μg/$cm^2$ to about 5,000 μg/$cm^2$).

91. The method of any one of embodiments 83-90, wherein the BT composition is administered three times per day, two times per day, once daily, every other day, once every three days, three times per week, once every week, once every other week, once every month, or once every other month.

92. The method of embodiment 91, wherein the BT composition is administered once daily or three times per week.

93. The method of any of embodiments 83-92, wherein the subject is administered multiple doses of the BT composition daily or weekly for a length of time ranging from about one week to about 12 weeks.

94. The method of embodiment 93, wherein the subject is administered multiple doses of the BT composition daily or weekly for a length of about 4 weeks.

95. The method of any of embodiments 83-94, wherein the wound area is from about 0.1 $cm^2$ to about 250 $cm^2$.

96. The method of any one of embodiments 83-95, wherein the wound surface area of said wound is reduced by 50% 12 weeks after the first administration of the BT composition, and the BT composition is BisEDT.

97. The method of embodiment 96, wherein the wound surface area of said wound is reduced by 50% 4 weeks after the first administration of the BisEDT composition.

98. The method of embodiments any one of embodiments 83-97, wherein the wound surface area is measured using digital photographs or hand measurement.

99. A method for preventing amputation and/or infection-related surgery in a subject having a diabetic foot infection, comprising administering to the subject a therapeutically effective amount of a BT composition.

100. The method of embodiment 99, wherein the BT composition is a suspension of microparticles comprising said BisEDT wherein at least 70% of the microparticles have a volumetric mean diameter (VMD) from about 0.4 μm to about 5 μm.

101. The method of any one of embodiments 99-100, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

102. The method of any one of embodiments 99-101, wherein the applied BT composition is present on the surface at a concentration from about 1 μg/$cm^2$ to about 1,000,000 μg/$cm^2$.

103. The method of any of embodiments 99-102, wherein the applied BT composition is present on the surface at a concentration from about 50 μg/$cm^2$ to about 100 μg/$cm^2$.

104. The method of any of embodiments 99-103, wherein the applied BT composition is present on the surface at a concentration greater than about 100 μg/$cm^2$ (e.g. as a dosage from about 250 μg/$cm^2$ to about 5,000 μg/$cm^2$).

105. A method of treating a wound in a subject, wherein the wound is 30 days old or greater, comprising administering to the subject a therapeutically effective amount of a BT composition.

106. The method of embodiment, 105, wherein the subject has a diabetic foot infection.

107. The method of embodiment 105 or 106, wherein the BT composition is a suspension of microparticles comprising BisEDT wherein at least 70% of the microparticles have a volumetric mean diameter (VMD) from about 0.4 μm to about 5 μm.

108. The method of any one of embodiments 105-107, wherein the BT composition further comprises about 0.05% to about 1.0% Tween 80®, about 0.05 to 40 mM sodium chloride, optionally about 1% to about 10% of methylcellulose, and optionally about 2 to 20 mM sodium phosphate at about pH. 7.4.

109. The method of any one of embodiments 105-108, wherein the applied BT composition is present on the surface at a concentration from about 1 μg/$cm^2$ to about 1,000,000 μg/$cm^2$.

110. The method of any of embodiments 105-109, wherein the applied BT composition is present on the surface at a concentration from about 50 μg/$cm^2$ to about 100 μg/$cm^2$.

111. The method of any of embodiments 105-110, wherein the applied BT composition is present on the surface at a concentration greater than about 100 μg/$cm^2$ (e.g. as a dosage from about 250 μg/$cm^2$ to about 5,000 μg/$cm^2$).

112. The method of any of embodiments 105-111, wherein the wound is greater than 2 months old, greater than 3 months old, greater than 4 months old, greater than 5 months old, greater than 6 months old, greater than 7 months old, greater than 8 months old, greater than 9 months old, greater than 10 months old, greater than 11 months old, or greater than 1 year old.

113. The method of embodiment 112, wherein the wound is greater than 2 months old.

114. The method of embodiment 112, wherein the wound is greater than 3 months old.

115. The method of any one of embodiments 1-114, wherein the BT composition comprises BisEDT and wherein the composition is a suspension of microparticles comprising said BisEDT compounds having a volumetric mean diameter (VMD) from about 0.4 μm to about 5 μm.

116. The method of embodiment 115, wherein at least 70% of the microparticles have a VMD from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

117. The method of embodiment 116, wherein the VMD is from about 0.4 μm to about 3 μm.

118. The method of embodiment 116, wherein the VMD is from about 1.0 μm to about 2.0 μm.

119. The method of any one of embodiments 116-118, wherein at least 70%, 75%, 80%, 90%, or 95% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

120. The method of embodiment 119, wherein at least 80% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

121. The method of embodiment 119, wherein at least 90% of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

122. The method of embodiment 119, wherein substantially all of the microparticles have a VMD of from about 0.4 μm to about 3 μm, or from about 0.5 μm to about 2 μm, or from about 0.7 μm to about 2 μm, or from about 0.8 μm to about 1.8 μm, or from about 0.8 μm to about 1.6 μm, or from about 0.9 μm to about 1.4 μm, or from about 1.0 μm to about 2.0 μm, or from about 1.0 μm to about 1.8 μm.

123. The method of any embodiment of 119-122, wherein the VMD is from about 0.4 μm to about 3 μm.

124. The method of any embodiment of 119-122, wherein the VMD is from about 1.0 μm to about 2.0 μm.

125. The method of any of the preceding embodiments, wherein 90% of the particles are smaller than about 10 μm.

126. The method of embodiment 125, wherein 90% of the particles are smaller than about than about 10 μm, about 9 μm, about 8 μm, about 7 μm, about 6 μm, about 5 μm, about 4 μm, about 3 μm, about 2 μm, or about 1 μm.

127. The method of any of the preceding embodiments, wherein the bacterial species is *Acinetobacter baumannii, Acinetobacfer junii, Anaerococcus lactolyticus, Anaerococcus vaginalis, Anaerococcus murdoch, Anaerococcus tetradius, Anaerococcus hydrogenalis, Actinobaculum massiliense, Actinobaculum schaalii, Actinomyces europaeus, Actinomyces hominis, Actinomyces neuii, Actinomyces radingae, Alcaligenes faecalis, Abiotrophia paraadiacens, Bacteroides fragilis, Bulleidia extructa, Bilophila wadsworthia, Campylobacter ureolyticus, Citrobacter murliniae, Clostridium saccharogumia, Clostridium novyi, Corynebacterium accolens, Corynebacterium amycolatum, Corynebacterium aurimucosum, Corynebacterium freiburgense, Corynebacterium hansenii, Corynebacterium jeikeium, Corynebacterium mycetoide, Corynebacterium simulans, Corynebacterium Tuberculostearicum, Corynebacterium xerosis, Corynebacterium striatum, Dermabacter hominis, Dialister invisus, Dialister propionicifaciens, Dialister micraerophilus, Dialister pneumosintes, Delftia acidovorans, Enterobacter aerogenes, Enterobacter cloacae, Enterobacter hormaechei, Enterococcus faecalis, Enterococcus canintestini, Escherichia coli, Escherichia fergusonii, Escherichia vulneris, Enterococcus avium, Enterococcus gallinarum, Enterococcus casseliflavus, Eggerthella lenta, Finegoldia magna, Fusobacterium canifelinum, Fusobacterium nucleatum, Fusobacterium periodontium, Granulicatella adiacens, Gemella morbillorum, Globicatella sanguinis, Haemophilus parainfluenzae, Haemophilus segnis, Helcococcus kunzii, Helcococcus kunzii, Klebsiella oxytoca, Kocuria atrinae, Leclercia adecarboxylata, Mobiluncus curtisii, Moryella indoligenes, Morganella morganii, Negativicoccus succinicivorans, Peptoniphilus harei, Peptoniphilus gorbachii, Peptoniphilus ivorii, Peptoniphilus lacrimalis, Peptoniphilus olsenii, Peptoniphilus asacchrolyticus, Parvimonas micra, Peptococcus niger, Peptostreptococcus anaerobius, Peptostreptococcus stomatis, Porphyromonas asaccharolytica, Porphyromonas bennonis, Porphyromonas somerae, Porphyromonas uenonis, Porphyromonas levii, Prevotella timonensis, Prevotella bergensis, Prevotella buccalis, Prevotella corporis, Prevotella disiens, Prevotella intermedia, Prevotella nanceiensis, Pseudomonas indica, Pseudomonas otitidis, Psychrobacter lutiphocae, Proteus myxofaciens, Proteus hauseri, Providencia rettgeri, Providencia stuartii, Staphylococcus aureus, Staphylococcus epidermidis, Staphylococcus carnosus, Staphylococcus chromogenes, Staphylococcus devriesei, Staphylococcus hominis, Staphylococcus lugdunensis, Serratia nematodiphila, Stenotrophomonas maltophilia, Staphylococcus pettenkoferi, Staphylococcus capitis, Staphylococcus saprophyticus, Streptococcus agalactiae, Streptococcus anginosus, Streptococcus canis, Streptococcus dysgalactiae, Streptococcus infantarius, Streptococcus oralis, Serratia grimesii, Stenotrophomonas pavanii, Salmonella enterica, Trueperella bernardiae, Varibaculum cambriense, Veillonella atypica, Veillonella parvula, Veillonella dispar, Veillonella rogosae, Acinetobacter calcoaceticus, Acinetobacter Iwoffii, Anaerococcus prevotii, Bacteroides caccae, Bacteroides distasonis, Bacteroides ovatus, Bacteroides stercoris, Bacteroides thetaiotaomicron, Bacteroides uniformis, Bacteroides vulgatus, Corynebacterium striatum, Clostridium innocuum, Clostridium perfringens, Clostridium ramosum, Pluralibacter gergoviae, Fusobacterium mortiferum, Klebsiella oxytoca, Klebsiella pneumoniae, Pseudomonas aeruginosa, Peptococcus magnus, Prevotella bivia, Prevotella melaninogenica, Porphyromonas asaccharolytica, Peptostreptococcus asaccharolyticus, Peptostreptococcus micros, Proteus mirabilis, Staphylococcus haemolyticus, Staphylococcus simulans, Staphylococcus saprophyticus, Streptococcus pneumoniae, Streptococcus agalactiae, Streptococcus mitis, Streptococcus milleri, Streptococcus dysgalactiae, Streptococcus canis, Serratia marcescens, Serratia liquefaciens, Stenotrophomonas maltophila,* or *Epidermolysis bullosa* and/or the fungal species is *Candida* spp., *Cladosporium* spp., *Aspergillus* spp., *Penicillium* spp., *Alternaria* spp., *Pleospora* spp., *Fusarium* spp, *Candida lusitanicte, Candida parapsilisis,* or *Candida albicans.*

EXAMPLES

The following examples are provided to illustrate the present disclosure, and should not be construed as limiting thereof. Additional experimental procedures and details can be found in International Patent Application Nos. PCT/US2010/023108, PCT/US2011/023549, and PCT/US2011/047490, which are hereby incorporated by reference in their entireties for all purposes.

Example 1. General Synthesis

The starting materials and reagents used in preparing these compounds are either available from commercial suppliers such as Aldrich Chemical Co., Bachem, etc., or can be made by methods well known in the art. The starting materials and the intermediates and the final products of the reaction can be isolated and purified if desired using conventional techniques, including but not limited to filtration, distillation, crystallization, chromatography, and the like and can be characterized using conventional means, including physical constants and spectral data. Unless specified otherwise, the reactions described herein take place at atmospheric pressure over a temperature range from about −78° C. to about 150° C.

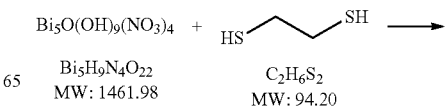

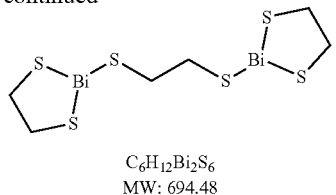

C₆H₁₂Bi₂S₆
MW: 694.48

Microparticulate bismuth-1,2-ethanedithiol (Bis-EDT, soluble bismuth preparation) was prepared as follows: To an excess (11.4 L) of 5% aqueous HNO$_3$ at room temperature in a 15 L polypropylene carboy was slowly added by dropwise addition 0.331 L (~0.575 moles) of an aqueous Bi(NO$_3$)$_3$ solution (43% Bi(NO$_3$)$_3$ (w/w), 5% nitric acid (w/w), 52% water (w/w), Shepherd Chemical Co., Cincinnati, Ohio, product no. 2362; δ~1.6 g/mL) with stirring, followed by slow addition of absolute ethanol (4 L). Some white precipitate formed but was dissolved by continued stirring. An ethanolic solution (~1.56 L, ~0.55 M) of 1,2-ethanedithiol (CAS 540-63-6) was separately prepared by adding, to 1.5 L of absolute ethanol, 72.19 mL (0.863 moles) of 1,2-ethanedithiol using a 60 mL syringe, and then stirring for five minutes. The 1,2-ethanedithiol/EtOH reagent was then slowly added by dropwise addition over the course of five hours to the aqueous Bi(NO$_3$)$_3$/HNO$_3$ solution, with continued stirring overnight. The formed product was allowed to settle as a precipitate for approximately 15 minutes, after which the filtrate was removed at 300 mL/min using a peristaltic pump. The product was then collected by filtration on fine filter paper in a 15-cm diameter Buchner funnel, and washed sequentially with three, 500-mL volumes each of ethanol, USP water, and acetone to obtain BisEDT (694.51 gm/mole) as a yellow amorphous powdered solid. The product was placed in a 500 mL amber glass bottle and dried over CaCl$_2$) under high vacuum for 48 hours. Recovered material (yield~200 g) gave off a thiol-characteristic odor. The crude product was redissolved in 750 mL of absolute ethanol, stirred for 30 min, then filtered and washed sequentially with 3×50 mL ethanol, 2×50 mL acetone, and washed again with 500 mL of acetone. The rewashed powder was triturated in 1M NaOH (500 mL), filtered and washed with 3×220 mL water, 2×50 mL ethanol, and 1×400 mL acetone to afford 156.74 gm of purified BisEDT. Subsequent batches prepared in essentially the same manner resulted in yields of about 78-91%.

The product was characterized as having the structure shown above by analysis of data from $^1$H and $^{13}$C nuclear magnetic resonance (NMR), infrared spectroscopy (IR), ultraviolet spectroscopy (UV), mass spectrometry (MS) and elemental analysis. An HPLC method was developed to determine the chemical purity of BisEDT whereby the sample was prepared in DMSO (0.5 mg/mL). The λ$_{max}$ was determined by scanning a solution of BisEDT in DMSO between 190 and 600 nm. Isocratic HPLC elution at 1 mL/min was performed at ambient temperature in a mobile phase of 0.1% formic acid in acetonitrile:water (9:1) on a Waters (Millipore Corp., Milford, Mass.) model 2695 chromatograph with UV detector monitoring at 265 nm (λ$_{max}$), 2 μL injection volume, equipped with a YMC Pack PVC Sil NP, 5 μm, 250×4.6 mm inner diameter analytical column (Waters) and a single peak was detected, reflecting chemical purity of 100±0.1%. Elemental analysis was consistent with the structure of BisEDT as shown above.

The dried particulate matter was characterized to assess the particle size properties. Briefly, microparticles were resuspended in 2% Pluronic® F-68 (BASF, Mt. Olive, N.J.) and the suspension was sonicated for 10 minutes in a water bath sonicator at standard setting prior to analysis using a Nanosizer/Zetasizer Nano-S particle analyzer (model ZEN1600 (without zeta-potential measuring capacity), Malvern Instruments, Worcestershire, UK) according to the manufacturer's recommendations. From compiled data of two measurements, microparticles exhibited a unimodal distribution with all detectable events between about 0.6 microns and 4 microns in volumetric mean diameter (VMD) and having a peak VMD at about 1.3 microns.

Example 2. The Synthesis of Microparticulate Bismuth-1,2-Ethanedithiol (Bis-EDT)

Water (25.5 L) and 70% nitric acid (1800 mL) were mixed together in a Nalgene reactor. Then, water (2300 mL) was added to an Erlenmeyer flask, followed by bismuth subnitrate (532 g), and the mixture was stirred. To the mixture was added 70% nitric acid (750 mL) to obtain a clear solution. This solution was transferred into the Nalgene reactor and the resulting mixture was stirred for 20 min. Then, 9.5 L of 95% EtOH was added to the reactor in three portions.

Separately, 1,2-ethanedithiol, 98%, (229 mL) was added to a bottle followed by two 250 mL EtOH portions with stirring. A further 5 L EtOH was added to the bottle with stirring. The 1,2-ethanedithiol solution was then added to the reactor over about 4 hours while stirring. After stirring for 18 hours, the solids were allowed to settle for 2 hours. EtOH (20 L) was added and the mixture stirred for 24 hours. The solids were allowed to settle for 1.5 hours, then separated by filtration of the mixture, followed by rinsing with EtOH.

To the empty reactor was added 9 L EtOH and the filtered solids, which was stirred for 18 hours. The solids were allowed to settle for 1 hour, then separated by filtration of the mixture, followed by rinsing with EtOH. Next, the empty reactor was charged with 9 L acetone, 99.5%, and the filtered solids, which was stirred for 15 hours. The solids were allowed to settle for 1.5 hours, then separated by filtration of the mixture, followed by rinsing with acetone. Again, the empty reactor was charged with 9 L acetone, 99.5%, and the filtered solids, which was stirred for 1.4 hours. The solids were filtered and air-dried for 69 hours, then vacuum-dried for 4 hours. After mixing the solid, it was sieved through a 10 mesh (2 mm) and then 18 mesh (1 mm) sieve to give BisEDT.

Example 3. The Synthesis of Additional BT Compounds

The following bismuth thiol compounds can also be prepared according to the methods of Examples 1 and 2:

bismuth-2,3-dimercaptopropanol (2:3 molar ratio, BisBAL)
bismuth-4-methyl-1,2-benzenedithiol (2:3 molar ratio, BisTOL)
bismuth-2,3-butanedithiol (BisBDT)

Example 4. Establishment of *Staphylococcus aureus* (*S. aureus*) Mouse Model to Evaluate the Efficacy of BisEDT on Spleen and Wound Titer Establishment of Mouse Model: A luminescent strain of *Staphylococcus aureus* (*S. aureus*) was administered intravenously to adult, female, Swiss Webster mice and 48 hours was allowed for a biofilm to form. Mice were treated daily intravenously with 100 μL of serial dilutions of BisEDT. In this example, BisEDT was used as a suspension (w:v) (e.g. 150, 375, or 750 μg/mL) of drug particles in diluent, which is composed of 3% methylcellulose/0.5% polysorbate 80/10 mM sodium chloride/10 mM sodium phosphate, pH 7.4.

Imaging Studies: Mice were imaged using Silhouette to determine wound size and volume, and In Vivo Imaging Systems (IVIS) Lumina X5 to quantitate bioluminescence.

Terminal colony forming units (CFU) were determined by plating homogenized tissue from the wound bed and in the spleen. Mice were euthanized and wound tissue and spleens were harvested. Tissue samples were weighed and placed into microtubes containing sterile phosphate buffer and homogenized. The homogenate was then serially diluted and plated to determine CFU/g tissue.

An initial study evaluated the effect of BisEDT suspension on CFUs in the spleen and wound bed. The study occurred over 11 days with 9 days of treatment. The BisEDT suspension was administered to 30 (n=5 mice/group) mice at concentrations of 2500, 250, 25, 2.5, 0.25, 0.25, 0.025 μg/mL. A comparator control was vehicle, or diluent, and 50% DMSO in PBS.

Figure 2:
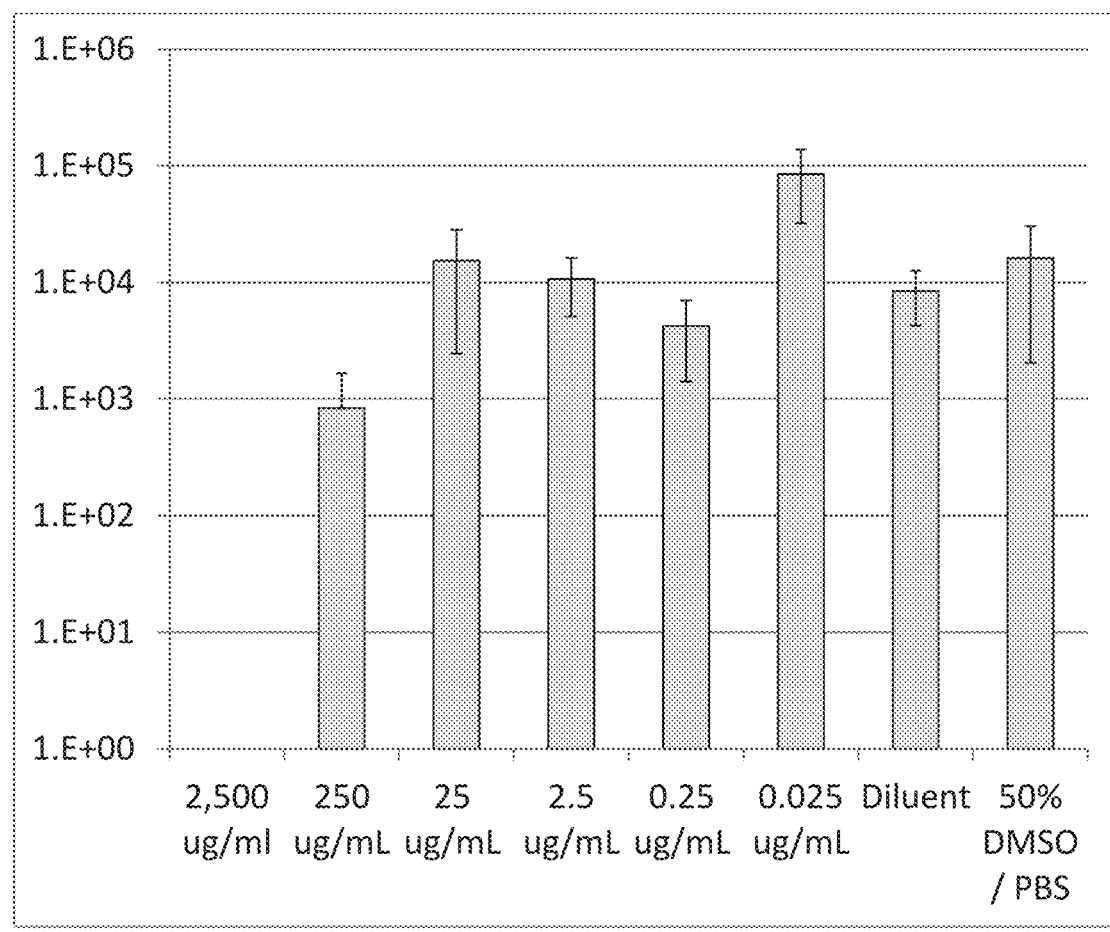

The results showed that 2500 μg/mL BisEDT reduces wound titer by approximately five logs compared to diluent (FIG. 1) and completely inhibits spleen infection (≥4 fold log reduction) compared to diluent (FIG. 2).

Figure 3:
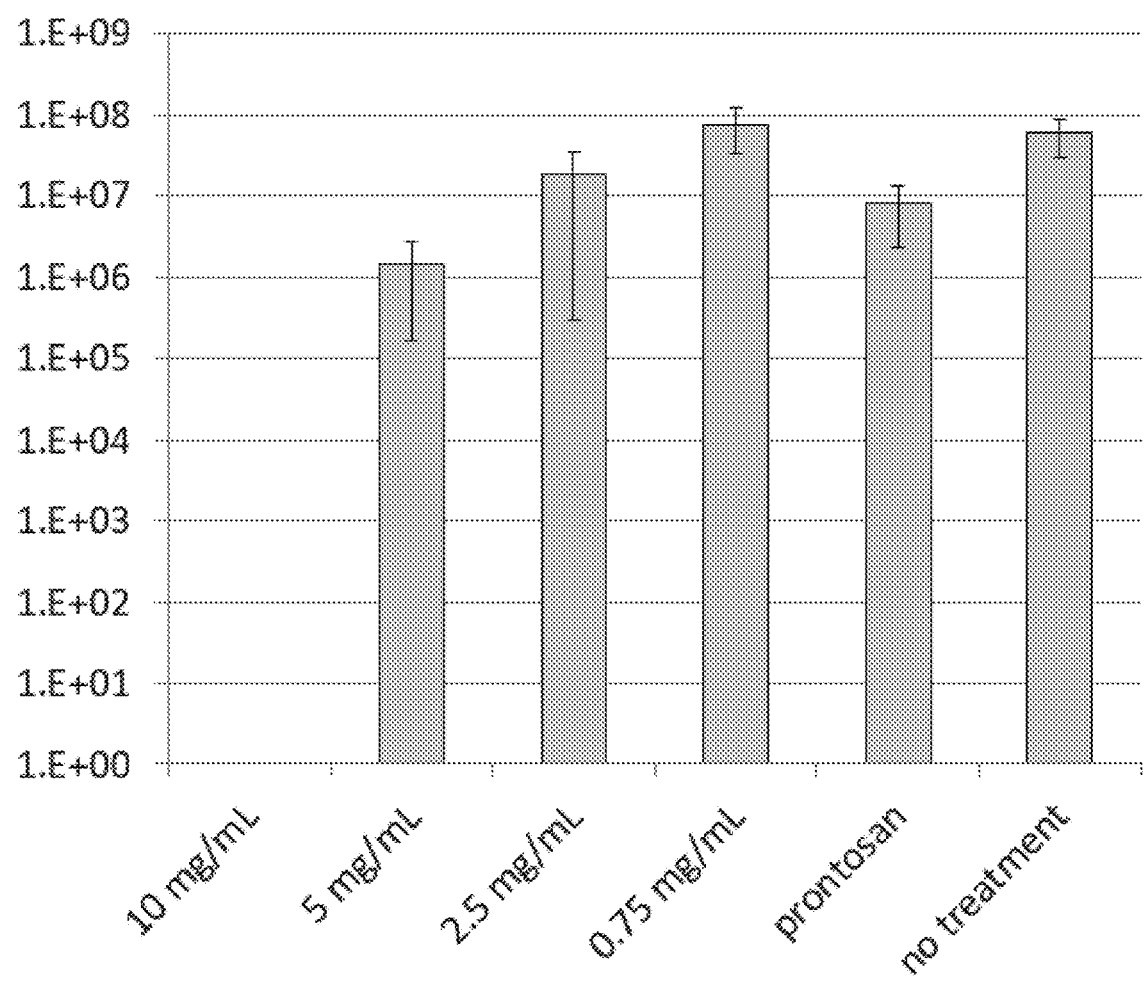
Figure 4:
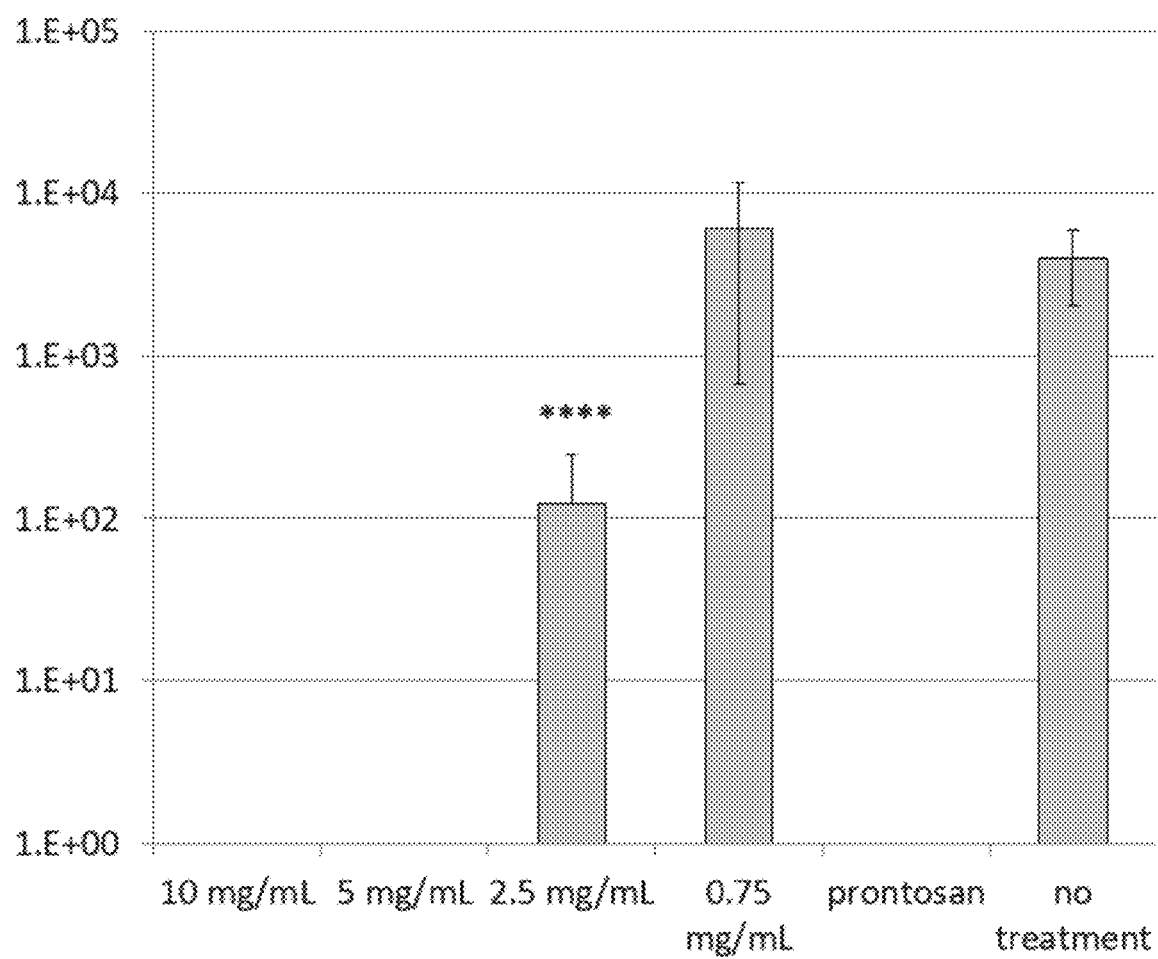

A subsequent study evaluated the effect of higher concentrations of BisEDT suspension on CFUs in the spleen and wound bed. The study occurred over 12 days with 10 days of treatment. BisEDT suspension was administered to 20 (n=5 mice/group) at concentrations of 10, 5, 2.5, and 0.75 mg/mL. A negative control was mice that were untreated, and a positive control was mice that were treated with Prontosan. The results show that treatment with 10 mg/mL BisEDT reduced CFUs by more than eight logs. Complete inhibition was observed compared to the untreated control (FIG. 3). Further, treatment with 5 mg/mL BisEDT reduced CFUs by 1.5-2 logs, greater than the positive prontosan control. There was no significant inhibition at concentrations of 2.5 mg/mL BisEDT or less (FIG. 3). Treatment of 5 or 10 mg/mL BisEDT and Prontosan completely inhibited spleen CFU (≥3.5 log reduction) compared to untreated control (FIG. 4). At a dose of 2.5 mg/mL BisEDT, three mice exhibited no infection, and one had a CFU reduction of about 1.5 log (FIG. 4).

Example 5. Mouse Model to Evaluate the Efficacy of BisEDT on Bioluminescence

This study evaluated the effect of BisEDT suspension on CFUs by bioluminescence imaging over time 1, 3, 5, 7, and 9 days after treatment with BisEDT suspension. Mice were sacrificed at day 11, and the number of CFU/gram were quantitated for the wound bed and spleen. Six groups of five mice were included in the study. Mice were treated with BisEDT at doses of 10 mg/mL, 5 mg/mL, 2.5 mg/mL, or 0.75 mg/mL. As a positive control, mice were dosed with prontosan. As a negative control, mice were untreated.

Figure 5A:
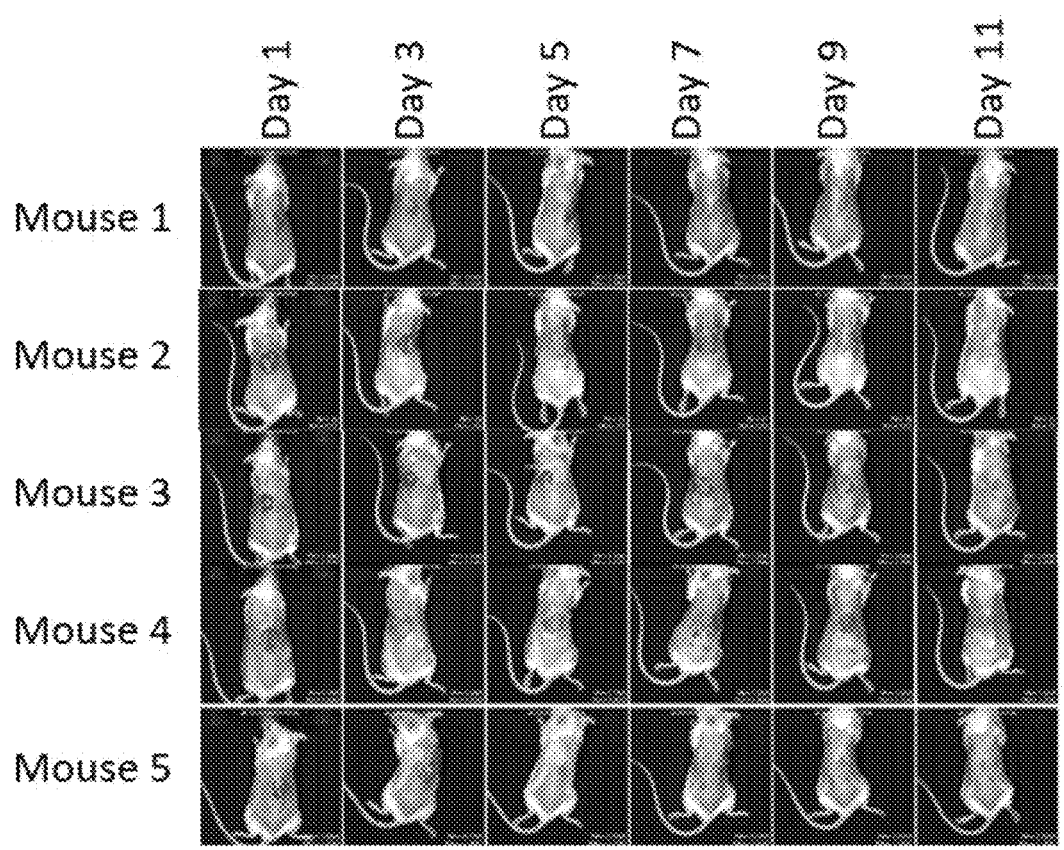
Figure 5B:
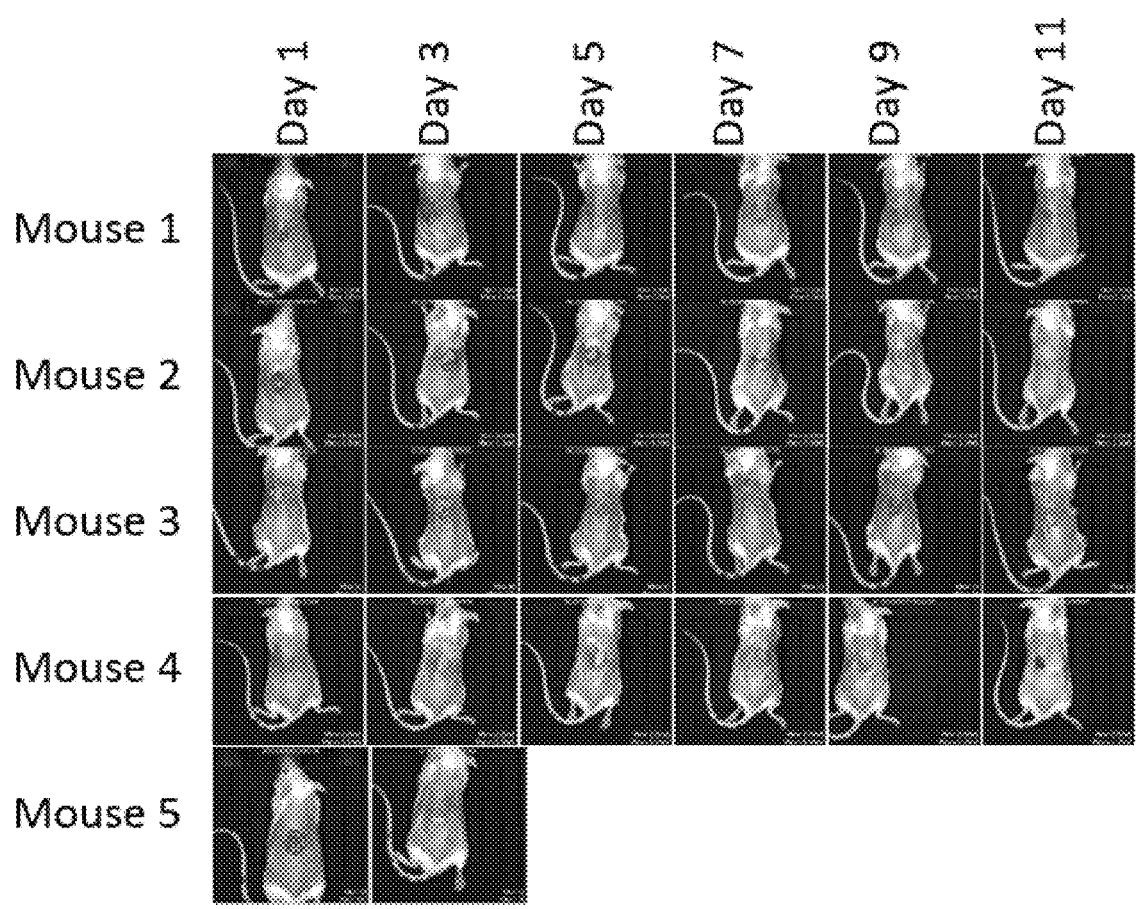
Figure 5C:
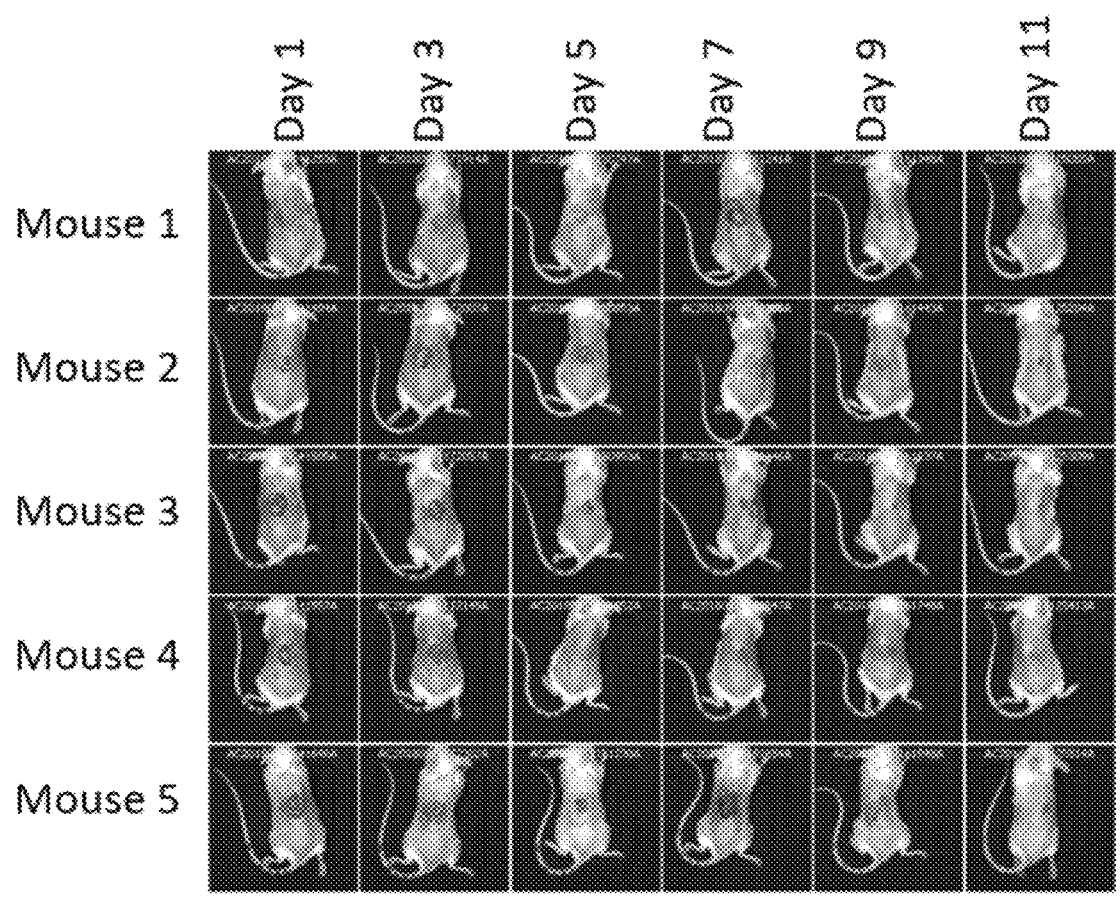
Figure 5D:
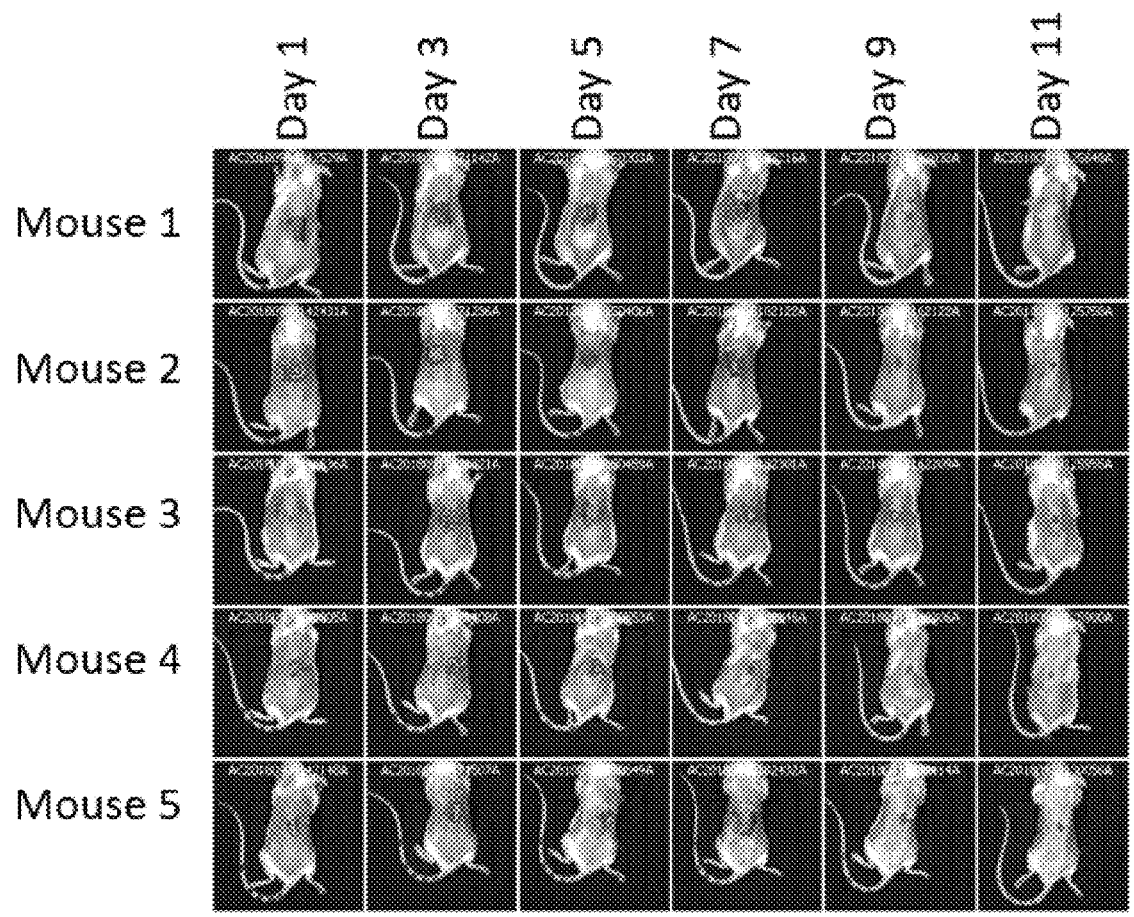
Figure 5E:
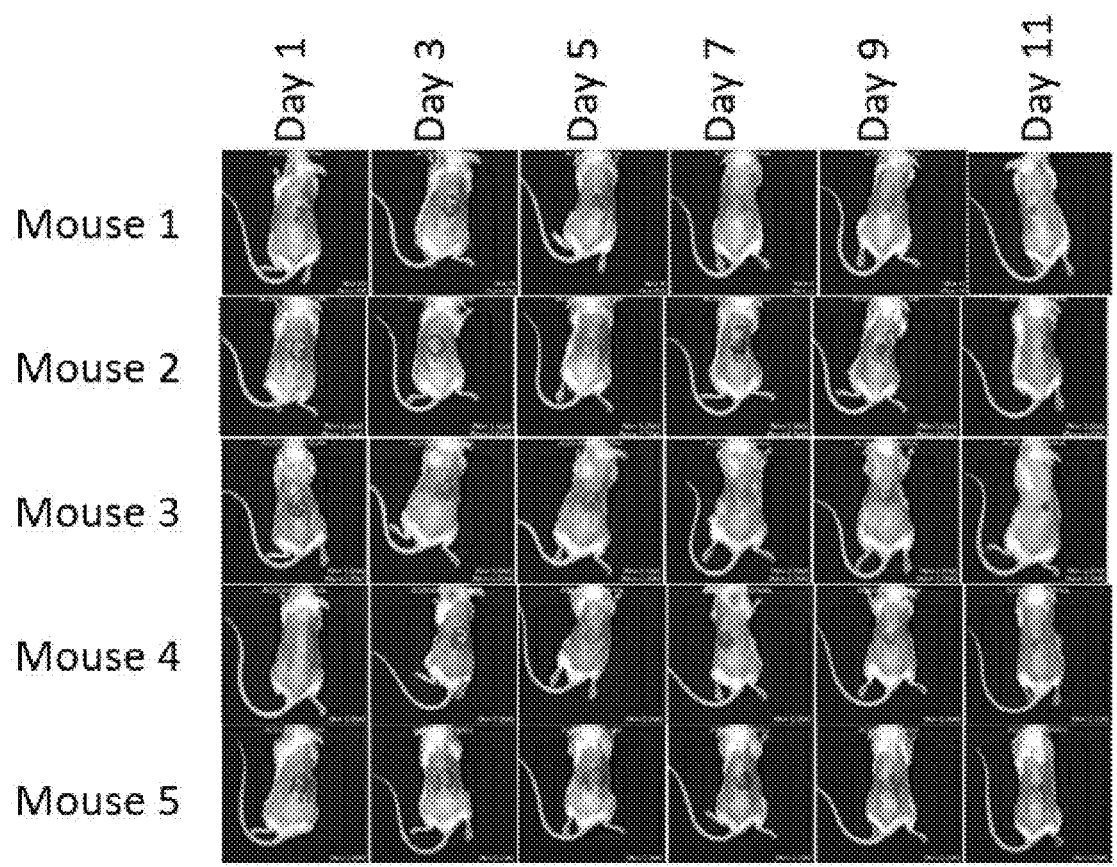
Figure 5F:
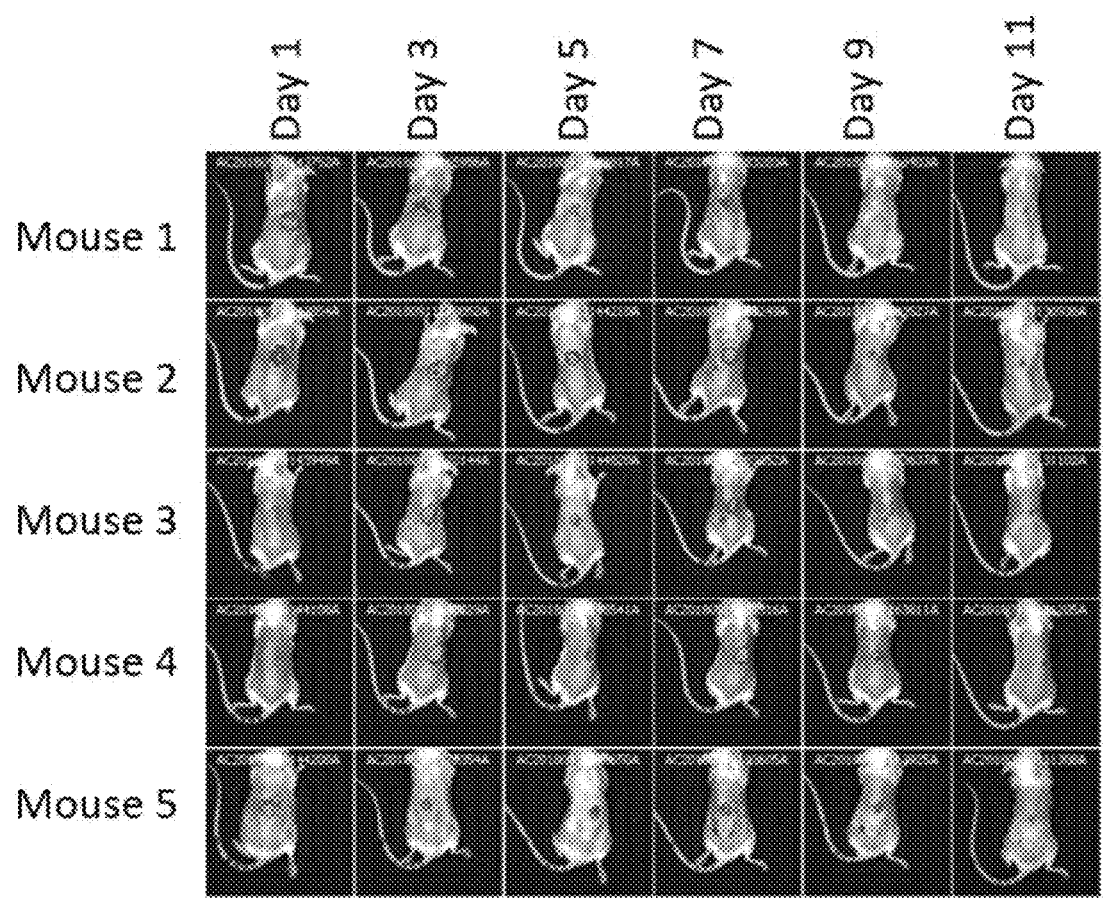

Bioluminescent images of mice treated with BisEDT at 10 mg/mL, 5 mg/mL, 2.5 mg/mL, or 0.75 mg/mL are contained in FIG. 5A, FIG. 5B, FIG. 5C, and FIG. 5D, respectively. Bioluminescent images of mice treated with prontosan are contained in FIG. 5E, and bioluminescence images of untreated mice are contained in FIG. 5F. Mice that are not shown did not wake up after isoflurane treatment. Mouse 1 of the 10 mg/mL BisEDT treatment group did not establish an infection with *S. aureus*. Mouse 4 of the 5 mg/mL BisEDT treatment group did not establish an infection with *S. aureus*.

Table 1A-C shows the CFU/g in the wound bed and spleen in each mouse after sacrifice.

TABLE 1A

CFU/g measurements of wound beds and spleens of mice treated with 10 mg/mL BisEDT and 5 mg/mL BisEDT

| 10 mg/mL BisEDT | | | 5 mg/mL BisEDT | | |
|---|---|---|---|---|---|
| Mouse | Wound bed | Spleen | Mouse | Wound bed | Spleen |
| 1 | 0 | 0 | 1 | 1.59E+03 | 0 |
| 2 | 0 | 0 | 2 | 5.00E+05 | 0 |
| 3 | 0 | 0 | 3 | 5.41E+06 | 0 |
| 4 | 0 | 0 | 4 | 0 | 0 |
| 5 | 0 | 0 | 5 | N/A | N/A |

TABLE 1B

CFU/g measurements of wound beds and spleens of mice treated with 2.5 mg/mL BisEDT and 0.75 mg/mL BisEDT

| 2.5 mg/mL BisEDT | | | 0.75 mg/mL BisEDT | | |
|---|---|---|---|---|---|
| Mouse | Wound bed | Spleen | Mouse | Wound bed | Spleen |
| 1 | 0 | 0 | 1 | 2.00E+08 | 0 |
| 2 | 8.11E+05 | 6.21E02 | 2 | 2.62E+07 | 7.25E+02 |
| 3 | 3.92E+05 | 0 | 3 | 2.56E+06 | 6.37E+02 |
| 4 | 3.13E+03 | 0 | 4 | 8.00E+07 | 2.82E+04 |
| 5 | 8.96E+07 | 0 | 5 | x | 1.34E+03 |

TABLE 1C

CFU/g measurements of wound beds and spleens of untreated mice and mice treated with prontosan

| Prontosan | | | No Treatment | | |
|---|---|---|---|---|---|
| Mouse | Wound bed | Spleen | Mouse | Wound bed | Spleen |
| 1 | 0 | 0 | 1 | 1.20+08 | 1.08+03 |
| 2 | 2.86E+07 | 0 | 2 | 1.75+E07 | 9.71E+03 |
| 3 | 0 | 0 | 3 | 1.64E+06 | 7.58E+03 |
| 4 | 0 | 0 | 4 | 2.00E+07 | 6.37E+02 |
| 5 | 1.14E+07 | 0 | 5 | 1.38+08 | 8.62E+02 |

Example 6. A Phase 1b/2a Randomized, Double-Blind, Placebo-Controlled, Multi-Center Study to Assess the Efficacy of Topical BisEDT in Patients with Moderate to Severe Diabetic Foot Infection Adjunctive local administration of BisEDT was tested for its efficacy in resolving both infection and critical colonization, thereby removing these barriers to wound repair and closure. This represents a fundamental, clinically meaningful benefit.

Topical BisEDT suspension and placebo were used in combination with SOC systemic antibiotics (such as levofloxacin) for a duration of 2-3 weeks. This resulted in a similar proportion of patients in the BisEDT treated groups as compared to placebo who were clinically cured at the test of cure visit, which occurred two weeks following the end of treatment. The 3-D photographic data of wound size suggested that BisEDT may be beneficial in facilitating wound repair and closure, as compared to placebo. A larger proportion of BisEDT treated subjects had a >50% reduction in wound surface area from baseline at the end of treatment (Week 2-3), test of cure (Week 4-5), and at the end of study (Week 8-9) (Table 2). BisEDT, when used in conjunction with systemic antibiotics, for a duration of four weeks (3× per week) may be beneficial in resolving both infection and critical colonization, therefore enabling wound repair and closure, a fundamental, clinically meaningful benefit.

TABLE 2

Proportion of patients with a >50% reduction in wound surface area in Study topical BisEDT suspension, using 3D Digital Photographs

| | Treatment Group | | | | |
|---|---|---|---|---|---|
| Time Point | BisEDT 3 µg/ cm$^2$ (N = 12) | BisEDT 7.5 µg/ cm$^2$ (N = 12) | BisEDT 15 µg/ cm$^2$ (N = 15) | BisEDT Pooled (N = 39) | Placebo (N = 13) |
| End of Treatment (Week 2-3) | 42% | 55% | 33% | 42% | 23% |
| Test of Cure (Week 4-5) | 55% | 67% | 57% | 59% | 39% |
| End of Study (Week 8-9) | 55% | 63% | 64% | 61% | 42% |

Example 7: A Phase 1b/2a Randomized, Double-Blind, Placebo-Controlled Study to Assess the Safety, Tolerability and Efficacy of Adjunctive Treatment with Topically Applied BISEDT in Subjects with Moderate to Severe Diabetic Foot Infection (DFI)

The primary objective of Part 1 of this study and the planned primary objective of Part 2 of this study was to evaluate the safety and tolerability of topically administered BisEDT composition as adjunct to standard of care (including systemic antibiotic therapy) in subjects with a moderate to severe DFI. The secondary objectives of Part 1 of this study and the planned secondary objectives of Part 2 of this study were: To evaluate the effect of adjunctive BisEDT composition on resolution of infection; To evaluate the effect of adjunctive BisEDT composition on eradication of pathogens; To evaluate the effect of BisEDT composition on eradication of biofilms; To evaluate the effect of BisEDT composition on wound healing; To evaluate the effect of BisEDT composition for the prevention of lower extremity amputations; To evaluate the effect of BisEDT composition for the prevention of infection related surgery; To evaluate the effect of BisEDT composition on duration of systemic antibiotic use; To evaluate the effect of BisEDT composition on length of hospital stay; To evaluate the systemic absorption and pharmacokinetics of topically administered BisEDT composition.

Methodology: This was a randomized, double-blind, placebo-controlled, multicenter study that was planned to be conducted in 2 parts. In Part 1, subjects were enrolled into escalating dose cohorts (BisEDT at concentrations of 150, 375, and 750 µg/mL resulting in doses of 3, 7.5, and 15 µg/cm$^2$) (N=16 per cohort) at a ratio of 3:1 (BisEDT to placebo). In Part 2, it was planned that subjects would be randomized in a 1:1 ratio (BisEDT to placebo) based on the optimal dose demonstrated in Part 1 of the study.

Subjects with diabetes mellitus and a foot infection with an Infectious Disease Society of America (IDSA) infection severity rating of moderate or severe and a diabetic foot ulcer (DFU), which had been present for greater than 4 weeks (ensuring the subjects were suffering from chronic, persistent wounds), were eligible for the study. Subjects may have been enrolled if they received no more than 36 hours of antibiotic therapy prior to enrollment unless there was clinical and/or microbiological evidence of failure. Subjects with a need for surgical therapy beyond standard bedside wound debridement, or incision and drainage, to treat the DFI after enrollment, should not have been enrolled. Both inpatients and outpatients were eligible if they met all of the inclusion criteria and none of the exclusion criteria. Subjects may have been screened and enrolled over 2 consecutive days.

In Part 1, subjects received either topical application of BisEDT or topical application of placebo, applied directly to the infected ulcer, 3 times per week, for a minimum of 2 weeks (ie, 6 doses) and up to a maximum of 3 weeks (ie, 9 doses). The duration between doses was greater than 24 hours and did not exceed 72 hours. The determination to stop topical BisEDT therapy after a minimum of 2 weeks (ie, 6 doses) was at the discretion of the Principal Investigator and based on the resolution of clinical findings of infection.

All subjects also received systemic antibiotic treatment based on the protocol defined algorithm. Systemic antibiotic therapy continued until, but not beyond, the resolution of findings of infection, as outlined in the 2012 IDSA clinical practice guideline for the diagnosis and treatment of diabetic foot infections.

All subjects required to adhere to proper pressure offloading of the foot wound (when needed) with a removable cast walker from enrollment through End of Study (EOS), as directed by the treating physician.

All subjects underwent appropriate sharp debridement at baseline prior to first application of BisEDT or placebo. Subjects returned for dressing changes and re-application of BisEDT or matching placebo 3 times per week until cessation of treatment. The duration between doses was greater than 24 hours and did not exceed 72 hours. Subjects returned to the clinic for a Test of Cure (TOC) visit 2 weeks after completion of treatment. An EOS visit took place 4 weeks after completion of treatment.

During the study, subjects underwent sharp debridement once per week. More frequent sharp debridement occurred if medically indicated, based on the clinical judgment of the Principal Investigator.

A designated unblinded study nurse at each site diluted BisEDT to the specified clinical concentrations and applied BisEDT or placebo to the wound and covered the wound with one of the appropriate dressings supplied. In addition, prior to the Investigator assessing the clinical signs and symptoms of the wound at each follow-up visit, the unblinded study nurse removed the previous dressing, assessed the wound for purulent drainage, and cleared away any residual BisEDT or placebo through irrigation of the wound with saline for 15 seconds, then disposed (and removed from any potential view of the blinded Investigator) all old dressings and equipment prior to the blinded Investigator assessing the clinical signs and symptoms of the wound; such disposal included removal of the disposal bag into which the old dressings etc., were placed. At each visit during which application of BisEDT or placebo took place, subject blinding was maintained through the use of a visual barrier or subject blindfold and careful restriction of discussion between the study staff and subject.

Duration of Treatment: 14-21 days; Number of subjects: Planned: 48 subjects; Screened: 61 subjects; Randomized: 53 subjects; Completed: 46 subjects; Discontinued: 7 subjects.

Diagnosis and Main Criteria for Inclusion: The population for this study was male and female subjects ≥18 and 75 years of age that had been diagnosed with diabetes mellitus; had a skin ulcer located on or distal to the malleolus that was >4 weeks old and presented with clinical manifestations of a moderate or severe infection based on IDSA guidelines; and had received appropriate surgical debridement. Subjects must have received no more than 36 hours of antibiotic therapy prior to enrollment unless there was clinical and/or microbiological evidence of failure, and had documented adequate arterial perfusion in the affected limb.

Subjects were excluded from the study if they had proven, or highly suspected, involvement of bone (ie, osteomyelitis), more than 1 concurrent infected DFU, or a DFU that measured >200 cm$^2$.

Investigational Product and Comparator Information: BisEDT or placebo was topically applied to the wound. The overall BisEDT dose levels were 3, 7.5, and 15 μg/cm$^2$.

BisEDT was provided to the clinic as a 2.5 mg/mL suspension that was diluted by the designated unblinded study nurse or coordinator to the specific concentration for each cohort (150, 375, or 750 μg/mL), according to the Instructions for Use. The suspension of 150, 375, or 750 μg/mL (w:v) BisEDT drug particles was prepared in diluent, composed of 3% methylcellulose/0.5% polysorbate 80/10 mM sodium chloride/10 mM sodium phosphate, pH 7.4.

Placebo (diluent) was composed of 3% methylcellulose/ 0.5% polysorbate 80/10 mM sodium chloride/10 mM sodium phosphate, pH 7.4 (up to 4 mL dose volume).

The administered doses were as follows: Cohort 1: 150 μg/mL BisEDT=3 μg/cm$^2$; Cohort 2: 375 μg/mL BisEDT=7.5 μg/cm$^2$; Cohort 3: 750 μg/mL BisEDT=15 μg/cm$^2$.

Selection and Timing of Dose for Each Subject: Eligible subjects were dosed according to the cohort they were enrolled in. Subjects were dosed 3 times per week (eg, Monday, Wednesday, and Friday) for a minimum of 2 weeks and up to a maximum of 3 weeks. The duration between doses was greater than 24 hours and did not exceed 72 hours.

Criteria for Evaluation:

Efficacy: The following clinical and microbiological efficacy outcomes were assessed:

Proportion of subjects with a clinical cure of infection 2 weeks following the end of dosing, TOC with BisEDT or placebo. Subjects were classified into one of the following groups: cured (resolution of all clinical signs and symptoms of infection or sufficient improvement such that additional antimicrobial therapy was not required), failure (insufficient resolution of at least one of the initial signs and symptoms of infection, or the need for any additional or alternative antimicrobial therapy, or the need for surgical treatment of the infection), or indeterminate (assessment not possible for any reason).

Proportion of subjects with a clinical cure at EOT with BisEDT or placebo.

Proportion of subjects with a confirmed or presumed microbiological cure 2 weeks following the end of dosing, TOC. Subjects were classified into one of the following groups: confirmed eradication (all of the original pathogens were absent), presumed eradication (there was no available material for culture but the infection clinically responded to treatment), persistence (presence of a pathogen isolated at baseline), or indeterminate (inability to determine microbiological response).

Proportion of subjects with a confirmed or presumed microbiological cure at the EOT and EOS. At the EOS visit, additional classification groups included: colonization (isolation of a new organism that was not present on the initial culture but the wound was not clinically infected); reinfection (isolation of a new organism that was not present on the initial culture and the wound was clinically infected) or relapse (the same organism that was present on the initial culture was again isolated, after an intervening confirmed [sterile culture] or presumed [no material to culture] microbiological response and the wound was clinically infected).

Change from baseline in the Biofilm Score at EOT and TOC.

Proportion of subjects that underwent lower-extremity amputation involving the infected foot.

Proportion of subjects needing any infection-related surgery (ie, lower-extremity amputation, incision and drainage of a new abscess, or soft tissue or bone resection) after treatment had started.

Change from baseline in the 8-item DFI wound score at EOT, TOC, and EOS.

Percent reduction in ulcer size at EOS and each study visit.

Exploratory efficacy: The following clinical and microbiological exploratory efficacy outcomes were assessed:

Proportion of subjects with ulcer closure (ie, re-epithelialization of the wound) at EOS Duration of hospital stay Duration of systemic antibiotic therapy.

Clinical Response: The distribution of clinical response outcome categories (cured, failure, and indeterminate) are descriptively summarized by treatment group using counts and percentages at the TOC, EOT, and EOS visits.

At the TOC, EOT, and EOS visits, the cure rate (cured vs not cured) was analyzed using an Exact Logistic Regression model with covariates for treatment dose group, the 8-item baseline wound score, and the interaction of treatment group and baseline wound score. If the 8-item wound score and the interaction were not significant at the 10% level, they were removed from the model. If the 8-item wound score and the interaction were significant at the 10% level, they were kept in the model, and the estimated proportions are presented at different percentiles of the 8-item baseline wound score for each treatment group. The odds ratio and 90% 2-sided confidence interval (CI) are presented for each treatment group compared to placebo group. Analyses are presented for both the MITT and CE Populations.

Microbiological Response: The distribution of microbiological response outcome categories (confirmed eradication, presumed eradication, persistence, and indeterminate) are descriptively summarized by treatment group using counts and percentages at the TOC, EOT, and EOS visits. The eradication rate (confirmed+presumed vs the rest) was analyzed using the same methodology as clinical response. Analyses are presented for the ME Population.

Colonization, Reinfection, and Relapse: At the EOS visit, the number and percentage of subjects with a colonization, reinfection, or relapse are tabulated by treatment group for the ME Population.

Biofilm Response: The distribution of absolute scores at the EOT and TOC visits are descriptively summarized using counts and percentages by treatment group. Treatments were compared using the Cochran Mantel Haenszel mean score test statistic, and the p-value is presented. Additionally, shift tables showing individual subject changes from baseline to EOT and TOC visits are presented. Analyses are presented for the ME Population.

Wound Score and Size: The 8-item DFI wound score was calculated at baseline and each scheduled postbaseline visit. Descriptive statistics were used to summarize the scores at baseline, postbaseline, and change from baseline by treatment group.

A repeated measure mixed effect model was used to analyze the change from baseline in the 8-item DFI wound score. The least squares (LS) means for each treatment group at each scheduled postbaseline visit are presented along with their 90% 2-sided CIs.

The wound size component of the wound score is also summarized separately using descriptive statistics. The percent change from baseline in the wound size, as assessed by investigator measurement of the wound area, was analyzed using the same methodology as the 8-item DFI wound score. Percent reduction in ulcer wound size was analyzed using the ulcer wound size calculated from the 3-dimensional digital photographs using the same methodology.

Summary of Results:

Disposition of Subjects: In total, 53 (100.0%) subjects were randomized: 12 subjects in the 3 µg/cm² dose group, 13 subjects in the 7.5 µg/cm² dose group, 15 subjects in the 15 µg/cm² dose group, and 13 subjects in the placebo group. In total, 52 (98.1%) subjects received study drug, and 1 subject in the 7.5 µg/cm² dose group did not receive study drug.

Efficacy: Rates for clinical response of cured subjects at the TOC visit for the MITT Population were 66.7% of subjects in the 3 µg/cm² dose group, 50.0% of subjects in the 7.5 µg/cm² dose group, 40.0% of subjects in the 15 µg/cm² dose group, and 69.2% of subjects in the placebo group. Rates for a clinical response of cured at the EOT visit for the MITT Population were 75.0% of subjects in the 3 µg/cm² dose group, 50.0% of subjects in the 7.5 µg/cm² dose group, 73.3% of subjects in the 15 µg/cm² dose group, and 69.2% of subjects in the placebo group.

Rates for microbiological response of confirmed and presumed eradication at the TOC visit for the ME Population were 72.7% of subjects in the 3 µg/cm² dose group, 60.0% of subjects in the 7.5 µg/cm² dose group, 45.5% of subjects in the 15 µg/cm² dose group, and 75.0% of subjects in the placebo group.

Colonization and reinfection for the ME Population at the EOS visit occurred in 1 (9.1%) subject in the 3 µg/cm² dose group, 1 (10.0%) subject in the 7.5 µg/cm² dose group, 2 (18.2%) subjects in the 15 µg/cm² dose group, and 3 (25.0%) subjects in the placebo group. Relapse occurred in 1 (8.3%) subject in the placebo group. At the EOS visit, all BisEDT dose groups combined showed 4 (12.5%) subjects experienced a reinfection or relapse, compared to 4 (33.3%) subjects in the placebo group, an approximately one-third reduction with BisEDT.

In total, a baseline biofilm score of 2 or greater (which is suggestive of the presence of biofilm) for the ME Population was reported in 27 (61.4%) subjects: 9 (81.8%) subjects in the 3 µg/cm² dose group, 6 (60.0%) subjects in the 7.5 µg/cm² dose group, 5 (45.5%) subjects in the 15 µg/cm² dose group, and 7 (58.3%) subjects in the placebo group.

A biofilm score of 2 or greater was reported in 13 (43.3%) subjects in all dose groups combined and 7 (58.3%) subjects in the placebo group at the EOT visit for the ME Population. A biofilm score of 2 or greater at the TOC visit was reported in 17 (56.7%) subjects in all dose groups combined and 6 (50.0%) subjects in the placebo group for the ME Population.

The mean change in the 8-item DFI wound score from baseline to the EOT and TOC visits for the MITT Population was −6.9 and −7.7, respectively, in the 3 µg/cm² dose group; −6.7 and −8.0, respectively in the 7.5 µg/cm² dose group; −10.2 and −10.4, respectively, in the 15 µg/cm² dose group; and −8.9 and −9.0, respectively, in the placebo group.

The median percent reduction from baseline in ulcer wound size based on 3-dimensional photographs at the EOT, TOC, and EOS visits for the MITT Population was 32.8%, 71.3%, and 97.4%, respectively, in the 3 µg/cm² dose group; 62.4%, 88.6%, and 86.2%, respectively, in the 7.5 µg/cm² dose group; 17.3%, 69.1% and 78.7%, respectively, in the 15 µg/cm² dose group; and 6.1%, 26.5%, and 29.7%, respectively, in the placebo group. The median percent reduction in ulcer wound size from baseline based on 3-dimensional photographs at the EOT, TOC, and EOS visits was 41.5%, 78.2%, and 85.2%, respectively, for the MITT Population in all dose groups combined, and 6.1%, 26.5%, and 29.7%, respectively, for the placebo group, an approximately 3-fold increase compared to placebo.

The number and proportion of subjects with a >50% reduction in wound size based on 3-dimensional photographs at the TOC visit was 6 (54.5%) subjects in the 3 µg/cm² dose group, 6 (66.7%) subjects in the 7.5 µg/cm² dose group, 8 (57.1%) subjects in the 15 µg/cm² dose group, and 5 (38.5%) subjects in the placebo group. The number and proportion of subjects with a >50% reduction in wound size based on 3-dimensional photographs at the EOS visit was 6 (54.5%) subjects in the 3 µg/cm² dose group, 5 (62.5%) subjects in the 7.5 µg/cm² dose group, 9 (64.3%) subjects in the 15 µg/cm² dose group, and 5 (41.7%) subjects in the placebo group. The number and proportion of subjects with a >50% reduction in wound size based on 3-dimensional photographs at the TOC and EOS visits was 20 (58.8%) and 20 (60.6%), respectively, for the MITT Population in all dose groups combined, and 5 (38.5%) and 5 (41.7%), respectively, for the placebo group, an approximately 1.5-fold increase with BisEDT compared to placebo.

A total of 2 (15.4%) placebo subjects underwent an amputation related to the target infected ulcer compared to 1 (2.6%) of all BisEDT treated subjects, an approximately 6-fold reduction with BisEDT.

Conclusions: In this study, BisEDT was demonstrated to be safe and well tolerated, with very little systemic exposure.

Part 1 of the study was not designed to demonstrate efficacy of BisEDT as adjunct to standard of care, based on the small sample size. As part of standard of care, all subjects in the Safety Population in the study (with the exception of 1 subject in the 7.5 µg/cm² dose group) received systemic antibiotic therapy to treat DFI. Based on the limited data collected, the following observations can be made regarding BisEDT (adjunct to standard of care) and placebo (standard of care only):

The data did show BisEDT may be beneficial in the prevention of reinfection and relapse based on the effect seen at the EOS visit in which all dose groups combined showed 4 (12.5%) subjects experienced a reinfection or relapse, compared to 4 (33.3%) subjects in the placebo group, an approximately one-third reduction with BisEDT.

The data did show BisEDT may be beneficial in the prevention of target ulcer-specific amputations and target ulcer-specific infection-related surgical interventions when compared to placebo. A total of 2 (15.4%) placebo subjects underwent an amputation related to the target infected ulcer compared to 1 (2.6%) of all BisEDT treated subjects, an approximately 6-fold reduction with BisEDT.

The data did show BisEDT may be beneficial in the reduction of biofilm as shown at the EOT visit, where a biofilm score of 2 or greater was reported in 13 (43.3%) subjects in all dose groups combined and 7 (58.3%) subjects in the placebo group.

The data did show BisEDT may be beneficial as adjunct treatment for wound healing in moderate DFI subjects based on the effect seen in the percent reduction in ulcer size and the proportion of subjects with a >50% reduction in wound size. The proportion of subjects with a >50% reduction in wound size based on 3-dimensional photographs at the TOC and EOS visits was 58.8% and 60.6%, respectively, for the MITT Population in all dose groups combined, and 38.5% and 41.7%, respectively, for the placebo group, an approximately 1.5-fold increase with BisEDT compared to placebo. The median percent reduction in ulcer wound size from baseline based on 3-dimensional photographs at the TOC and EOS visits was 78.2% and 85.2%, respectively, for the MITT Population in all dose groups combined, and 26.5% and 29.7%, respectively, for the placebo group, an approximately 3-fold increase compared to placebo.

BisEDT may be beneficial in the prevention of target ulcer-specific amputations and target ulcer-specific infection-related surgical interventions when compared to placebo.

Furthermore, BisEDT may be beneficial in the prevention of reinfection and relapse. The EOS visit of all dose groups combined, showed that 4 (12.5%) subjects experienced a reinfection or relapse, compared to 4 (33.3%) subjects in the placebo group.

Additionally, BisEDT may be beneficial in the reduction of biofilms as shown at the EOT visit, where a biofilm score of 2 was reported in 13 (43.3%) subjects in all dose groups combined and 7 (58.3%) subjects in the placebo group.

BisEDT may also be beneficial as adjunct treatment for wound healing in moderate DFI subjects based on the effect seen in subjects with a >50% wound size reduction. The median percent reduction in ulcer wound size from baseline based on 3-dimensional photographs at the TOC and EOS visits was 78.2% and 85.2%, respectively, for the MITT population in all dose groups combined, and 26.5% and 29.7

Based on the limited whole blood concentrations data collected, BisEDT does not appear to exhibit any relevant systemic exposure.

Wound measurements (by Investigator):
Size ($cm^2$): The approximate area of the DFU was calculated based on the largest length and width of the ulcer.
Depth (mm): The depth was measured as the deepest apparent part of the wound using a sterile cotton-tipped wooden swab held 90 degrees to the wound and marked with a pen held parallel to the surface of the intact skin
Undermining (mm): Any tunneling, subepithelial tissue loss, or shearing were measured using a sterile cotton-tipped wooden swab and marked with a pen held perpendicular to the wooden swab.

Microbiologic assessment. Cultures were collected at baseline and as needed for the treatment of the subject. Tissue samples were shipped to a central laboratory where the presence of viable microorganisms was determined by standard microbiological culture methods and included speciation. Antimicrobial susceptibility testing was automatically performed on key pathogens for which antimicrobial resistance could impact therapy. Examples of key pathogens included: MRSA, methicillin-sensitive *Staphylococcus aureus* (MSSA), beta-hemolytic streptococci, enterococci, Enterobacteriaceae, *P aeruginosa*, and any other non-fermentative Gram-negative bacilli. Antimicrobial susceptibility testing on organisms not in the list of key pathogens may have also been conducted at the request of the Investigator or Sponsor. The susceptibility of bacterial isolates to BisEDT was also determined, but was not reported to investigators.

Efficacy Variables and Assessments.

Efficacy outcomes. The following clinical and microbiological efficacy outcomes were assessed:

Proportion of subjects with a clinical cure of infection 2 weeks following the end of dosing, TOC with BisEDT or placebo. Subjects were classified into one of the following groups: cured (resolution of all clinical signs and symptoms of infection or sufficient improvement such that additional antimicrobial therapy was not required), failure (insufficient resolution of at least one of the initial signs and symptoms of infection, or the need for any additional or alternative antimicrobial therapy, or the need for surgical treatment of the infection), or indeterminate (assessment not possible for any reason).

Proportion of subjects with a clinical cure at EOT with BisEDT or placebo.

Proportion of subjects with a confirmed or presumed microbiological cure 2 weeks following the end of dosing, TOC. Subjects were classified into one of the following groups: confirmed eradication (all of the original pathogens were absent), presumed eradication (there was no available material for culture but the infection clinically responded to treatment), persistence (presence of a pathogen isolated at baseline), or indeterminate (inability to determine microbiological response).

Proportion of subjects with a confirmed or presumed microbiological cure at the EOT and EOS. At the EOS visit, additional classification groups included: colonization (isolation of a new organism that was not present on the initial culture but the wound was not clinically infected); reinfection (isolation of a new organism that was not present on the initial culture and the wound was clinically infected) or relapse (the same organism that was present on the initial culture was again isolated, after an intervening confirmed [sterile culture] or presumed [no material to culture] microbiological response and the wound was clinically infected).

Change from baseline in the Biofilm Score at EOT and TOC.

Proportion of subjects that underwent lower-extremity amputation involving the infected foot.

Proportion of subjects needing any infection-related surgery (ie, lower-extremity amputation, incision & drainage of a new abscess, or soft tissue or bone resection) after treatment has started.

Change from baseline in the 8-item DFI wound score at EOT, TOC, and EOS.

Percent reduction in ulcer size at EOS and each study visit.

Exploratory outcomes: The following exploratory efficacy outcomes were assessed:

Proportion of subjects with ulcer closure (ie, re-epithelialization of the wound) at EOS Duration of hospital stay Duration of systemic antibiotic therapy Biofilm response: The following categories were used: score 0, no bacteria observed; 1, single individual cells; 2, small micro-colonies (~10 cells); 3, large micro-colonies (~100 cells); 4, continuous film; 5, thick continuous film. Subjects with no debridement material as a result of their DFI healing were given a score of 0. The distribution of absolute scores at the EOT and TOC visits are descriptively summarized using counts and percentages by treatment group. Treatments were compared using the Cochran Mantel Haenszel mean score test statistic, and the p-value is presented. Additionally, a shift table showing individual subject changes from baseline to EOT and TOC visits is presented. Analyses are presented for the ME Population.

Wound score and size: The 8-item DFI wound score was calculated at baseline and each scheduled postbaseline visit. Descriptive statistics were used to summarize the scores at baseline, postbaseline, and change from baseline by treatment group. A repeated measure mixed effect model was used to analyze the change from baseline in the 8-item DFI wound score. The change from baseline in the score was the response variable in the model with treatment group, time point, and treatment group by time point interaction as factors. The least squares (LS) means for each treatment group at each scheduled postbaseline visit are presented, along with their 90% 2-sided CIs. The wound size component of the wound score is also summarized separately using descriptive statistics. The percent change from baseline in the wound size, as assessed by Investigator measurement of the wound area, was analyzed using the same methodology as the 8-item DFI wound score. Percent reduction in ulcer wound size was analyzed using the ulcer wound size calculated from the 3-dimensional digital photographs using the same methodology. Analyses are presented for both the MITT and CE Populations.

Systemic Antibiotic Therapy: Table 3 summarizes the concomitant antibiotics for the MITT Population. The most common concomitant antibiotic was levofloxacin (49 [94.2%]subjects: 12 [100.0%] subjects in the 3 µg/cm² dose group, 10 [83.3%] subjects in the 7.5 µg/cm² dose group, 14 [93.3%] subjects in the 15 µg/cm² dose group, and 13 [100.0%] subjects in the placebo group); this was also the most common antibiotic used to treat DFI.

TABLE 3

Summary of Concomitant Antibiotics - Modified Intent-to-Treat Population

| ATC Classification Preferred Term | 3 µg/cm² (N = 12) n (%) | 7.5 µg/cm² (N = 12) n (%) | 15 µg/cm² (N = 15) n (%) | Placebo (N = 13) n (%) | Total (N = 52) n (%) |
|---|---|---|---|---|---|
| Any concomitant antibiotics | 12 (100.0) | 11 (91.7) | 15 (100.0) | 13 (100.0) | 51 (98.1) |
| Combinations of penicillins, including beta-lactamase inhibitors | 1 (8.3) | 1 (8.3) | 5 (33.3) | 3 (23.1) | 10 (19.2) |
| Augmentin/00756801/ | 1 (8.3) | 1 (8.3) | 4 (26.7) | 3 (23.1) | 9 (17.3) |
| PIP/TAZO | 0 (0.0) | 0 (0.0) | 1 (6.7) | 0 (0.0) | 1 (1.9) |
| Combinations of sulfonamides and trimethoprim, including derivatives | 2 (16.7) | 3 (25.0) | 5 (33.3) | 3 (23.1) | 13 (25.0) |
| Bactrim | 2 (16.7) | 3 (25.0) | 5 (33.3) | 3 (23.1) | 13 (25.0) |
| Corticosteroids and anti-infectives in combination | 0 (0.0) | 0 (0.0) | 0 (0.0) | 1 (7.7) | 1 (1.9) |
| Dexamethasone with neomycin/polymyxin B | 0 (0.0) | 0 (0.0) | 0 (0.0) | 1 (7.7) | 1 (1.9) |
| First-generation cephalosporins | 0 (0.0) | 1 (8.3) | 0 (0.0) | 0 (0.0) | 1 (1.9) |
| Cefalexin | 0 (0.0) | 1 (8.3) | 0 (0.0) | 0 (0.0) | 1 (1.9) |
| Fluoroquinolones | 12 (100.0) | 10 (83.3) | 14 (93.3) | 13 (100.0) | 49 (94.2) |
| Levofloxacin | 12 (100.0) | 10 (83.3) | 14 (93.3) | 13 (100.0) | 49 (94.2) |
| Glycopeptide antibacterials | 0 (0.0) | 0 (0.0) | 1 (6.7) | 0 (0.0) | 1 (1.9) |
| Vancomycin | 0 (0.0) | 0 (0.0) | 1 (6.7) | 0 (0.0) | 1 (1.9) |
| Lincosamides | 0 (0.0) | 0 (0.0) | 3 (20.0) | 1 (7.7) | 4 (7.7) |
| Clindamycin | 0 (0.0) | 0 (0.0) | 2 (13.3) | 0 (0.0) | 2 (3.8) |
| Clindamycin hydrochloride | 0 (0.0) | 0 (0.0) | 1 (6.7) | 1 (7.7) | 2 (3.8) |
| Other antibacterials | 1 (8.3) | 0 (0.0) | 0 (0.0) | 0 (0.0) | 1 (1.9) |
| Linezolid | 1 (8.3) | 0 (0.0) | 0 (0.0) | 0 (0.0) | 1 (1.9) |
| Other antibiotics for topical use | 1 (8.3) | 1 (8.3) | 1 (6.7) | 0 (0.0) | 3 (5.8) |
| Bacitracin | 0 (0.0) | 0 (0.0) | 1 (6.7) | 0 (0.0) | 1 (1.9) |
| Neotracin/00038301/ | 1 (8.3) | 1 (8.3) | 0 (0.0) | 0 (0.0) | 2 (3.8) |
| Tetracyclines | 0 (0.0) | 0 (0.0) | 1 (6.7) | 1 (7.7) | 2 (3.8) |
| Doxycycline | 0 (0.0) | 0 (0.0) | 0 (0.0) | 1 (7.7) | 1 (1.9) |
| Minocycline hydrochloride | 0 (0.0) | 0 (0.0) | 1 (6.7) | 0 (0.0) | 1 (1.9) |
| Third-generation cephalosporins | 1 (8.3) | 0 (0.0) | 2 (13.3) | 0 (0.0) | 3 (5.8) |

TABLE 3-continued

Summary of Concomitant Antibiotics - Modified Intent-to-Treat Population

| ATC Classification<br>Preferred Term | 3 µg/cm² (N = 12) n (%) | 7.5 µg/cm² (N = 12) n (%) | 15 µg/cm² (N = 15) n (%) | Placebo (N = 13) n (%) | Total (N = 52) n (%) |
|---|---|---|---|---|---|
| Ceftriaxone | 1 (8.3) | 0 (0.0) | 0 (0.0) | 0 (0.0) | 1 (1.9) |
| Ceftriaxone sodium | 0 (0.0) | 0 (0.0) | 2 (13.3) | 0 (0.0) | 2 (3.8) |

Coding was based on WHO Drug Dictionary (Sep 2016E B2).
Percentage was calculated using the number of subjects in the column heading as the denominator.
Concomitant antibiotics are antibiotics that were taken on or after the first dose of study drug.
ATC = Anatomical Therapeutic Chemical; PIP/TAZO = Piperacillin/Tazobactam; WHO = World Health Organization.

Concomitant Medications: For the MITT Population, all 52 (100.0%) subjects were taking at least 1 concomitant medication. The most commonly reported non-antibiotic concomitant medications were the following:

Insulin glargine—7 (58.3%) subjects in the 3 µg/cm² dose group, 4 (33.3%) subjects in the 7.5 µg/cm² dose group, 8 (53.3%) subjects in the 15 µg/cm² dose group, and 9 (69.2%) subjects in the placebo group Lisinopril—7 (58.3%) subjects in the 3 µg/cm² dose group, 4 (33.3%) subjects in the 7.5 µg/cm² dose group, 6 (40.0%) subjects in the 15 µg/cm² dose group, and 6 (46.2%) subjects in the placebo group Metformin—3 (25.0%) subjects in the 3 µg/cm² dose group, 5 (41.7%) subjects in the 7.5 µg/cm² dose group, 7 (46.7%) subjects in the 15 µg/cm² dose group, and 2 (15.4%) subjects in the placebo group Treatment Compliance: For the MITT Population, overall, 3 (5.8%) subjects had 1 missed dose (2 [16.7%] subjects in the 3 µg/cm² dose group and 1 [7.7%] subject in the placebo group), 1 (1.9%) subject had 2 missed doses (1 [8.3%] subject in the 3 µg/cm² dose group), and 1 (1.9%) subject had 3 missed doses (1 [8.3%] subject in the 3 µg/cm² dose group).

Efficacy and Pharmacokinetic Results:

Clinical response: Clinical response at the Test of Cure visit. Table 4 presents an analysis of clinical response at the TOC visit for the MITT population. No difference between treatment groups was observed.

TABLE 4

Analysis of Clinical Response at Test of Cure Visit - Modified Intent-to-Treat Population

| Clinical Response | 3 µg/cm² (N = 12) n (%) | 7.5 µg/cm² (N = 12) n (%) | 15 µg/cm² (N = 15) n (%) | Placebo (N = 13) n (%) |
|---|---|---|---|---|
| Cured | 8 (66.7) | 6 (50.0) | 6 (40.0) | 9 (69.2) |
| Failure | 4 (33.3) | 5 (41.7) | 9 (60.0) | 4 (30.8) |
| Indeterminate | 0 (0.0) | 1 (8.3) | 0 (0.0) | 0 (0.0) |
| Treatment Comparison (BisEDT vs Placebo) [1] | | | | |
| Odds Ratio | 0.61 | 0.41 | 0.42 | |
| 90% CI | (0.09, 3.75) | (0.06, 2.38) | (0.05, 2.13) | |

Percentages were calculated using the number of subjects in the column heading as the denominator.
Treatment comparison was between each treatment dose group and placebo for the cured rate (cured vs not cured). Odds ratio and 90% CI were obtained from an exact logistic regression model with covariates for treatment dose group and the 8-item baseline wound score.
CI = confidence interval; vs = versus.

Clinical response at the End of Treatment visit: Table 5 presents an analysis of clinical response at the EOT visit for the MITT Population. No difference between treatment groups was observed.

TABLE 5

Analysis of Clinical Response at End of Treatment Visit - Modified Intent-to-Treat Population

| Clinical Response | 3 µg/cm² (N = 12) n (%) | 7.5 µg/cm² (N = 12) n (%) | 15 µg/cm² (N = 15) n (%) | Placebo (N = 13) n (%) |
|---|---|---|---|---|
| Cured | 9 (75.0) | 6 (50.0) | 11 (73.3) | 9 (69.2) |
| Failure | 3 (25.0) | 5 (41.7) | 4 (26.7) | 4 (30.8) |
| Indeterminate | 0 (0.0) | 1 (8.3) | 0 (0.0) | 0 (0.0) |
| Treatment Comparison (BisEDT vs Placebo) [1] | | | | |
| Odds Ratio | 0.95 | 0.42 | 1.65 | |
| 90% CI | (0.14, 6.64) | (0.07, 2.30) | (0.29, 9.98) | |

Percentages were calculated using the number of subjects in the column heading as the denominator.
Treatment comparison was between each treatment dose group and placebo for the cured rate (cured vs not cured). Odds ratio and 90% CI were obtained from an exact logistic regression model with covariates for treatment dose group and the 8-item baseline wound score.
CI = confidence interval; vs = versus.

Microbiological response Microbiological response at the Test of Cure visit. Table 6 presents an analysis of microbiological response at the TOC visit for the ME Population. No difference between treatment groups was observed.

TABLE 6

Analysis of Microbiological Response at Test of Cure Visit - Microbiologically Evaluable Population

| Microbiological Response | 3 µg/cm² (N = 11) n (%) | 7.5 µg/cm² (N = 10) n (%) | 15 µg/cm² (N = 11) n (%) | Placebo (N = 12) n (%) |
|---|---|---|---|---|
| Confirmed eradication | 4 (36.4) | 2 (20.0) | 4 (36.4) | 6 (50.0) |
| Presumed eradication | 4 (36.4) | 4 (40.0) | 1 (9.1) | 3 (25.0) |
| Persistence | 3 (27.3) | 3 (30.0) | 3 (27.3) | 1 (8.3) |
| Indeterminate | 0 (0.0) | 1 (10.0) | 3 (27.3) | 2 (16.7) |
| Confirmed + presumed eradication | 8 (72.7) | 6 (60.0) | 5 (45.5) | 9 (75.0) |
| Treatment Comparison (BisEDT vs Placebo) [1] | | | | |
| Odds Ratio | 0.89 | 0.52 | 0.29 | |
| 90% CI | (0.13, 6.34) | (0.07, 3.26) | (0.04, 1.66) | |

Percentages were calculated using the number of subjects in the column heading as the denominator.
Treatment comparison was between each treatment dose group and placebo for the eradication rate (confirmed + presumed vs the rest). Odds ratio and 90% CI were obtained from an exact logistic regression model with covariate for treatment dose group.
CI = confidence interval; vs = versus.

Exploratory outcomes: Microbiological response at the End of Treatment visit. Table 7 presents an analysis of microbiological response at the EOT visit for the ME Population. No difference between treatment groups was observed.

TABLE 7

Analysis of Microbiological Response at End of Treatment Visit - Microbiologically Evaluable Population

| Microbiological Response | 3 µg/cm$^2$ (N = 11) n (%) | 7.5 µg/cm$^2$ (N = 10) n (%) | 15 µg/cm$^2$ (N = 11) n (%) | Placebo (N = 12) n (%) |
|---|---|---|---|---|
| Confirmed eradication | 3 (27.3) | 3 (30.0) | 6 (54.5) | 6 (50.0) |
| Presumed eradication | 3 (27.3) | 3 (30.0) | 2 (18.2) | 2 (16.7) |
| Persistence | 5 (45.5) | 3 (30.0) | 3 (27.3) | 4 (33.3) |
| Indeterminate | 0 (0.0) | 1 (10.0) | 0 (0.0) | 0 (0.0) |
| Confirmed + presumed eradication | 6 (54.5) | 6 (60.0) | 8 (72.7) | 8 (66.7) |
| Treatment Comparison (BisEDT vs Placebo) [1] | | | | |
| Odds Ratio | 0.61 | 0.76 | 1.32 | |
| 90% CI | (0.11, 3.34) | (0.13, 4.52) | (0.21, 8.81) | |

Percentages were calculated using the number of subjects in the column heading as the denominator.
Treatment comparison was between each treatment dose group and placebo for the eradication rate (confirmed + presumed vs the rest). Odds ratio and 90% CI were obtained from an exact logistic regression model with covariate for treatment dose group.
CI = confidence interval; vs = versus.

Microbiological response at the End of Study visit: Table 8 presents an analysis of microbiological response at the EOS visit for the ME Population. No difference between treatment groups was observed.

TABLE 8

Analysis of Microbiological Response at End of Study Visit - Microbiologically Evaluable Population

| Microbiological Response | 3 µg/cm$^2$ (N = 11) n (%) | 7.5 µg/cm$^2$ (N = 10) n (%) | 15 µg/cm$^2$ (N = 11) n (%) | Placebo (N = 12) n (%) |
|---|---|---|---|---|
| Confirmed eradication | 2 (18.2) | 2 (20.0) | 4 (36.4) | 6 (50.0) |
| Presumed eradication | 6 (54.5) | 2 (20.0) | 1 (9.1) | 3 (25.0) |
| Persistence | 3 (27.3) | 4 (40.0) | 1 (9.1) | 2 (16.7) |
| Indeterminate | 0 (0.0) | 2 (20.0) | 5 (45.5) | 1 (8.3) |
| Confirmed + presumed eradication | 8 (72.7) | 4 (40.0) | 5 (45.5) | 9 (75.0) |
| Treatment Comparison (BisEDT vs Placebo) [1] | | | | |
| Odds Ratio | 0.89 | 0.24 | 0.29 | |
| 90% CI | (0.13, 6.34) | (0.03, 1.41) | (0.04, 1.66) | |

Percentages were calculated using the number of subjects in the column heading as the denominator.
Treatment comparison was between each treatment dose group and placebo for the eradication rate (confirmed + presumed vs the rest). Odds ratio and 90% CI were obtained from an exact logistic regression model with covariate for treatment dose group.
CI = confidence interval; vs = versus.

Table 9 summarizes colonization, reinfection, and relapse at the EOS visit for the ME Population. No difference between treatment groups was observed. When looking at all dose groups combined, 4 (12.50%) subjects experienced a reinfection or relapse, compared to 4 (33.30%) subjects in the placebo group, an approximately one-third reduction with BisEDT.

TABLE 9

Summary of Colonization, Reinfection, and Relapse at End of Study Visit - Microbiologically Evaluable Population

| Category | 3 µg/cm$^2$ (N = 11) n (%) | 7.5 µg/cm$^2$ (N = 10) n (%) | 15 µg/cm$^2$ (N = 11) n (%) | Placebo (N = 12) n (%) |
|---|---|---|---|---|
| Colonization | 1 (9.1) | 1 (10.0) | 2 (18.2) | 3 (25.0) |
| Reinfection | 1 (9.1) | 1 (10.0) | 2 (18.2) | 3 (25.0) |
| Relapse | 0 (0.0) | 0 (0.0) | 0 (0.0) | 1 (8.3) |

Percentages were calculated using the number of subjects in the column heading as the denominator.
Colonization was defined as isolation of a new organism that was not present on the initial culture, but the wound was not clinically infected.
Reinfection was defined as isolation of a new organism that was not present on the initial culture, and the wound was clinically infected.
Relapse was defined as the same organism that was present on the initial culture was again isolated, after an intervening confirmed (sterile culture) or presumed (no material to culture) microbiological response, and the wound was clinically infected.

Biofilm score. Biofilm score at the Test of Cure visit: Table 10 presents an analysis of biofilm response at the TOC visit for the ME Population. In total, a baseline biofilm score of 2 or greater (which is suggestive of the presence of biofilm) was reported in 27 (61.4%) subjects: 9 (81.8%) subjects in the 3 µg/cm$^2$ dose group, 6 (60.0%) subjects in the 7.5 µg/cm$^2$ dose group, 5 (45.5%) subjects in the 15 µg/cm$^2$ dose group, and 7 (58.3%) subjects in the placebo group. A biofilm score of 2 or greater at the TOC visit was reported in 17 (56.7%) subjects in all dose groups combined and 6 (50.0%) subjects in the placebo group for the ME Population. No difference in biofilm response at the TOC visit between treatment groups was observed for the ME Population.

TABLE 10

Analysis of Biofilm Response at Test of Cure Visit - Microbiologically Evaluable Population

| Score | 3 µg/cm$^2$ (N = 11) n (%) | 7.5 µg/cm$^2$ (N = 10) n (%) | 15 µg/cm$^2$ (N = 11) n (%) | Placebo (N = 12) n (%) |
|---|---|---|---|---|
| N' | 11 | 9 | 10 | 12 |
| 0 | 3 (27.3) | 5 (55.6) | 4 (40.0) | 5 (41.7) |
| 1 | 0 (0.0) | 0 (0.0) | 1 (10.0) | 1 (8.3) |
| 2 | 2 (18.2) | 2 (22.2) | 2 (20.0) | 4 (33.3) |
| 3 | 2 (18.2) | 1 (11.1) | 0 (0.0) | 1 (8.3) |
| 4 | 2 (18.2) | 0 (0.0) | 2 (20.0) | 0 (0.0) |
| 5 | 2 (18.2) | 1 (11.1) | 1 (10.0) | 1 (8.3) |
| Treatment comparison (BisEDT vs Placebo) [1] | | | | |
| p-value | 0.1321 | 0.9075 | 0.6003 | |

Percentage was calculated using N' as the denominator, where N' was the number of subjects with non-missing biofilm score at the TOC visit.
Score 0 = no bacteria observed, 1 = single individual cells, 2 = small micro-colonies (~10 cells), 3 = large micro-colonies (~100 cells), 4 = continuous film, 5 = thick continuous film. Subjects with no debridement material as a result of their DFI healing were given a score of 0.
p-value was obtained from the CMH mean score test.
CMH = Cochran Mantel Haenszel; DFI = diabetic foot infection; TOC = Test of Cure; vs = versus.

Biofilm score at the End of Treatment visit: Table 11 presents an analysis of biofilm response at the EOT visit for the ME Population. A biofilm score of 2 or greater (which is suggestive of the presence of biofilm) at the EOT visit was reported in 13 (43.31) subjects in all dose groups combined and 7 (58.3%) subjects in the placebo group for the ME Population. No difference in biofilm response at the EOT visit between treatment groups was observed for the ME Population.

TABLE 11

Analysis of Biofilm Response at End of Treatment
Visit - Microbiologically Evaluable Population

| Score | 3 μg/cm² (N = 11) n (%) | 7.5 μg/cm² (N = 10) n (%) | 15 μg/cm² (N = 11) n (%) | Placebo (N = 12) n (%) |
|---|---|---|---|---|
| N' | 11 | 8 | 11 | 12 |
| 0 | 3 (27.3) | 2 (25.0) | 5 (45.5) | 2 (16.7) |
| 1 | 2 (18.2) | 2 (25.0) | 3 (27.3) | 3 (25.0) |
| 2 | 1 (9.1) | 1 (12.5) | 1 (9.1) | 3 (25.0) |
| 3 | 3 (27.3) | 1 (12.5) | 1 (9.1) | 2 (16.7) |
| 4 | 0 (0.0) | 1 (12.5) | 1 (9.1) | 2 (16.7) |
| 5 | 2 (18.2) | 1 (12.5) | 0 (0.0) | 0 (0.0) |
| Treatment comparison (BisEDT vs Placebo) [1] | | | | |
| p-value | 0.7936 | 0.9055 | 0.1606 | |

Percentage was calculated using N' as the denominator, where N' was the number of subjects with non-missing biofilm score at the EOT visit.
Score 0 = no bacteria observed, 1 = single individual cells, 2 = small micro-colonies (~10 cells), 3 = large micro-colonies (~100 cells), 4 = continuous film, 5 = thick continuous film. Subjects with no debridement material as a result of their DFI healing were given a score of 0.
P-value was obtained from the CMH mean score test.
CMH = Cochran Mantel Haenszel; DFI = diabetic foot infection; EOT = End of Treatment; vs = versus.

Lower-extremity amputations: The number and proportion of subjects with lower extremity amputations involving the infected foot for the MITT Population was 0 (0.0%) subjects in the 3 μg/cm² dose group, 1 (8.3%) subject in the 7.5 μg/cm² dose group, 1 (6.7%) subject in the 15 μg/cm² dose group, and 2 (15.4%) subjects in the placebo group. In the 7.5 μg/cm² dose group, Subject 001-026 had an amputation related to a new infection of nontarget ulceration of the lateral forefoot. In the 15 μg/cm² dose group, Subject 001-031 had amputations related to worsening of the target ulcer infection. In the placebo group, Subject 001-013 had amputations related to a new diagnosis of osteomyelitis of target ulceration of the right foot. In the placebo group, Subject 006-001 had an amputation related to worsening of osteomyelitis of target ulceration of the left foot. When all dose groups were combined, 1 of 39 (2.56%) subjects had a lower extremity amputation related to the target infected ulcer, compared to 2 of 13 (15.4%) subjects in the placebo group.

Infection-related surgery: The number and proportion of subjects that underwent infection related surgical interventions for the MITT Population was 0 (0.0%) subjects in the 3 μg/cm² dose group, 1 (8.3%) subject in the 7.5 μg/cm² dose group, 1 (6.7%) subject in the 15 μg/cm² dose group, and 2 (15.4%) subjects in the placebo group.

8-Item DFI wound score: Table 12 summarizes the 8-item DFI wound scores and changes from baseline by visit for the MITT Population.

TABLE 12

Summary of 8-Item Diabetic Foot Infection Wound Score and Change
From Baseline by Visit - Modified Intent-to-Treat Population

| Visit Statistic | 3 μg/cm² (N = 12) | 7.5 μg/cm² (N = 12) | 15 μg/cm² (N = 15) | Placebo (N = 13) |
|---|---|---|---|---|
| Baseline [1] | | | | |
| n | 12 | 12 | 15 | 13 |
| Mean (SD) | 12.3 (2.23) | 14.0 (4.37) | 16.2 (2.78) | 14.2 (3.85) |
| EOT | | | | |
| n | 12 | 11 | 15 | 13 |
| Mean (SD) | 5.4 (3.70) | 7.3 (4.54) | 6.0 (4.38) | 5.2 (3.11) |
| Change from baseline at EOT | | | | |
| n [2] | 12 | 11 | 15 | 13 |
| Mean (SD) | −6.9 (3.03) | −6.7 (5.53) | −10.2 (3.45) | −8.9 (3.57) |
| TOC | | | | |
| n | 11 | 9 | 14 | 13 |
| Mean (SD) | 4.3 (2.61) | 6.3 (4.36) | 5.6 (3.86) | 5.2 (4.63) |
| Change from baseline at TOC | | | | |
| n [2] | 11 | 9 | 14 | 13 |
| Mean (SD) | −7.7 (2.76) | −8.0 (6.28) | −10.4 (3.37) | −9.0 (4.43) |

Baseline was defined as the last measurement or assessment prior to the first dose of study drug.
n was the number of subjects with both baseline and postbaseline measurements.
EOT = End of Treatment; SD = standard deviation; TOC = Test of Cure.

Ulcer size: Table 13 presents a summary of ulcer wound size based on 3-dimensional digital photographs and percent change from baseline by visit for the MITT Population. The median percent reduction from baseline in ulcer wound size based on 3-dimensional photographs at the EOT, TOC, and LOS visits for the MITT Population was 32.8%, 71.3%, and 97.4%, respectively, in the 3 μg/cm² dose group; 62.400, 88.600, and 86.2%, respectively, in the 7.5 μg/cm² dose group; 17.3%, 69.1% and 78.7%, respectively, in the 15 μg/cm² dose group; and 6.1%, 26.5%, and 29.7%, respectively, in the placebo group. The median percent reduction in ulcer wound size from baseline based on 3-dimensional photographs at the LOT, TOC, and LOS visits was 41.5%, 78.200, and 85.2%, respectively, for the MITT Population in all dose groups combined, and 6.1%, 26.500 and 29.7%, respectively, for the placebo group, an approximately 3-fold increase compared to placebo.

TABLE 13

Summary of Ulcer Wound Size Based on Digital Photographs and Percent
Change from Baseline by Visit - Modified Intent-to-Treat Population

| Parameter (unit) Visit Statistic | 3 μg/cm² (N = 12) | 7.5 μg/cm² (N = 12) | 15 μg/cm² (N=15) | Placebo (N = 13) |
|---|---|---|---|---|
| Ulcer wound size (cm²) Baseline [1] | | | | |
| n | 12 | 12 | 15 | 13 |
| Median (minimum, maximum) | 0.394 (0.00, 4.21) | 0.795 (0.08, 42.15) | 1.814 (0.03, 21.94) | 0.888 (0.03, 12.18) |

TABLE 13-continued

Summary of Ulcer Wound Size Based on Digital Photographs and Percent Change from Baseline by Visit - Modified Intent-to-Treat Population

| Parameter (unit) Visit Statistic | 3 µg/cm² (N = 12) | 7.5 µg/cm² (N = 12) | 15 µg/cm² (N=15) | Placebo (N = 13) |
|---|---|---|---|---|
| EOT | | | | |
| n | 12 | 11 | 15 | 13 |
| Median (minimum, maximum) | 0.239 (0.00, 4.65) | 0.449 (0.00, 25.06) | 0.899 (0.00, 29.62) | 1.042 (0.00, 11.44) |
| Percent change from baseline at EOT | | | | |
| n [2] | 12 | 11 | 15 | 13 |
| Median (minimum, maximum) | −32.79 (−100.0, 315.1) | −62.42 (−100.0, 940.9) | −17.26 (−100.0, 1008.4) | −6.10 (−100.0, 525.6) |
| TOC | | | | |
| n | 11 | 9 | 14 | 13 |
| Median (minimum, maximum) | 0.179 (0.00, 2.63) | 0.116 (0.00, 7.53) | 0.574 (0.00, 26.60) | 1.526 (0.00, 8.96) |
| Percent change from baseline at TOC | | | | |
| n [2] | 11 | 9 | 14 | 13 |
| Median (minimum, maximum) | −71.27 (−100.0, 135.1) | −88.58 (−100.0, 2083.2) | −69.08 (−100.0, 523.0) | −26.45 (−100.0, 475.8) |
| EOS | | | | |
| n | 11 | 8 | 14 | 12 |
| Median (minimum, maximum) | 0.066 (0.00, 2.35) | 0.336 (0.00, 4.99) | 0.265 (0.00, 27.17) | 0.890 (0.00, 10.64) |
| Percent change from baseline at EOS | | | | |
| n [2] | 11 | 8 | 14 | 12 |
| Median (minimum, maximum) | −97.36 (−100.0, 109.4) | −86.19 (−100.0, 1681.2) | −78.73 (−100.0, 298.5) | −29.67 (−100.0, 627.2) |

Baseline was defined as the last measurement or assessment prior to the first dose of study drug.
n was the number of subjects with both baseline and postbaseline measurements.
EOS = End of Study; EOT = End of Treatment; SD = standard deviation; TOC = Test of Cure.

Table 14 presents an ad-hoc analysis of the proportion of subjects with a >50% reduction in wound size based on 3-dimensional digital photographs by visit for the MITT Population

TABLE 14

Analysis of Proportion of Subjects with a >50% Reduction in Wound Size Based on Digital Photographs by Visit - Modified Intent-to-Treat Population

| Visit Statistics | 3 µg/cm² (N = 12) n/N' (%) | 7.5 µg/cm² (N = 12) n/N' (%) | 15 µg/cm² (N = 15) n/N' (%) | Placebo (N = 13) n/N' (%) | Total BisEDT (N = 39) n/N' (%) |
|---|---|---|---|---|---|
| EOT | | | | | |
| Subjects with a >50% reduction in wound size | 5/12 (41.7) | 6/11 (54.5) | 5/15 (33.3) | 3/13 (23.1) | 16/38 (42.1) |
| Treatment Comparison (BisEDT vs Placebo) [1] | | | | | |
| Difference | 0.19 | 0.31 | 0.10 | | 0.19 |
| 90% CI | (−0.17, 0.49) | (−0.04, 0.61) | (−0.21, 0.40) | | (−0.08, 0.44) |
| p-value | 0.4110 | 0.2060 | 0.6860 | | 0.3232 |

TABLE 14-continued

Analysis of Proportion of Subjects with a >50% Reduction in Wound Size
Based on Digital Photographs by Visit - Modified Intent-to-Treat Population

| Visit Statistics | 3 µg/cm² (N = 12) n/N' (%) | 7.5 µg/cm² (N = 12) n/N' (%) | 15 µg/cm² (N = 15) n/N' (%) | Placebo (N = 13) n/N' (%) | Total BisEDT (N = 39) n/N' (%) |
|---|---|---|---|---|---|
| TOC | | | | | |
| Subjects with a >50% reduction in wound size | 6/11 (54.5) | 6/9 (66.7) | 8/14 (57.1) | 5/13 (38.5) | 20/34 (58.8) |
| Treatment Comparison (BisEDT vs Placebo) [1] | | | | | |
| Difference | 0.16 | 0.28 | 0.19 | | 0.20 |
| 90% CI | (−0.19, 0.48) | (−0.09, 0.60) | (−0.15, 0.49) | | (−0.07, 0.46) |
| p-value | 0.6824 | 0.3870 | 0.4495 | | 0.3279 |
| EOS | | | | | |
| Subjects with a >50% reduction in wound size | 6/11 (54.5) | 5/8 (62.5) | 9/14 (64.3) | 5/12 (41.7) | 20/33 (60.6) |
| Treatment Comparison (BisEDT vs Placebo) [1] | | | | | |
| Difference | 0.13 | 0.21 | 0.23 | | 0.19 |
| 90% CI | (−0.24, 0.47) | (−0.19, 0.56) | (−0.12, 0.53) | | (−0.09, 0.45) |
| p-value | 0.6843 | 0.6499 | 0.4312 | | 0.3200 |

Percentages were calculated using N' as the denominator, where N' was the number of subjects with both baseline and post-baseline measurements at the specific visit.
The treatment difference estimates, the exact 90% 2-sided CI, and p-values were obtained from Fisher's Exact Test.
CI = confidence interval; EOS = End of Study; EOT = End of Treatment; TOC = Test of Cure; vs = versus.

Exploratory Efficacy Evaluations

Ulcer closure: Ulcer closure at the End of Study visit. Complete ulcer closure at the EOS visit for the MITT Population occurred in 3 (25.0%) subjects in the 3 µg/cm² dose group, 2 (16.7%) subjects in the 7.5 µg/cm² dose group, 2 (13.3%) subjects in the 15 µg/cm² dose group, and 3 (23.1%) subjects in the placebo group.

Duration of systemic antibiotic therapy: For subjects in the MITT Population who required systemic antibiotic therapy, the mean number of days was:
  3 µg/cm² dose group: 12 subjects, 22.8 days
  7.5 µg/cm² dose group: 11 subjects, 20.0 days
  15 µg/cm² dose group: 15 subjects, 29.5 days
  Placebo group: 13 subjects, 27.6 days Pharmacokinetic Evaluation: Blood concentration of bismuth was only detected in the 15 µg/cm² dose group during the course of the study. The mean bismuth concentration by day for the PK Concentration Population included: 8 subjects on Day 1 predose (only 2 subjects with detectable levels of 0.582 and 0.548 ng/mL, hypothesized to be from undisclosed use of bismuth containing medications or from dressings containing bismuth, such as Xeroform®, as blood was collected before treatment with BisEDT); 8 subjects on Day 3 predose (only 1 subject with a detectable level of 0.525 ng/mL); 8 subjects on Day 5 predose (only 1 subject with a detectable level of 0.701 ng/mL); and 8 subjects on Day 8 predose (only 1 subject with a detectable level of 0.513 ng/mL). Bismuth was not detected beyond Day 8 for any subject in any treatment group. Bismuth levels were not measured in samples that were erroneously processed to plasma by the 1 site that enrolled the majority of the subjects in the PK study, as bismuth levels are expected to be 15 to 20 times lower in plasma samples compared to whole blood samples and would be well below the lower limit of quantitation for the assay method; no PK parameters were calculated.

Efficacy and Pharmacokinetic Conclusions: Part 1 of the study was not designed to demonstrate efficacy of BisEDT as adjunct to standard of care, based on the small sample size. As part of standard of care, all subjects in the Safety Population in the study (with the exception of 1 subject in the 7.5 µg/cm² dose group) received systemic antibiotic therapy to treat DFI. Based on the limited data collected, the following observations can be made regarding BisEDT (adjunct to standard of care) and placebo (standard of care only):

The data showed that BisEDT may be beneficial in the prevention of reinfection and relapse based on the effect seen at the EOS visit in which all dose groups combined, showed 4 (12.5%) subjects experienced a reinfection or relapse, compared to 4 (33.3%) subjects in the placebo group, an approximately one-third reduction with BisEDT.

The data also showed that BisEDT may be beneficial in the prevention of target ulcer-specific amputations and target ulcer-specific infection-related surgical interventions when compared to placebo. A total of 2 (15.4%) placebo subjects underwent an amputation related to the target infected ulcer compared to 1 (2.6%) of all BisEDT treated subjects, an approximately 6-fold reduction with BisEDT.

Additionally, BisEDT may be beneficial in the reduction of biofilm as shown at the EOT visit, where a biofilm score of 2 or greater was reported in 13 (43.3%) subjects in all dose groups combined and 7 (58.3%) subjects in the placebo group.

The data did show BisEDT may be beneficial as an adjunct treatment for wound healing in moderate DFI subjects based on the effect seen in the percent reduction in ulcer size and the proportion of subjects with a >50% reduction in wound size. The proportion of subjects with a >50% reduction in wound size based on 3-dimensional photographs at the TOC and EOS visits was 58.8% and 60.6%, respectively, for the MITT Population in all dose groups combined, and 38.5% and 41.7%, respectively, for the placebo group, an approximately 1.5-fold increase with BisEDT compared to placebo. The median percent reduction in ulcer wound size from baseline based on 3-dimensional photographs at the TOC and EOS visits was 78.2% and 85.2%, respectively, for the MITT Population in all dose groups combined, and 26.5% and 29.7%, respectively, for the placebo group, an approximately 3-fold increase compared to placebo.

Based on the limited whole blood concentrations data collected, BisEDT does not appear to exhibit any relevant systemic exposure.

Safety Conclusions: No safety signals were identified. Doses of 3, 7.5, and 15 µg/cm$^2$ were all well tolerated. None of the TEAEs and SAEs occurring in the study were considered related to study drug.

Discussion and Overall Conclusions

Discussion: The objective of Part 1 of the study was met and all 3 doses of BisEDT were demonstrated to be safe and well tolerated. In addition, the PK concentration data collected indicated limited systemic exposure, suggesting that BisEDT is well suited for topical administration. While efficacy data were collected in Part 1, due to the small sample size, no definitive efficacy conclusions can be drawn from the data. However, based on the efficacy variables collected, BisEDT may have the potential to aid in the reduction of wound size and prevent reinfection and relapse, prevent target ulcer-specific amputations and infection-related surgical interventions, and reduce the amount of biofilm present at the EOT visit, and aid in the reduction of wound size in infected DFUs.

Overall Conclusions: In this study, BisEDT was demonstrated to be safe and well tolerated, with very little systemic exposure.

Example 8: Studies on Processing Conditions on BisEDT Particle Size Distribution It was observed that careful control of the reaction temperature and the rate of 1,2 ethanedithiol addition had pronounced impact on the BisEDT particle size distribution. Representative syntheses are shown below for BisEDT synthesized at 20° C. with a 1.25 hour addition of 1,2-ethane via syringe pump and BisEDt synthesized at 15° C. with a 1 hour addition of 1,2-ethane via syringe pump. Table 15 below shows that temperature conditions play a critical role in particle size distribution, with processing temperatures in the range of 20-30° C. providing BisEDT particles that are both small and uniform in particle size (such as a D90 below 2 microns).

Representative synthesis of BisEDT at 20° C. with 1.25 hour addition of thiol via syringe pump, and polypropylene cloth for filtration: BisEDT synthesis was performed on 10-g scale. To a 1-L jacketed reactor was charged USP water (480 mL, 48 vol), followed by 70% HNO$_3$ (34 mL, 3.4 vol). A solution of bismuth subnitrate (10 g, 6.84 mmols) in water (43 mL, 4.3 vol) and 70% HNO$_3$ (14 mL, 1.4 vol) was added at 20° C. The reaction mixture was cooled to 15° C. for addition of 95% Ethanol. The 95% ethanol (180 mL, 18 vol) was then added slowly. (Ethanol addition is exothermic, temperature reached 22° C.). The temperature was then adjusted back to 20° C. This was followed by dropwise addition of 1,2 ethanedithiol (4.3 mL, 7.5 mmols in 95% ethanol in 94 mL, 9.4 vol) over a period of 1.25 hour with the batch temperature at 20° C. during which time it turned into a yellow suspension. The reaction was stirred at 20° C. overnight. The reaction mixture was filtered through polypropylene cloth and washed with 95% ethanol (45 mL, 4.5 vol). The wet cake was charged back to the reactor and slurried in 95% ethanol (380 mL, 38 vol) for two hours at 20° C. The suspension was then filtered (same cloth) and washed with 95% ethanol (30 mL, 3 vol). The wet cake was again slurried in 95% EtOH (170 mL, 17 vol) at 20° C., filtered (same cloth), and washed with 95% ethanol (30 mL, 3 vol). The wet cake was then slurried in acetone (170 mL, 17 vol) at 20° C. overnight, followed by filtration (same cloth) and acetone wash (20 mL, 2 vol). The acetone (170 ml, 17 vol) treatment was repeated on the solids and stirred for 2 hours. The suspension was filtered (same cloth) and washed with acetone (30 mL, 3 vol) and died at 45° C. and dried at 45° C. (18 hours) to provide canary yellow solid (10.81 g 91.0%).

Representative synthesis of BisEDT at 15° C. with 1 hour addition of thiol via syringe pump, and polypropylene cloth for filtration: The synthesis BisEDT was performed on 10-g scale, temperature profile was studied with data logger. Ethane dithiol was added at 15° C. over 1 hour via syringe pump and the filtration was performed using PP filter cloth. To a 1-L jacketed reactor was charged USP water (480 mL, 48 vol) and cooled to 15° C., followed by 70% HNO$_3$ (34 mL, 3.4 vol). A solution of bismuth subnitrate (10 g, 6.84 mmols) in water (43 mL, 4.3 vol) and 70% HNO$_3$ (14 mL, 1.4 vol) was added at the same temperature. The 95% ethanol (180 mL, 18 vol) was then added slowly. (Ethanol addition is exothermic, temperature reached 22.5° C.). It was then allowed to cool to 15° C. This was followed by dropwise addition of 1,2 ethanedithiol (4.3 mL, 7.5 mmols in 95% ethanol in 94 mL, 9.4 vol) over an hour with the batch temperature at 15° C. The reaction was allowed to stir at 15° C. overnight. The reaction mixture was filtered through polypropylene cloth and washed with 95% ethanol (45 mL, 4.5 vol). The wet cake was charged back to the reactor and slurried in 95% ethanol (380 mL, 38 vol) for two hours at 20° C. The suspension was then filtered (same cloth) and washed with 95% ethanol (30 mL, 3 vol). The wet cake was again slurried in 95% EtOH (170 mL, 17 vol) at 20° C., filtered (same cloth), and washed with 95% ethanol (30 mL, 3 vol). The wet cake was then slurried in acetone (170 mL, 17 vol) at 20° C. overnight, followed by filtration (same cloth) and acetone wash (20 mL, 2 vol). The acetone (170 ml, 17 vol) treatment was repeated on the solids and stirred for 2 hours. The suspension was filtered (same cloth) and washed with acetone (30 mL, 3 vol) and died at 45° C. and dried at 45° C. (18 hours) to provide canary yellow solid (10.43 g 87.8%).

TABLE 15

Particle Size Distribution of BisEDT samples

| Sample | D(10) µm | D(50) µm | D(90) µm | D[4.3] µm | Conditions |
|---|---|---|---|---|---|
| 1 | 0.80 | 2.4 | 5.9 | 2.9 | Dalton Synthesis Conditions |
| 2 | 0.58 | 1.7 | 3.9 | 2.0 | Dalton Synthesis Conditions |

TABLE 15-continued

Particle Size Distribution of BisEDT samples

| Sample | D(10) μm | D(50) μm | D(90) μm | D[4.3] μm | Conditions |
|---|---|---|---|---|---|
| 3 | 0.59 | 1.9 | 4.5 | 2.3 | 30° C., 5 h addition of 1,2-ethane dithiol via addition funnel |
| 4 | 0.44 | 1.48 | 3.1 | 1.7 | 30° C., 4 hour addition of 1,2-ethane dithiol via syringe pump |
| 5 | 0.33 | 0.72 | 1.6 | 0.86 | 20° C., 1 h addition of 1,2-ethane dithiol via addition funnel |
| 6 | 0.34 | 0.87 | 1.8 | 0.98 | 20° C., 4 h addition of 1,2-ethane dithiol via addition funnel |
| 7 | 0.39 | 1.3 | 1.6 | 1.4 | 20° C., 1 hour addition of 1,2-ethane dithiol via syringe pump. Sample slurried in EtOH. Cloth filtration |
| 8 | 0.36 | 1.0 | 1.8 | 1.0 | 20° C., 1 hour addition of 1,2-ethane dithiol via syringe pump. Sample slurried in MeOH. Cloth filtration |
| 9 | 0.67 | 1.0 | 1.9 | 1.1 | 20° C., 1 hour addition of 1,2-ethane dithiol via syringe pump. Sample slurried in Abs. MeOH. Cloth filtration |
| 10 | 0.36 | 0.88 | 1.7 | 0.97 | 20° C., 1 hour addition of 1,2-ethane dithiol via syringe pump. Sample slurried in IPA. Cloth filtration |
| 11 | 0.38 | 1.2 | 2.4 | 1.4 | 15° C. 1.5 hour addition of 1,2-ethane dithiol via syringe pump. Cloth filtration |
| 12 | 0.37 | 1.2 | 2.4 | 1.3 | 20° C., 1.25 hour addition of 1,2-ethane via syringe pump |
| 13 | 0.36 | 0.98 | 2.1 | 1.2 | 10° C., 1 h addition of 1,2-ethane dithiol via syringe pump |
| 14 | 0.36 | 1.0 | 2.1 | 1.2 | 10° C. 1 hour addition of 1,2-ethane dithiol via syringe pump. Cloth filtration |
| 15 | 0.32 | 0.72 | 1.6 | 0.86 | 10° C., 4 hours addition of 1,2-ethane dithiol via syringe pump. Cloth filtration. |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed:

1. A pharmaceutical composition comprising BisEDT suspended therein, wherein the composition comprises a plurality of microparticles comprising said BisEDT, wherein the microparticles have a D90 of less than 2 μm.

2. The pharmaceutical composition of claim 1, wherein the composition further comprises about 0.05% to about 1.0% polysorbate 80, about 0.05 to 40 mM sodium chloride, optionally about 1% to about 10% of methylcellulose, and optionally about 2 to 20 mM sodium phosphate at about pH 7.4.

3. The pharmaceutical composition of claim 1, wherein the microparticles have a volumetric mean diameter (VMD) from about 0.4 μm to about 2.5 μm.

4. The pharmaceutical composition of claim 1, wherein at least 70% of the microparticles have a volumetric mean diameter (VMD) from about 0.4 μm to about 2.5 μm.

5. The pharmaceutical composition of claim 1, wherein at least 80% of the microparticles have a volumetric mean diameter (VMD) from about 0.4 μm to about 2.5 μm.

6. The pharmaceutical composition of claim 1, wherein at least 90% of said microparticles having a volumetric mean diameter of from about 0.6 μm to about 2.5 μm.

7. The pharmaceutical composition of claim 1, wherein the microparticles have a D90 of less than or equal to 1.6 μm.

8. The pharmaceutical composition of claim 1, wherein the microparticles have a D50 of less than or equal to 1 μm.

9. The pharmaceutical composition of claim 1, wherein the composition is formulated for topical administration.

10. The pharmaceutical composition of claim 9, wherein the topical administration is to an area of non-intact skin.

11

16. The pharmaceutical composition of claim 1, wherein the composition is a liquid suspension.

17. The pharmaceutical composition of claim 16, wherein the liquid suspension is an aqueous liquid suspension.

18. The pharmaceutical composition of claim 1, wherein said plurality of microparticles are solid microparticles.

* * * * *